United States Patent [19]

Grese

[11] Patent Number: 5,726,186

[45] Date of Patent: Mar. 10, 1998

[54] PENTACYCLIC COMPOUNDS, INTERMEDIATES, PROCESSES, COMPOSITIONS, AND METHODS

[75] Inventor: Timothy Alan Grese, Indianapolis, Ind.

[73] Assignee: Eli Lilly and Company, Indianapolis, Ind.

[21] Appl. No.: 696,279

[22] Filed: Aug. 13, 1996

Related U.S. Application Data

[60] Provisional application No. 60/003,496 Sep. 8, 1995.

[51] Int. Cl.$^6$ .................. A61K 31/445; A61K 31/41; C07D 405/12; C07D 405/14

[52] U.S. Cl. .................. 514/321; 514/422; 514/434; 514/453; 514/232.8; 546/196; 546/197; 546/198; 546/200; 546/202; 548/421; 548/517; 548/527; 549/24; 549/383; 549/384; 544/125; 544/145; 544/146; 544/150; 544/153

[58] Field of Search ........................ 546/196, 197, 546/198, 200, 202; 548/421, 517, 527; 549/24, 383, 384; 574/321, 422, 434, 453

[56] References Cited

U.S. PATENT DOCUMENTS

| | | | |
|---|---|---|---|
| 4,230,862 | 10/1980 | Suarez et al. | 546/237 |
| 4,418,068 | 11/1983 | Jones | 546/202 |
| 5,147,880 | 9/1992 | Jones | 514/319 |
| 5,457,117 | 10/1995 | Black | 514/337 |
| 5,466,830 | 11/1995 | Sabatucci | 549/315 |

OTHER PUBLICATIONS

Walser A et al. J. Heterocycl. Chem. 12 (2), 351–8, 1975.
Fujisaki, et al Nippon Kagaku Kaishi, 739–42 (1979).
Triphenylmethyl, XXXIII, Quinoidation in the Triarylmethyls, M. Gomberg, and F.F. Blicke, J.A.C.S. 45, 1765–79 (1923).
Halochromic Salts from Some Triarylmethylthioglycolic Acids, M. Gomberg and W.E. Gordon, J.A.C.S. 57, 119–24 (1935).

*Primary Examiner*—C. Warren Ivy
*Assistant Examiner*—Evelyn Huang
*Attorney, Agent, or Firm*—Janelle D. Strode; David E. Boone

[57] ABSTRACT

The present invention provides compounds of formula I:

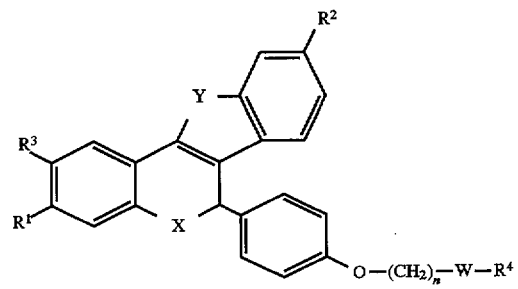

wherein

X is —O— or —S—,

Y is —O—, —S—, —CH$_2$—, —CH$_2$CH$_2$—, —CH=CH—, or —NR$^5$—;

R$^1$, R$^2$, and R$^3$ are each independently —H, —OH, —O(C$_1$-C$_4$ alkyl), —OCOC$_6$H$_5$, —OCO(C$_1$-C$_6$ alkyl), —OSO$_2$(C$_4$-C$_6$ alkyl), —OSO$_2$CF$_3$, Cl, or F;

n is 1 or 2;

W is CH$_2$ or C=O;

R$^4$ is 1-piperidinyl, 2-oxo-1-piperidinyl, 1-pyrrolidinyl, methyl-1-pyrrolidinyl, dimethyl-1-pyrrolidinyl, 2-oxo-1-pyrrolidinyl, 4-morpholino, dimethylamino, diethylamino, or 1-hexamethyleneimino;

R$^5$ is C$_1$-C$_3$ alkyl, —COC$_6$H$_5$, —CO(C$_1$-C$_6$ alkyl), —C(O)OC$_6$H$_5$, —C(O)O(C$_1$-C$_6$ alkyl), —SO$_2$(C$_1$-C$_6$ alkyl), —SO$_2$C$_6$H$_5$, or —SO$_2$CF$_3$;

or a pharmaceutically acceptable salt or solvate thereof.

10 Claims, No Drawings

PENTACYCLIC COMPOUNDS, INTERMEDIATES, PROCESSES, COMPOSITIONS, AND METHODS

This application claims the benefit of U.S. Provisional Application No. 60/003,496, filed Sep. 8, 1995.

FIELD OF THE INVENTION

This invention relates to the fields of pharmaceutical and organic chemistry and provides novel pentacyclic compounds which are useful for the treatment of the various medical indications associated with post-menopausal syndrome, and uterine fibroid disease, endometriosis, and aortal smooth muscle cell proliferation. The present invention further relates to intermediate compounds and processes useful for preparing the pharmaceutically active compounds of the present invention, and pharmaceutical compositions.

BACKGROUND OF THE INVENTION

"Post-menopausal syndrome" is a term used to describe various pathological conditions which frequently affect women who have entered into or completed the physiological metamorphosis known as menopause. Although numerous pathologies are contemplated by the use of this term, three major effects of post-menopausal syndrome are the source of the greatest long-term medical concern: osteoporosis, cardiovascular effects such as hyperlipidemia, and estrogen-dependent cancer, particularly breast and uterine cancer.

Osteoporosis describes a group of diseases which arise from diverse etiologies, but which are characterized by the net loss of bone mass per unit volume. The consequence of this loss of bone mass and resulting bone fracture is the failure of the skeleton to provide adequate structural support for the body. One of the most common types of osteoporosis is that associated with menopause. Most women lose from about 20% to about 60% of the bone mass in the trabecular compartment of the bone within 3 to 6 years after the cessation of menses. This rapid loss is generally associated with an increase of bone resorption and formation. However, the resorptive cycle is more dominant and the result is a net loss of bone mass. Osteoporosis is a common and serious disease among post-menopausal women.

There are an estimated 25 million women in the United States, alone, who are afflicted with this disease. The results of osteoporosis are personally harmful and also account for a large economic loss due its chronicity and the need for extensive and long term support (hospitalization and nursing home care) from the disease sequelae. This is especially true in more elderly patients. Additionally, although osteoporosis is not generally thought of as a life threatening condition, a 20% to 30% mortality rate is related with hip fractures in elderly women. A large percentage of this mortality rate can be directly associated with post-menopausal osteoporosis.

The most vulnerable tissue in the bone to the effects of post-menopausal osteoporosis is the trabecular bone. This tissue is often referred to as spongy or cancellous bone and is particularly concentrated near the ends of the bone (near the joints) and in the vertebrae of the spine. The trabecular tissue is characterized by small osteoid structures which inter-connect with each other, as well as the more solid and dense cortical tissue which makes up the outer surface and central shaft of the bone. This inter-connected network of trabeculae gives lateral support to the outer cortical structure and is critical to the bio-mechanical strength of the overall structure. In post-menopausal osteoporosis, it is, primarily, the net resorption and loss of the trabeculae which leads to the failure and fracture of bone. In light of the loss of the trabeculae in post-menopausal women, it is not surprising that the most common fractures are those associated with bones which are highly dependent on trabecular support, e.g., the vertebrae, the neck of the weight bearing bones such as the femur and the fore-arm. Indeed, hip fracture, collies fractures, and vertebral crush fractures are hall-marks of post-menopausal osteoporosis.

At this time, the only generally accepted method for treatment of post-menopausal osteoporosis is estrogen replacement therapy. Although therapy is generally successful, patient compliance with the therapy is low primarily because estrogen treatment frequently produces undesirable side effects.

Throughout premenopausal time, most women have less incidence of cardiovascular disease than age-matched men. Following menopause, however, the rate of cardiovascular disease in women slowly increases to match the rate seen in men. This loss of protection has been linked to the loss of estrogen and, in particular, to the loss of estrogen's ability to regulate the levels of serum lipids. The nature of estrogen's ability to regulate serum lipids is not well understood, but evidence to date indicates that estrogen can upregulate the low density lipid (LDL) receptors in the liver to remove excess cholesterol. Additionally, estrogen appears to have some effect on the biosynthesis of cholesterol, and other beneficial effects on cardiovascular health.

It has been reported in the literature that post-menopausal women having estrogen replacement therapy have a return of serum lipid levels to concentrations to those of the pre-menopausal state. Thus, estrogen would appear to be a reasonable treatment for this condition. However, the side-effects of estrogen replacement therapy are not acceptable to many women, thus limiting the use of this therapy. An ideal therapy for this condition would be an agent which would regulate the serum lipid level as does estrogen, but would be devoid of the side-effects and risks associated with estrogen therapy.

The third major pathology associated with post-menopausal syndrome is estrogen-dependent breast cancer and, to a lesser extent, estrogen-dependent cancers of other organs, particularly the uterus. Although such neoplasms are not solely limited to a post-menopausal women, they are more prevalent in the older, post-menopausal population. Current chemotherapy of these cancers has relied heavily on the use of anti-estrogen compounds such as, for example, tamoxifen. Although such mixed agonist-antagonists have beneficial effects in the treatment of these cancers, and the estrogenic side-effects are tolerable in acute life-threatening situations, they are not ideal. For example, these agents may have stimulatory effects on certain cancer cell populations in the uterus due to their estrogenic (agonist) properties and they may, therefore, be contraproductive in some cases. A better therapy for the treatment of these cancers would be an agent which is an anti-estrogen compound having negligible or no estrogen agonist properties on reproductive tissues.

In response to the clear need for new pharmaceutical agents which are capable of alleviating the symptoms of, inter alia, post-menopausal syndrome, the present invention provides new pentacyclic compounds, pharmaceutical compositions thereof, and methods of using such compounds for the treatment of post-menopausal syndrome and other estrogen-related pathological conditions such as those mentioned below.

Uterine fibrosis (uterine fibroid disease) is an old and ever present clinical problem which goes under a variety of names, including uterine fibroid disease, uterine hypertrophy, uterine lieomyomata, myometrial hypertrophy, fibrosis uteri, and fibrotic metritis. Essentially, uterine fibrosis is a condition where there is an inappropriate deposition of fibroid tissue on the wall of the uterus.

This condition is a cause of dysmenorrhea and infertility in women. The exact cause of this condition is poorly understood but evidence suggests that it is an inappropriate response of fibroid tissue to estrogen. Such a condition has been produced in rabbits by daily administrations of estrogen for 3 months. In guinea pigs, the condition has been produced by daily administration of estrogen for four months. Further, in rats, estrogen causes similar hypertrophy.

The most common treatment of uterine fibrosis involves surgical procedures both costly and sometimes a source of complications such as the formation of abdominal adhesions and infections. In some patients, initial surgery is only a temporary treatment and the fibroids regrow. In those cases a hysterectomy is performed which effectively ends the fibroids but also the reproductive life of the patient. Also, gonadotropin releasing hormone antagonists may be administered, yet their use is tempered by the fact they can lead to osteoporosis. Thus, there exists a need for new methods for treating uterine fibrosis, and the methods of the present invention satisfy that need.

Endometriosis is a condition of severe dysmenorrhea, which is accompanied by severe pain, bleeding into the endometrial masses or peritoneal cavity and often leads to infertility. The cause of the symptoms of this condition appear to be ectopic endometrial growths which respond inappropriately to normal hormonal control and are located in inappropriate tissues. Because of the inappropriate locations for endometrial growth, the tissue seems to initiate local inflammatory-like responses causing macrophage infiltration and a cascade of events leading to initiation of the painful response. The exact etiology of this disease is not well understood and its treatment by hormonal therapy is diverse, poorly defined, and marked by numerous unwanted and perhaps dangerous side effects.

One of the treatments for this disease is the use of low dose estrogen to suppress endometrial growth through a negative feedback effect on central gonadotropin release and subsequent ovarian production of estrogen; however, it is sometimes necessary to use continuous estrogen to control the symptoms. This use of estrogen can often lead to undesirable side effects and even the risk of endometrial cancer.

Another treatment consists of continuous administration of progestins which induces amenorrhea and by suppressing ovarian estrogen production can cause regressions of the endometrial growths. The use of chronic progestin therapy is often accompanied by the unpleasant CNS side effects of progestins and often leads to infertility due to suppression of ovarian function.

A third treatment consists of the administration of weak androgens, which are effective in controlling the endometriosis; however, they induce severe masculinizing effects. Several of these treatments for endometriosis have also been implicated in causing a mild degree of bone loss with continued therapy. Therefore, new methods of treating endometriosis are desirable.

Smooth aortal muscle cell proliferation plays an important role in diseases such as atherosclerosis and restenosis. Vascular restenosis after percutaneous transluminal coronary angioplasty (PTCA) has been shown to be a tissue response characterized by an early and late phase. The early phase occurring hours to days after PTCA is due to thrombosis with some vasospasms while the late phase appears to be dominated by excessive proliferation and migration of aortal smooth muscle cells. In this disease, the increased cell motility and colonization by such muscle cells and macrophages contribute significantly to the pathogenesis of the disease. The excessive proliferation and migration of vascular aortal smooth muscle cells may be the primary mechanism to the reocclusion of coronary arteries following PTCA, atherectomy, laser angioplasty and arterial bypass graft surgery. See "Intimal Proliferation of Smooth Muscle Cells as an Explanation for Recurrent Coronary Artery Stenosis after Percutaneous Transluminal Coronary Angioplasty," Austin et al., *Journal of the American College of Cardiology*, 8: 369–375 (August 1985).

Vascular restenosis remains a major long term complication following surgical intervention of blocked arteries by percutaneous transluminal coronary angioplasty (PTCA), atherectomy, laser angioplasty and arterial bypass graft surgery. In about 35% of the patients who undergo PTCA, reocclusion occurs within three to six months after the procedure. The current strategies for treating vascular restenosis include mechanical intervention by devices such as stents or pharmacologic therapies including heparin, low molecular weight heparin, coumarin, aspirin, fish oil, calcium antagonist, steroids, and prostacyclin. These strategies have failed to curb the reocclusion rate and have been ineffective for the treatment and prevention of vascular restenosis. See "Prevention of Restenosis after Percutaneous Transluminal Coronary Angioplasty: The Search for a 'Magic Bullet'," Hermans et al., *American Heart Journal*, 122: 171–187 (July 1991).

In the pathogenesis of restenosis excessive cell proliferation and migration occurs as a result of growth factors produced by cellular constituents in the blood and the damaged arterial vessel wall which mediate the proliferation of smooth muscle cells in vascular restenosis.

Agents that inhibit the proliferation and/or migration of smooth aortal muscle cells are useful in the treatment and prevention of restenosis. The present invention provides for the use of compounds as smooth aortal muscle cell proliferation inhibitors and, thus inhibitors of restenosis.

Transforming growth factor-$\beta$ (TGF-$\beta$) is a peptide growth factor which refers to a generic family of peptides, often called isoforms meaning that members of the family either share amino acid homology and/or have similar physiological actions. The TGF-$\beta$'s, particularly those designated TGF-$\beta_1$, $\beta_2$, and $\beta_3$, are particularly associated with processes involved in tissue repair and diseases associated with abnormal repair processes (see, Sporn and Roberts "The Transforming Growth Factor-$\beta$'s", *Peptide Growth Factors and their Receptors I*, 419–472 (Berlin: Springer Verlag, 1990)).

Agents which induce the production of TGF-$\beta$'s, and in particular TGF-$\beta_3$, are useful in promoting tissue repair and treating diseases which involve abnormal tissue repair. Such utilities include but are not limited to wound-healing, reduction of scarring (see, Ferguson, "Wound Healing, Scarring, TGF-$\beta$ Antagonists, and Isoforms", Abst. NIH TGF-$\beta$ Symposium, Bethesda Md., 3 May 1994), and ulcerative mucositis induced by chemotherapy and radiotherapy (see, Sonis and Haley, "Prevention of Chemotherapy-Induced Ulcerative Mucositis by Transforming Growth Factor-$\beta_3$", Abst. NIH TGF-$\beta$ Symposium, Bethesda Md., 3 May 1994). The present invention provides for the use of compounds as promoters of tissue repair processes and as treatments for diseases involving abnormal tissue repair.

SUMMARY OF THE INVENTION

The present invention relates to compounds of formula I

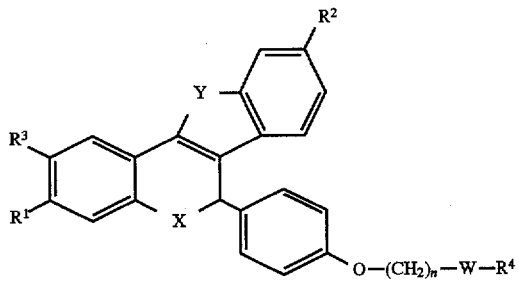

wherein

X is —O—, —S—, or —NR$^5$—;

Y is —O—, —S—, —CH$_2$—, —CH$_2$CH$_2$—, —CH=CH—, or —NR$^5$—;

R$^1$, R$^2$, and R$^3$ are each independently —H, —OH, —O(C$_1$-C$_4$ alkyl), —OCOC$_6$H$_5$, —OCO(C$_1$-C$_6$ alkyl), —OSO$_2$(C$_4$-C$_6$ alkyl), —OSO$_2$CF$_3$, Cl, or F;

n is 1 or 2;

W is CH$_2$ or C=O;

R$^4$ is 1-piperidinyl, 2-oxo-1-piperidinyl, 1-pyrrolidinyl, methyl-1-pyrrolidinyl, dimethyl-1-pyrrolidinyl, 2-oxo-1-pyrrolidinyl, 4-morpholino, dimethylamino, diethylamino, or 1-hexamethyleneimino;

R$^5$ is C$_1$-C$_3$ alkyl, —COC$_6$H$_5$, —CO(C$_1$-C$_6$ alkyl), —C(O)OC$_6$H$_5$, —C(O)O(C$_1$-C$_6$ alkyl), —SO$_2$(C$_1$-C$_6$ alkyl), —SO$_2$C$_6$H$_5$, or —SO$_2$CF$_3$;

or a pharmaceutically acceptable salt thereof.

Also provided by the present invention are compounds of formula II

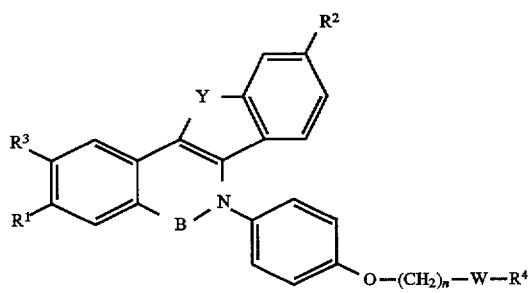

wherein

B is —CH$_2$— or —CO—

Y, R$^1$, R$^2$, R$^3$, R$^4$, n, and W are as defined above;

or a pharmaceutically acceptable salt thereof.

Also provided by the present invention are intermediate compounds of formula III and VI which are useful for preparing the pharmaceutically active compounds of the present invention, and are shown below

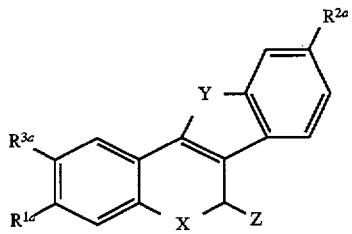

wherein

R$^{1a}$, R$^{2a}$, and R$^{3a}$ are each independently —H, —O(C$_1$-C$_4$ alkyl), —Cl, —F, or a suitably protected hydroxyl;

Z is —OH, —OC$_6$H$_5$, —O(C$_1$-C$_4$ alkyl), or 4-hydroxyphenyl;

X and Y are as defined above;

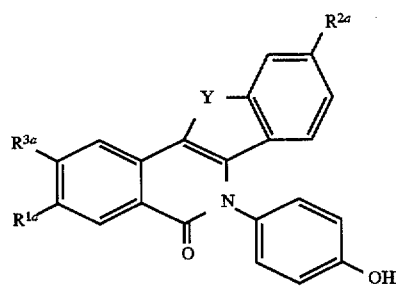

wherein

R$^{1a}$, R$^{2a}$, R$^{3a}$, and Y are as defined above.

The present invention further relates to pharmaceutical compositions containing compounds of formula I or formula II, optionally containing estrogen or progestin, and the use of such compounds, alone, or in combination with estrogen or progestin, for alleviating the symptoms of post-menopausal syndrome, particularly osteoporosis, cardiovascular related pathological conditions, and estrogen-dependent cancer. As used herein, the term "estrogen" includes steroidal compounds having estrogenic activity such as, for example, 17b-estradiol, estrone, conjugated estrogen (Premarin®), equine estrogen, 17a-ethynyl estradiol, and the like. As used herein, the term "progestin" includes compounds having progestational activity such as, for example, progesterone, norethylnodrel, nongestrel, megestrol acetate, norethindrone, and the like.

The compounds of the present invention also are useful for inhibiting uterine fibroid disease and endometriosis in women and aortal smooth muscle cell proliferation, particularly restenosis, in humans.

Also provided by the present invention is a process for preparing a compound of formula Ia

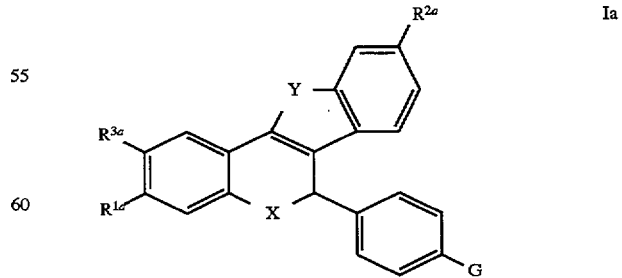

wherein

R$^{1a}$, R$^{2a}$, and R$^{3a}$ are each independently —H, —O(C$_1$-C$_4$ alkyl), —Cl, —F, or a suitably protected hydroxyl;

X and Y are as defined above;

G is —OH or —O(CH$_2$)$_n$WR$^4$ wherein n, W, and R$^4$ are as defined above;

or a pharmaceutically acceptable salt thereof, which comprises a) reacting a compound of formula IIIa

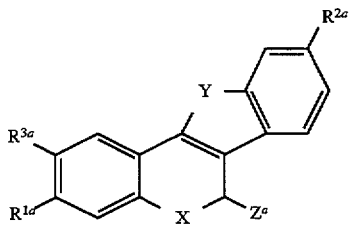

IIIa wherein

R$^{1a}$, R$^{2a}$, R$^{3a}$, X, and Y are as defined above;

Z$^a$ is —OH, —OC$_6$H$_5$, —O(C$_1$-C$_4$ alkyl), with a Grignard reagent of formula IVa

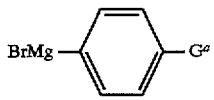

IVa wherein

G$^a$ is —OSi(CH$_3$)$_3$, a suitably protected hydroxyl which can be selectively deprotected in the presence of R$^{1a}$, R$^{2a}$, and R$^{3a}$, or —O(CH$_2$)$_n$WR$^4$ wherein n, W, and R$^4$ are as defined above;

b) when G$^a$ is —OSi(CH$_3$)$_3$ or another suitable protecting group optionally removing the said protecting group and thereafter reacting the resulting —OH with Q—(CH$_2$)$_n$—W—R$^4$ wherein Q is bromo, chloro, or hydroxy; and c) optionally salifying the reaction product from step a) or b).

DETAILED DESCRIPTION OF THE INVENTION

One aspect of the present invention includes compounds of formula I

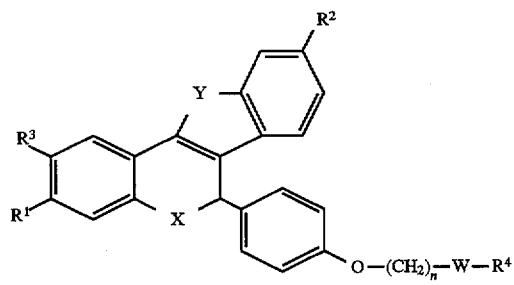

I wherein

X is —O—, —S—, or —NR$^5$—;

Y is —O—, —S—, —CH$_2$—, —CH$_2$CH$_2$—, —CH═CH—, or —NR$^5$—;

R$^1$, R$^2$, and R$^3$ are each independently —H, —OH, —O(C$_1$-C$_4$ alkyl), —OCOC$_6$H$_5$, —OCO(C$_1$-C$_6$ alkyl), —OSO$_2$(C$_4$-C$_6$ alkyl), —OSO$_2$CF$_3$, Cl, or F;

n is 1 or 2;

W is CH$_2$ or C═O;

R$^4$ is 1-piperidinyl, 2-oxo-1-piperidinyl, 1-pyrrolidinyl, methyl-1-pyrrolidinyl, dimethyl-1-pyrrolidinyl, 2-oxo-1-pyrrolidinyl, 4-morpholino, dimethylamino, diethylamino, or 1-hexamethyleneimino;

R$^5$ is C$_1$-C$_3$ alkyl, —COC$_6$H$_5$, —CO(C$_1$-C$_6$ alkyl), —C(O)OC$_6$H$_5$, —C(O)O(C$_1$—C$_6$ alkyl), —SO$_2$(C$_1$-C$_6$ alkyl), —SO$_2$C$_6$H$_5$, or —SO$_2$CF$_3$;

or a pharmaceutically acceptable salt thereof.

General terms used in the description of compounds herein described bear their usual meanings. For example, "C$_1$-C$_6$ alkyl" refers to straight or branched aliphatic chains of 1 to 6 carbon atoms including methyl, ethyl, propyl, isopropyl, butyl, n-butyl, pentyl, isopentyl, hexyl, isohexyl, and the like.

The starting material for one route of preparing compounds of the present invention are compounds of formula V below,

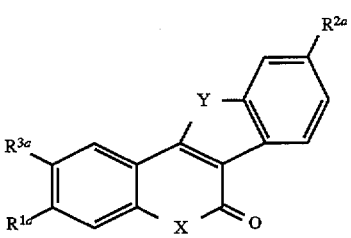

V wherein

R$^{1a}$, R$^{2a}$, and R$^{3a}$ are each independently —H, —O(C$_1$-C$_4$ alkyl), —F, —Cl, or a suitably protected hydroxyl;

X and Y are as defined above;

One embodiment of this starting material, compounds of formula Vb

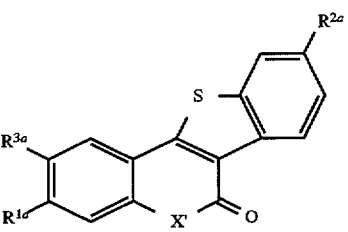

Vb wherein

R$^{1a}$, R$^{2a}$, and R$^{3a}$ are as defined above;

X' is —O—, —S—, or —NH—;

are made essentially as described in Journal of Organic Chemistry, 40: 3169 (1975). Preferably, R$^{1a}$ and R$^{2a}$ are methoxy or a suitably protected hydroxyl, R$^{3a}$ is —H, and X' is —O—.

In general, a readily available thioindoxyl of the formula

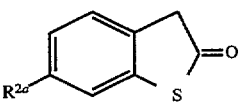

wherein R$^{2a}$ is as defined above, is reacted with a benzaldehyde of the formula wherein $x^b$ is —OH, —SH, or —NH$_2$, and $R^{1a}$ and $R^{2a}$ are as defined above. The reaction generally is carried out in the presence of a mild base such as triethylamine and a protic solvent such as ethanol, and is run at ambient temperature or below. The product of this condensation is then dehyrogenated by various methods known in the art, most preferably via reaction with 2,3-dichloro-5,6-dicyano-1,4-benzoquinone (DDQ) to give a compound of formula V.

If so desired, a compound of formula V in which $R^{1b}$, $R^{2b}$, and/or $R^{3b}$ is methoxy may be deprotected by reaction with aluminum trichloride and ethanethiol and reprotected with an alternative phenol protecting group at this stage. Protecting groups which are removable under mild conditions such as t-butyldimethylsilyl are preferred.

Alternative starting materials of formula Vc

Vc wherein
$R^{1c}$ and $R^{2c}$ are suitably protected hydroxyls;
are available by standard protection of commercially available coumestrol. Protecting groups which are removable under mild conditions such as t-butyldimethylsilyl are preferred.

Starting materials of formula Vd

Vd wherein
$R^{1a}$, $R^{2a}$, and $R^{3a}$ are as defined above;
X" is —O— or —S—; and
Y" is —CH$_2$—, —CH$_2$—CH$_2$—, or —CH=CH—, are prepared by von Pechman reaction as described in *Organic Reactions*, 7:1 (1953).

In general, a readily available tetralone or indanone of the formula wherein $R^{2a}$ is as defined above, and $y^d$ is —CH$_2$— or —CH$_2$—CH$_2$—, is condensed with an appropriately substituted phenol or thiophenol:

wherein
$R^{1a'}$ is —OH, —H, —O(C$_1$-C$_4$ alkyl), —F, —Cl, or a suitably protected hydroxyl;
$R^{3a}$ is as defined above; and
$X^d$ is —OH or —SH,
under the influence of a condensing agent such as phosphorus oxychloride, phosphorus pentoxide, sulfuric acid, aluminum chloride or the like. Preferably $R^{1a'}$ is —OH, $R^{3a}$ is —H, $X^d$ is OH, $Y^d$ is CH$_2$CH$_2$, and $R^{2a}$ is methoxy and the reaction is carried out in toluene or benzene at 80°–110° C. utilizing phosphorus oxychloride as the condensing agent.

If the von Pechman product contains a phenolic moiety it may be protected at this stage, or alternatively if $R^{2d}$ is methoxy, it may be subjected to a dealkylation/reprotection sequence as described supra. If so desired, the optional double bond may then be installed by reaction with DDQ or another dehydrogenating agent.

Additional starting materials of formula Ve

Ve wherein
$X^e$ and $Y^e$ are each independently —O—, —S—, —NH—, or —NR$^5$;
$R^{1a}$, $R^{2a}$, $R^{3a}$, and $R^5$ are as defined above; are prepared essentially as described in *Heterocycles*, 35: 1425 (1993); U.S. Pat. No. 5,073,553 issued Dec. 17, 1991; and *Indian Journal of Chemistry*, 24B: 556 (1989).

Other starting materials, of the formula

Vf wherein
$R^{1a}$, $R^{2a}$, and $R^{3a}$ are as defined above;
$X^f$ is —NH— or —NR$^5$—; and
$Y^f$ is —CH$_2$—, —CH$_2$—CH$_2$—, or —CH=CH, are prepared essentially as described in *Indian Journal of Chemistry*, 14B: 132 (1976) and in *Journal of the Chemical Society, Perkin Trans. I*, 1747 (1974). If the double bond ($Y^f$=—CH=CH—) is desired, it may be obtained in the manner described supra, by the use of DDQ.

Once a compound of formula V, has been formed, one option allows for reduction of the selected formula V compound to a compound of formula IIIb

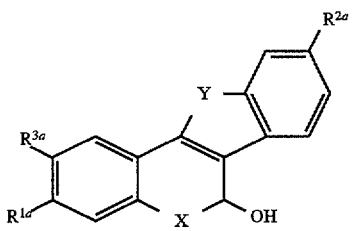

wherein $R^{1a}$, $R^{2a}$, $R^{3a}$, X, and Y are as defined above;

by reaction with an appropriate reducing agent such as diisobutylaluminum hydride in a solvent such as toluene, $CH_2Cl_2$, or THF. Generally this reduction is carried out at a temperature below 0° C. and preferably between −50° C. and −100° C. The formula IIIb compound may then be converted, either in situ or in a separate step to a compound of formula IIIc below

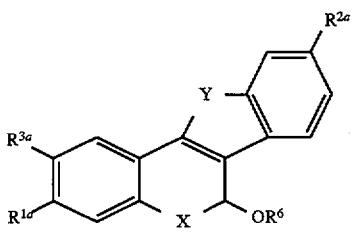

wherein $R^6$ is —$C_1$-$C_4$ alkyl or —$C_6H_5$ or $R^{1a}$, $R^{2a}$, $R^{3a}$, X, and Y are as defined above;

by reaction with an alcohol or phenol $R^6OH$ and, optionally an acidic compound or dehydrating agent such as magnesium sulfate. It is preferable to carry out this conversion in a separate step, in $CH_2Cl_2$ or chlorobenzene, between ambient temperature and reflux. Preferably, $R^{1a}$ and $R^{2a}$ are suitably protected hydroxyls, $R^{3a}$ is H, X is —O—, Y is —O— or —S—, and $R^6$ is —$C_6H_5$.

Alternatively, a compound of formula V in which X is —NH— may be acylated on nitrogen and then directly converted to a formula IIIc compound by reaction with $NaBH_4$ or a similar reducing agent in the presence of an acidic compound such as HCl and an alcoholic solvent. In this embodiment of IIIc it is preferable that $R^{1a}$ and $R^{2a}$ are methoxy, $R^{3a}$ is H, X is —N(COC$_6$H$_5$)— or —N(COC(CH$_3$)$_4$)—, Y is —O—, and $R^6$ is preferably —$C_2H_5$.

In the next step, a formula IIIb or IIIc compound is reacted with an aryl Grignard reagent of formula

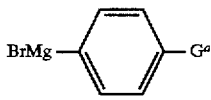

wherein $G^a$ is —OSi(CH$_3$)$_3$, a suitably protected hydroxyl which can be selectively deprotected in the presence of $R^{1a}$ and $R^{2a}$, or —(CH$_2$)$_n$WR$^4$;

wherein n, W, and $R^4$ are as defined above; in a solvent such as toluene, THF, diethyl ether, $CH_2Cl_2$, or a mixture thereof and at ambient temperature or below. Optionally, the reaction may be facilitated by the presence of a Lewis acid such as boron trifluoride etherate, tin tetrachloride, titanium tetrachloride or the like.

When $G^a$ of formula IVa is —O(CH$_2$)$_n$WR$^4$ this Grignard reaction provides a compound of formula Ib

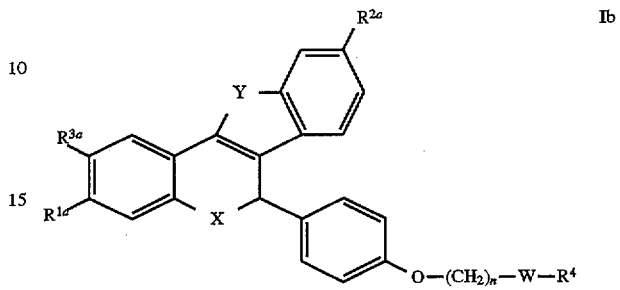

wherein $R^{1a}$, $R^{2a}$, and $R^{3a}$ are each independently —H, —O(C$_1$-C$_4$ alkyl), —Cl, —F, or a suitably protected hydroxyl;

X, Y, n, W, and $R^4$ are as defined above;

which can be optionally deprotected and derivatized as described infra to provide the desired formula I compound.

Alternatively, when $G^a$ of formula IVa is —OSi(CH$_3$)$_3$ or another suitably protected hydroxyl, the protecting group is cleaved at this stage under conditions which leave $R^{1a}$, $R^{2a}$, and $R^{3a}$ intact, to provide a compound of formula Ic

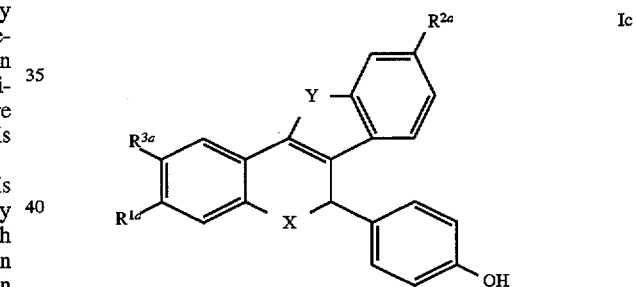

wherein $R^{1a}$, $R^{2a}$, $R^{3a}$, X, and Y are as defined above. Such conditions are dependent upon the nature of the protecting groups and are known to those skilled in the art [see, e.g., Greene and Wuts, *Protective Groups in Organic Synthesis*, 2nd ed., (1991)]. In a preferred embodiment, in which $R^{1a}$ and $R^{2a}$ are t-butyldimethylsilyloxy or methoxy, $R^{3a}$ is H, and $G^a$ is —OSi(CH$_3$)$_4$ this may be accomplished by brief exposure to a methanolic slurry of potassium carbonate at ambient temperature or below in the presence of a cosolvent such as THF or diethyl ether.

A formula Ic compound may be converted to a formula Ib compound by utilizing one of the synthetic routes shown in Scheme I. In Scheme I, $R^{1a}$, $R^{2a}$, $R^{3a}$, $R^4$, W, X, Y, and n are as defined above.

Scheme I

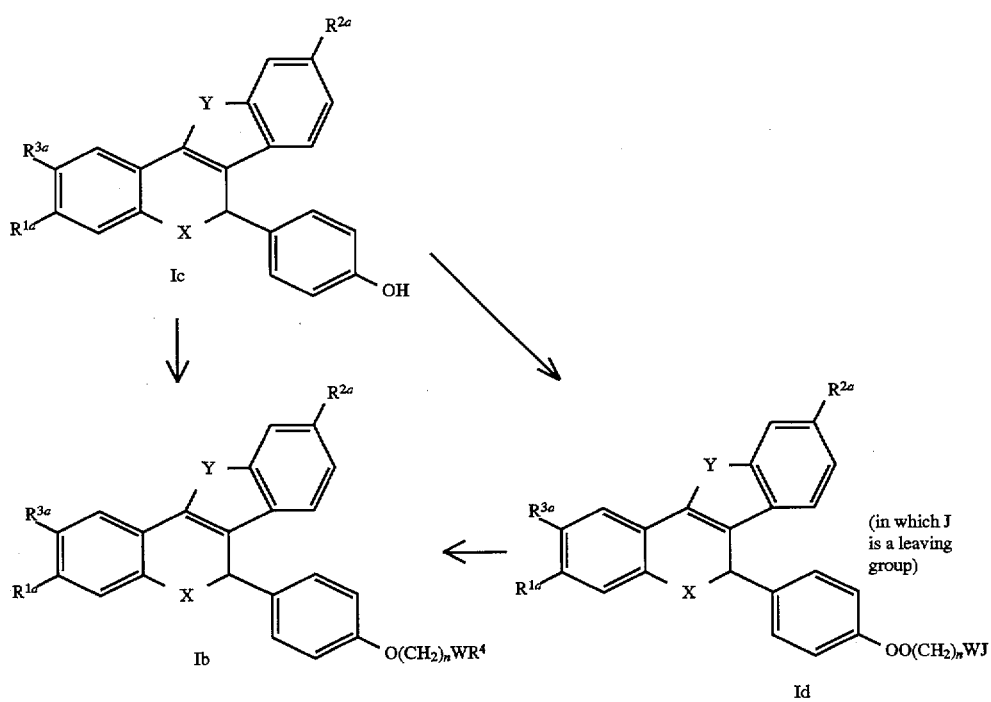

Each step of Scheme I is carried out via procedures well known to one of ordinary skill in the art.

For example, a formula Ic compound can be reacted with a compound of the formula

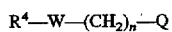

wherein $R^4$, W, and n are as defined above and Q is a bromo or, preferably, a chloro moiety, to provide compounds of formula Ib. This alkylation is normally achieved by carrying out the reaction in the presence of an excess of finely powdered potassium carbonate and using an equivalent to slight excess of the Q—$(CH_2)$—$R^3$ reactant.

A more preferred method involves the reaction of a formula Ic compound with a compound of formula

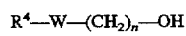

wherein $R^4$, W, and n are as defined above in the presence of triphenylphosphine, diethyl azodicarboxylate (DEAD), and an appropriate solvent, resulting in a formula Ib compound. This process is known in the art as a Mitsunobu coupling. Preferably, 2–4 equivalents of 1-(2-hydroxyethyl) pyrrolidine are reacted with a formula Ic compound in the presence of 2–5 equivalents each of triphenylphosphine and DEAD, in an inert solvent such as toluene at ambient temperature. At this temperature the reaction only takes about 30 minutes to about 3 hours, however changes in the reaction conditions will influence the amount of time this reaction needs to be run to completion. Of course, the progress of this reaction step can be monitored via standard chromatographic techniques.

In yet another synthetic route, a formula Ic compound is reacted with an excess of an alkylating agent of the formula

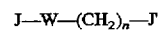

wherein J and J' each are the same or different leaving group, in an alkali solution.

Appropriate leaving groups include, for example, the sulfonates such as methanesulfonate, 4-bromosulfonate, toluenesulfonate, ethanesulfonate, isopropanesulfonate, 4-methoxybenzenesulfonate, 4-nitrobenzenesulfonate, 2-chlorobenzene sulfonate, and the like, halogens such as bromo, chloro, iodo, and the like, and other related groups. A preferred alkylating agent is 1,2-dibromoethane, and at least 2 equivalents, preferably, more than 2 equivalents, of 1,2-dibromoethane is used per equivalent of substrate.

A preferred alkali solution for this alkylation reaction contains potassium carbonate in an inert solvent such as, for example, methyethyl ketone (MEK) or DMF. In this solution, the 4-hydroxy group of the benzoyl moiety of a formula IIId compound exists as a phenoxide ion which displaces one of the leaving groups of the alkylating agent.

This reaction is best run when the alkali solution containing the reactants and reagents is brought to reflux and allowed to run to completion. When using MEK as the preferred solvent, reaction times run from about 6 hours to about 20 hours.

Alternatively, a compound of formula Id can be prepared by the reaction of an alcohol of formula

wherein J is selected from the leaving groups described above, with a formula Ic compound via a Mitsunobu coupling procedure. A preferred alcohol is 2-bromoethanol.

The reaction product from this step, a compound of formula Id, is then reacted with 1-piperidine, 1-pyrrolidine, methyl-1-pyrrolidine, dimethyl-1-pyrrolidine, 4-morpholine, dimethylamine, diethylamine, or 1-hexamethyleneimine, via standard techniques, to form compounds of formula Ib. Preferably, the hydrochloride salt of piperidine is reacted with the formula Ib compound in an inert solvent, such as anhydrous DMF, and heated to a temperature in the range from about 60° C. to about 110° C.

When the mixture is heated to a preferred temperature of about 90° C., the reaction only takes about 30 minutes to about 1 hour. However, changes in the reaction conditions will influence the amount of time this reaction needs to be run to completion. Of course, the progress of this reaction step can be monitored via standard chromatographic techniques.

Dealkylation/deprotection of terminally-protected hydroxy groups in formula Ia compounds can be carried out if so desired to provide pharmaceutically active compounds of formula I, via procedures known to one of ordinary skill in the art. A preferred method for the deprotection of t-butyldimethylsilylethers, a preferred embodiment of $R^{1a}$ and $R^{2a}$, involves stirring them in an appropriate solvent such as THF with a soluble fluoride source such as tetra-n-butylammonium fluoride at ambient temperature.

The above procedures provide novel, pharmaceutically active compounds of formula I in which $R^1$, $R^2$, and $R^3$ each are hydrogen, hydroxy, $C_1$–$C_4$ alkoxy, chloro, or fluoro. Preferred formula Ia compounds are those in which $R^1$ and $R^2$ each are methoxy, or $R^1$ and $R^2$ each are hydroxy, $R^3$ is H, $R^4$ is piperidinyl or pyrrolidinyl, X is —O—, Y is —S—, W is —CH$_2$—, and n is 1. These preferred compounds, as well as other formula Ia compounds, can be used as pharmaceutical agents or can be further derivitized to provide other formula I compounds which also are useful for practicing the methods of the present invention.

An alternative "one-pot" method for the preparation of a formula I or Ia compound from a compound of formula V can also be employed. This route involves:

1) The reduction of a formula V compound by diisobutylaluminum hydride or a similar reducing agent in THF at a temperature below –60° C.

2) Quenching of excess reducing agent with a molar equivalent of a protic solvent such as methanol or isopropanol.

3) Addition of an aryl Grignard reagent of the formula

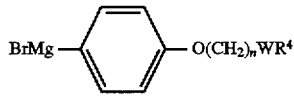

and warming to ambient temperature.

4) Standard extractive work-up of the reaction mixture and concentration.

5) Optional treatment of a THF solution of the remnant with a strong acid, such as HCl, for a period of up to 24 h and subsequent basic work-up. In some cases, the "one-pot" method may provide formula Ia products which may be deprotected as described supra. Alternatively, the final acid treatment may induce concommitant deprotection and result in the direct preparation of formula I compounds. Preferred formula I compounds from this reaction are the same as those preferred formula I compounds described above, and can be used as pharmaceutically active agents for the methods herein described, or can be derivatized to provide other novel compounds of formula I which also are useful for the present methods (infra).

Another aspect of the present invention includes compounds of formula II

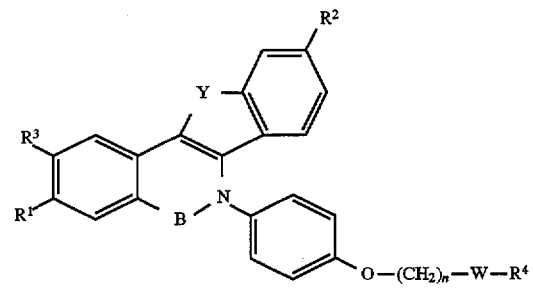

wherein

B is —CH$_2$— or —CO—

Y, $R^1$, $R^2$, $R^3$, $R^4$, n, and W are as defined above; or a pharmaceutically acceptable salt thereof.

A key intermediate in the preparation of formula II compounds is a compound of formula VI

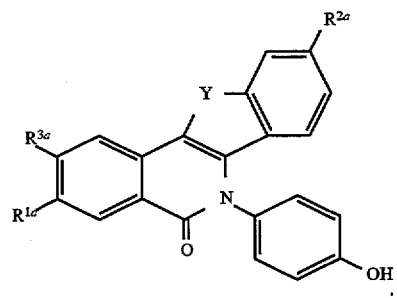

wherein $R^{1a}$, $R^{2a}$, $R^{3a}$, and Y are as defined above. The synthesis of a preferred embodiment of VI, VIa in which Y is —CH$_2$CH$_2$— is described in Scheme II.

Scheme II

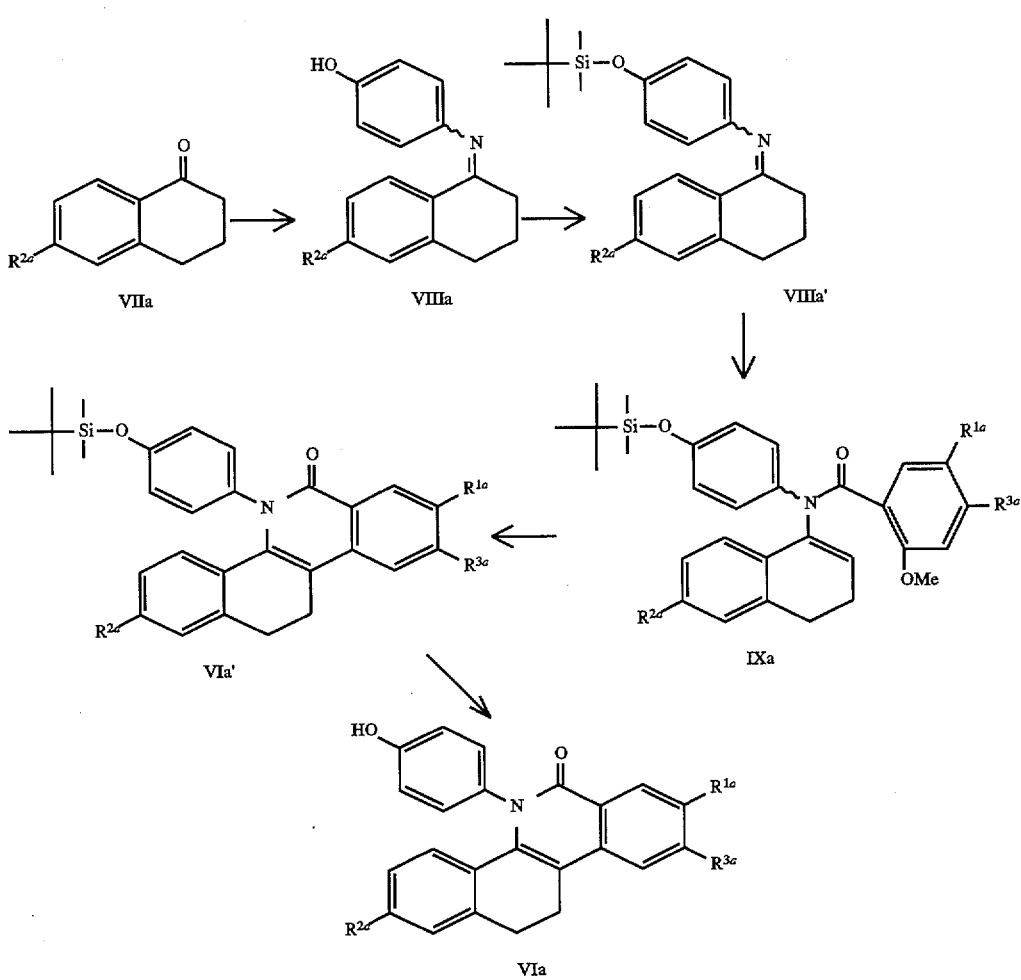

Thus, a readily available tetralone VIIa wherein $R^{2a}$ is as defined above is condensed with one equivalent of 4-aminophenol, preferably in the absence of solvent, at a temperature such that the mixture is molten, usually c. 180° C. under a nitrogen stream. During the course of the reaction, additional 4-aminophenol may be added to replace material lost via sublimation. The resulting imine of formula VIIIa solidifies upon cooling, and may be optionally recrystallized.

Protection of the hydroxyl group of VIIIa as its silyl derivative VIIIa' is carried out under standard conditions, and the imine is converted to an enamide of formula IXa by acylation with an aroyl halide of formula

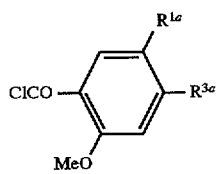

wherein $R^{1a}$ and $R^{2a}$ are as defined above, generally in the presence of a mild base such as triethylamine and in an inert solvent such as $CH_2Cl_2$ at a temperature between ambient and reflux.

A compound of formula IXa is then photolyzed in a quartz immersion well, using a Hanovia mercury lamp, in a solvent such as ether or benzenes for a period of 4 h to 1 week to provide a compound of formula VIa'. The procedure is essentially as described in *Journal of the Chemical Society, Perkin Transactions I*, 762 (1975).

Desilylation of a formula VIa' compound under standard conditions then provides a compound of formula VIa. For a listing of appropriate conditions see, e.g., Greene and Wuts, *Protective Groups in Organic Synthesis*, 2nd ed., p. 80, 161 (1991). Preferred formula VI compounds are those in which $R^{1a}$ and $R^{2a}$ are each individually —H or methoxy, and $R^{3a}$ is —H. Most preferred is the compound in which both $R^{1a}$ and $R^{2a}$ are methoxy.

A compound of formula VI is converted to a compound of formula IIb

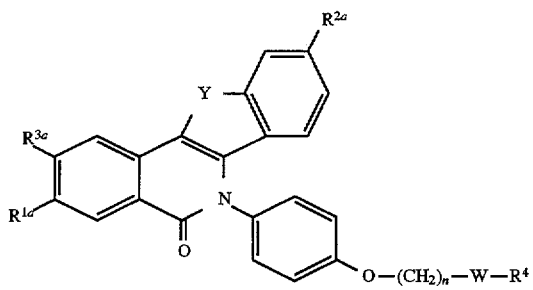

wherein $R^{1a}$, $R^{2a}$, $R^{3a}$, $R^4$, Y, n, and W are as described above; by the methods described supra for the conversion of formula Ic compounds to formula Ib compounds. For example, a preferred method is the Mitsunobu coupling of a formula VI compound with 1-(2-hydroxyethyl)pyrrolidine or 1-(2-hydroxyethyl)piperidine.

Once a formula IIb compound is obtained, it may be optionally deprotected/dealkylated to provide a formula II compound or, alternatively it may be reduced to provide a compound of formula IIc

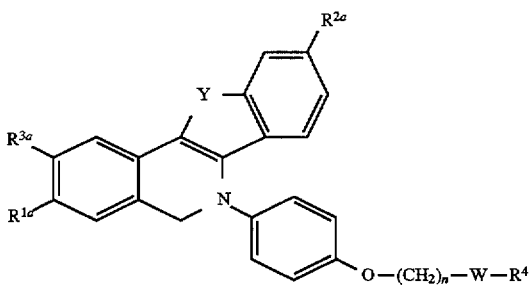

wherein $R^{1a}$, $R^{2a}$, $R^{3a}$, $R^4$, Y, n, and W are as described above. One method for carrying out this reduction involves reacting a formula IIa compound with lithium aluminum hydride in an inert solvent such as THF. If the reaction is carried out at ambient temperature an intermediate product can be isolated which, upon further reduction with sodium borohydride in acetic acid is converted to a formula IIc compound. Alternatively, if the reaction is carried out at reflux the desired formula IIc compound can be isolated directly. Compounds of formula IIc can be optionally dealkylated/deprotected to provide compounds of formula II.

In the preferred case where Y is —CH$_2$CH$_2$—, i.e. formula IIa

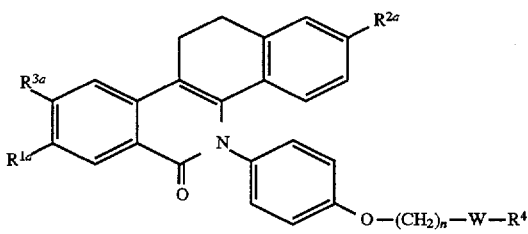

wherein $R^{1a}$, $R^{2a}$, $R^{3a}$, $R^4$, n, and W are as described above; it may be desirable to carry out a dehydrogenation reaction, thus providing a compound of formula IId

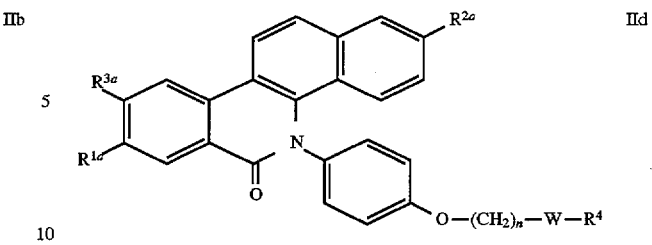

wherein $R^{1a}$, $R^{2a}$, $R^{3a}$, $R^4$, n, and W are as described above. This dehydrogenation may be effected by various methods known in the art, most preferably via reaction with 2,3-dichloro-5,6-dicyano-1,4-benzoquinone (DDQ).

Alternatively, it may be desirable to perform the dehydrogenation at an earlier stage in the synthesis on a compound of formula VIa' to provide a compound of formula VIb:

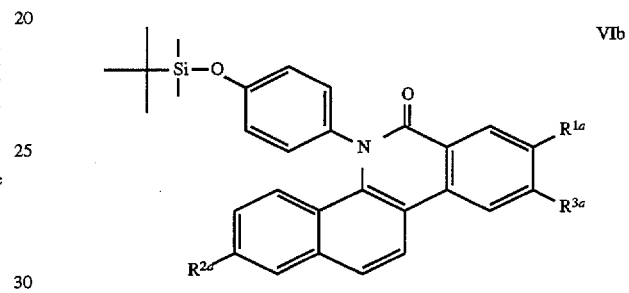

Compounds of formula VIb may then be converted to compounds of formula IIe by methods analogous to the conversion of VIa to IIa.

The formula IId compound can be optionally deprotected/dealkylated to provide a compound of formula II, or alternatively can be reduced, as described supra to provide a compound of formula IIe

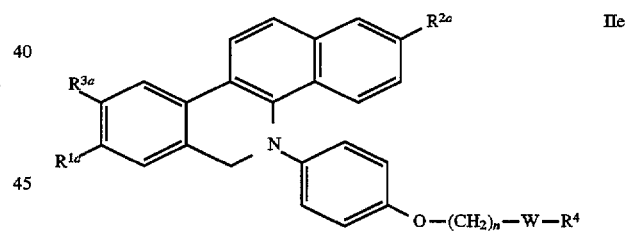

wherein $R^{1a}$, $R^{2a}$, $R^{3a}$, $R^4$, n, and W are as described above. A compound of formula IIe may then be optionally deprotected/dealkylated to provide a compound of formula II.

Collectively, formula IIa–e compounds with their various defined substituents, and/or the products of their deprotection as described above, are represented as compounds of formula II of the present invention.

For example, when $R^{1a}$, $R^{2a}$, and/or $R^{3a}$ of a formula IIe compound are $C_1$–$C_4$ alkyl hydroxy protecting groups, such groups can be removed via standard dealkylation techniques to prepare an especially preferred compound of formula IIe. In the most preferred examples of formula II compounds $R^1$ and $R^2$ are each individually —H, —OH, or methoxy, Y is —CH=CH—, B is —CH$_2$—, n is 1, W is —CH$_2$—, and $R^4$ is 1-piperidinyl or 1-pyrrolidinyl.

An alternative method involves the formation of preferred compounds of formula I or II by replacing the $R^1$, $R^2$, and/or $R^3$ hydroxy groups of a formula I or formula II compound with methoxy. This transformation is carried out by well known procedures (see, e.g., Greene and Wuts, *Protective Groups in Organic Synthesis*, 2nd ed., p. (1991)). An especially preferred method involves reaction of the mono- or diphenolic compound with excess diazomethane.

Other preferred compounds of formula I or II are prepared by replacing the newly formed $R^1$, $R^2$ and/or $R^3$ hydroxy groups of a formula I or formula II compound with a moiety of the formula —O—CO—($C_1$-$C_6$ alkyl), or —O—$SO_2$—($C_4$-$C_6$ alkyl) via well known procedures. See, e.g., U.S. Pat. No. 4,358,593.

For example, when an —O—CO($C_1$-$C_6$ alkyl) group is desired, the dihydroxy compound of formula I is reacted with an agent such as acyl chloride, bromide, cyanide, or azide, or with an appropriate anhydride or mixed anhydride. The reactions are conveniently carried out in a basic solvent such as pyridine, lutidine, quinoline or isoquinoline, or in a tertiary amine solvent such as triethylamine, tributylamine, methylpiperidine, and the like. The reaction also may be carried out in an inert solvent such as ethyl acetate, dimethylformamide, dimethylsulfoxide, dioxane, dimethoxyethane, acetonitrile, acetone, methyl ethyl ketone, and the like, to which at least one equivalent of an acid scavenger (except as noted below), such as a tertiary amine, has been added. If desired, acylation catalysts such as 4-dimethylaminopyridine or 4-pyrrolidinopyridine may be used. See, e.g., Haslam, et al., *Tetrahedron*, 36: 2409–2433 (1980).

The acylation reactions which provide the aforementioned terminal $R^1$, $R^2$ and $R^3$ groups of compounds of formula I or formula II are carried out at moderate temperatures in the range from about −25° C. to about 100° C., frequently under an inert atmosphere such as nitrogen gas. However, ambient temperature is usually adequate for the reaction to run.

Such acylations of these hydroxy group also may be performed by acid-catalyzed reactions of the appropriate carboxylic acids in inert organic solvents or heat. Acid catalysts such as sulfuric acid, polyphosphoric acid, methanesulfonic acid, and the like are used.

The aforementioned $R^1$, $R^2$ and/or $R^3$ groups of formula I or formula II compounds also may be provided by forming an active ester of the appropriate acid, such as the esters formed by such known reagents such as dicyclohexylcarbodiimide, acylimidazoles, nitrophenols, pentachlorophenol, N-hydroxysuccinimide, and 1-hydroxybenzotriazole. See, e.g., *Bull. Chem. Soc. Japan*, 38: 1979 (1965), and *Chem. Ber.*, 788 and 2024 (1970).

Each of the above techniques which provide —O—CO—($C_1$-$C_6$ alkyl) moieties are carried out in solvents as discussed above. Those techniques which do not produce an acid product in the course of the reaction, of course, do not call for the use of an acid scavenger in the reaction mixture.

When a formula I or formula II compound is desired in which the $R^1$, $R^2$ and/or $R^3$ group of a formula I compound is converted to a group of the formula —O—$SO_2$—($C_4$-$C_6$ alkyl) or —O—$SO_2$—$CF_3$, the formula I dihydroxy compound is reacted with, for example, a sulfonic anhydride or a derivative of the appropriate sulfonic acid such as a sulfonyl chloride, bromide, or sulfonyl ammonium salt, as taught by King and Monoir, *J. Am. Chem. Soc.*, 97: 2566–2567 (1975), or with a reagent such as N-phenyltrifluoromethanesulfonimide, as taught by Hendrickson and Bergeron, *Tetrahedron Letters*, 4607 (1973). The dihydroxy compound also can be reacted with the appropriate sulfonic anhydride, mixed sulfonic anhydrides, or sulfonimides. Such reactions are carried out under conditions such as were explained above in the discussion of reaction with acid halides and the like.

In the case where $R^1$, $R^2$ and/or $R^3$ of a formula I or formula II compound has been converted to —O—$SO_2$—$CF_3$, said derivative can be further converted to a compound of formula I or formula II in which —O—$SO_2$—$CF_3$ groups have been replaced by —H. Thus the formula I or formula II trifluoromethanesulfonate is reduced under conditions described in Example 7, infra, or as taught by Ritter, *Synthesis*, 735 (1993).

Although the free-base forms of formula I and formula II compounds can be used in the methods of the present invention, it is occasionally advantageous to prepare and use a pharmaceutically acceptable salt form. Thus, the compounds used in the methods of this invention primarily form pharmaceutically acceptable acid addition salts with a wide variety of organic and inorganic acids, and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, b-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I or formula II with an equimolar or excess amount of acid. The reactants are generally combined in a mutual solvent such as diethyl ether or ethyl acetate. The salt normally precipitates out of solution within about one hour to 10 days and can be isolated by filtration or the solvent can be stripped off by conventional means.

The pharmaceutically acceptable salts generally have enhanced solubility characteristics compared to the compound from which they are derived, and thus are often more amenable to formulation as liquids or emulsions.

The following examples are presented to further illustrate the preparation of compounds of the present invention. It is not intended that the invention be limited in scope by reason of any of the following examples.

NMR data for the following Examples were generated on a GE 300 MHz NMR instrument, and anhydrous acetone-$d_6$ was used as the solvent unless otherwise indicated.

Preparation 1a

6-Methoxythianapthen-2-one

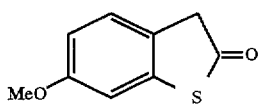

To tetrahydrofuran (200 mL) containing 2-dimethylamino-6-methoxybenzo-[b]-thiophene (cf. U.S. Pat. No. 5,420,349) (20.00 g, 96.5 mmol) was added 1N aqueous HCl (200 mL) and the resulting mixture was heated to reflux for 3 h. The mixture was cooled, the layers were separated, and the aqueous layer was extracted with dichloromethane (300 mL). The combined organic layers washed with water (250 mL), dried (MgSO$_4$), filtered and concentrated to give crude product, which was recrystallized from 3A-ethanol, and dried in vacuo at room temperature to afford the title compound (13.89 g, 77.0 mmol, 80%): mp 80°–82° C.; IR (KBr) 1713, 1605, 1485, 1287, 1015, 865, 813 cm$^{-1}$; $^1$H NMR (DMSO-d$_6$) δ7.22 (d, 1H, J=8.4 Hz), 7.11 (s, 1H), 6.78 (d, 1H, J=8.4 Hz), 4.06 (s, 2H), 3.71 (s, 3H); $^{13}$C NMR (DMSO-d$_6$) δ203.5, 159.0, 136.9, 125.6, 124.6, 112.3, 108.4, 55.3, 46.2. Anal. Calcd. for C$_9$H$_8$O$_2$S: C, 59.98; H, 4.47; S, 17.78. Found: C, 60.19; H, 4.57; S, 18.03.

Preparation 1b

6a, 11a-Dihydro-3,9-dimethoxy-6-H-[1]benzothieno[3,2-c][1]benzopyran-6-one

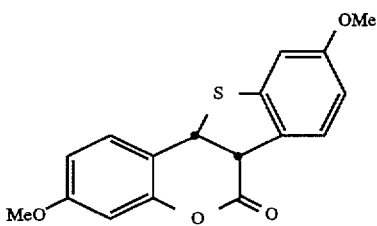

To a stirred solution of 6-methoxythianaphthen-2-one (see Docket B-9459) (20 g, 111 mmol) in a mixture of ethanol (100 mL) and methylene chloride (50 mL) was added 4-methoxysalicylaldehyde (17.5 g, 115 mmol) followed by triethylamine (567 mg, 784 mL, 5.6 mmol) at room temperature. After 30 min, a solid began to precipitate and stirring was continued overnight. The mixture was then diluted with cold hexane (1 L) and filtered to yield 28.7 g (82%) of the title product as an off-white solid, pure by $^1$H-NMR analysis. An analytical sample was obtained by recrystallization from toluene as light yellow crystals, mp 157–165 d°C.: $^1$H-NMR (300 MHz, CDCl$_3$) d 7.33 (d, J=8.6 Hz, 1H), 7.31 (d, J=8.1 Hz, 1H), 6.75 (d, J=2.4 Hz, 1H), 6.70 (m, 2H), 6.60 (d, J=2.5 Hz, 1H), 5.22 (d, J=7.2 Hz, 1H), 4.33 (d, J=7.2 Hz, 1H), 3.79 (s, 3H), 3.76 (s, 3H); IR (CHCl$_3$) 1759 cm$^{-1}$; MS (FD) m/e 314 (M+); Anal. calc'd. for C$_{17}$H$_{14}$O$_4$S: C, 64.95; H, 4.50. Found: C, 65.01; H, 4.58.

Preparation 2

3,9-Dimethoxy-6-H-[1]benzothieno[3,2-c][1]benzopyran-6-one

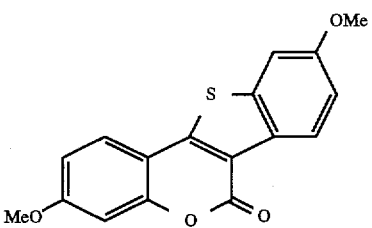

A mixture of the product of Preparation 2 (4.5 g, 14.3 mmol) and 2,3-dichloro-5,6-dicyano-1,4-benzoquinone (DDQ) (3.4 g, 15 mmol) in dichloroethane (100 mL) was heated briefly to 80° C., inducing the formation of a precipitate. The mixture was filtered hot, rinsing the precipitate with methylene chloride, and the mother liquor concentrated in vacuo. The remnant was dissolved in hot methylene chloride, filtered to remove residual hydroquinone, and reconcentrated. The product was recrystallized from toluene to provide 3.94 g (88%) of the title product as white needles, mp 220°–221° C.: $^1$H-NMR (acetone-d$_6$/DMSO-d$_6$) d 8.41 (d, J=8.9 Hz, 1H), 7.82 (d, J=8.7 Hz, 1H), 7.74 (d, J=2.3 Hz, 1H), 7.20 (dd, J=8.9, 2.4 Hz, 1H), 7.09 (d, J=2.4 Hz, 1H), 7.03 (dd, J=8.6, 2.4 Hz, 1H), 3.94 (s, 3H), 3.91 (s, 3H); IR (KBr) 1717 cm$^{-1}$; MS (FD+) m/e 312 (M+); Anal. calc'd. for C$_{17}$H$_{12}$O$_4$S: C, 65.37; H, 3.88. Found: C, 65.51; H, 3.90.

Preparation 3

3,9-Bis[(tert-butyldimethylsilyl)oxy]-6-H-[1]benzothieno[3,2-c][1]benzopyran-6-one

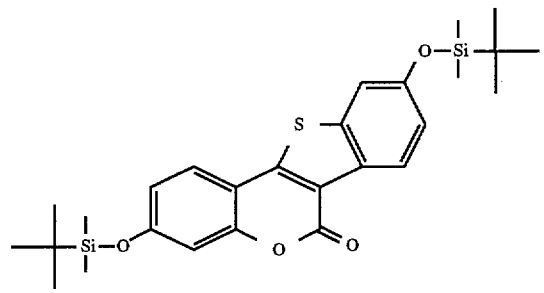

To a mechanically stirred slurry of the product of Preparation 2 (12 g, 38.4 mmol) in methylene chloride (220 mL) was added ethanethiol (11.9 g, 13.4 mL, 192 mmol) followed by aluminum chloride (38.4 g, 288 mmol), portionwise. The reaction mixture was stirred at ambient temperature for 5 h, then cooled to 0° C. and quenched cautiously with tetrahydrofuran (THF) (250 mL) followed by saturated sodium bicarbonate (250 mL). The mixture was diluted with THF (1 L), the layers separated, and the aqueous layer was washed with THF (200 mL). The combined organic layers were dried (sodium sulfate) and concentrated to yield 11.1 g (102%) of crude diphenol as a yellow solid, which was used without further purification.

The crude product was slurried in methylene chloride (220 mL) and treated with triethylamine (20.2 g, 28 mL, 200 mmol) and tert-butyldimethylsilyl chloride (20.3 g, 134.4 mmol). The mixture was stirred at ambient temperature for 5 h, during which it slowly became homogeneous. After dilution with hexane (600 mL), the mixture was washed with brine (600 mL) and the aqueous layer was extracted with hexane (300 mL). The combined organic layers were dried (sodium sulfate), concentrated, and the residue recrystallized from hexane to provide 18.0 g (91%) of the title compound as a fluffy white solid, mp 142°–144° C.: $^1$H-NMR (300 MHz, CDCl$_3$) d 8.50 (d, J=8.7 Hz, 1H), 7.58 (d, J=8.5 Hz, 1H), 7.32 (d, J=2.1 Hz, 1H), 7.05 (dd, J=8.7, 2.1 Hz, 1H), 6.92 (d, J=2.2 Hz, 1H), 6.84 (dd, J=8.4, 2.2 Hz, 1H), 1.01 (s, 9H), 1.00 (s, 9H), 0.27 (s, 6H), 0.25 (s, 6H); $^{13}$C-NMR (75 MHz, DMSO-d$_6$) d 158.4, 157.0, 154.6, 152.7, 149.6, 138.5, 130.5, 125.2, 124.6, 120.0, 117.6, 116.3, 112.7, 111.3, 108.0, 25.6, 25.6, 18.2, 18.2, −4.4, −4.4; IR (CHCl$_3$) 1717 cm$^{-1}$; MS (FD) m/e 512 (M+); Anal. calc'd. for C$_{27}$H$_{36}$O$_4$SSi$_2$: C, 63.24; H, 7.08. Found: C, 63.45; H, 7.36.

Preparation 4

3,9-Bis[(tert-butyldimethylsilyl)oxy]-6-H-[1]benzothieno[3,2-c][1]benzopyran-6-ol

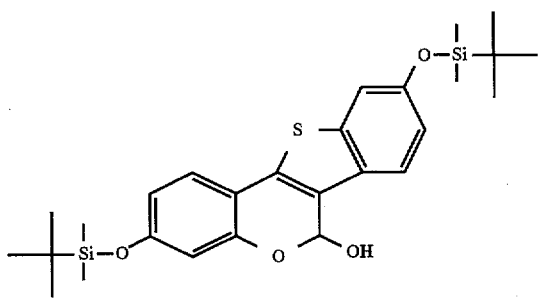

A solution of the produce from Preparation 3 (2.0 g, 3.9 mmol) in toluene (200 mL) was cooled to −92° C. and treated dropwise with a 1.0M toluene solution of diisobutylaluminum hydride (11.3 mL, 11.3 mmol) at a rate maintaining the internal temperature below −89° C. The mixture was stirred for approximately 3 h, as the temperature gradually rose to −77° C., then quenched with methanol (5 mL) and 10% aqueous citric acid (50 mL). After dilution with methylene chloride (200 mL), the mixture was washed with saturated potassium sodium tartrate (100 mL), and the aqueous layer was extracted with methylene chloride (2×200 mL). The combined organic layers were washed with brine (300 mL) and the brine wash was further extracted with methylene chloride (100 mL). The organic layers were dried (sodium sulfate), concentrated, and the remnant chromatographed (silica gel, 1–15% ethyl acetate/hexane) to yield 360 mg (18%) of starting material, 1.21 g (60%, 74% based on recovered starting material) of the titled compound as a white crystalline solid (analytical sample recrystallized from hexane/ethyl acetate, mp 162°–164° C.): $^1$H NMR (300 MHz) d 7.70 (d, J=9.0 Hz, 1H), 7.46 (d, J=2.1 Hz, 1H), 7.29 (d, J=8.1 Hz, 1H), 7.00 (dd, J=8.5, 1.8 Hz, 1H), 6.85 (br s, 1H), 6.6 (m, 2H), 6.39 (br s, 1H), 1.01 (s, 9H), 1.00 (s, 9H), 0.25 (s, 6H), 0.25 (s, 6H); $^{13}$C NMR (125 MHz) d 156.9, 153.3, 151.7, 139.9, 131.9, 124.5, 123.9, 121.7, 118.8, 113.7, 113.1, 112.7, 108.7, 90.7, 25.1, 25.1, 17.9, −5.2, −5.2; IR (CHCl$_3$) 3540 cm$^{-1}$; MS (FD+) m/e 514 (M+); Anal. calc'd. for C$_{27}$H$_{38}$O$_4$SSi$_2$: C, 62.98; H, 7.45. Found: C, 63.25; H, 7.68, and 260 mg (13%, 16% based on recovered starting material of the diol below

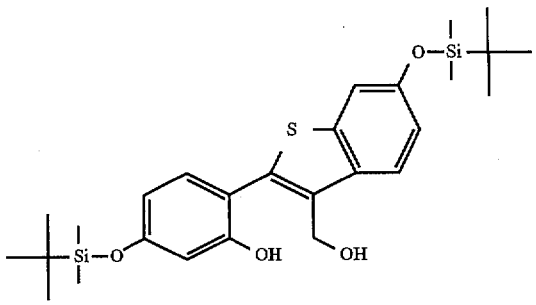

as an amorphous solid: $^1$H NMR (300 MHz, CDCl$_3$) d 7.73 (d, J=8.7 Hz, 1H), 7.29 (d, J=2.0 Hz, 1H), 7.16 (d, J=8.2 Hz, 1H), 6.98 (dd, J=8.7, 2.0 Hz, 1H), 6.5 (m, 3H), 6.30 (br s, 1H), 4.71 (s, 2H), 1.01 (s, 9H), 1.00 (s, 9H), 0.22 (s, 6H), 0.19 (s, 6H); IR (CHCl$_3$) 3600, 3510 cm$^{-1}$; MS (FD+) m/e 516 (M+); Anal. calc'd. for C$_{27}$H$_{40}$O$_4$SSi$_2$: C, 62.73; H, 7.82. Found: C, 62.49; H, 7.83.

Preparation 5

3,9-Bis[(tert-butyldimethylsilyl)oxy]-6-phenoxy-6-H-[1]benzothieno[3,2-c][1]benzopyran

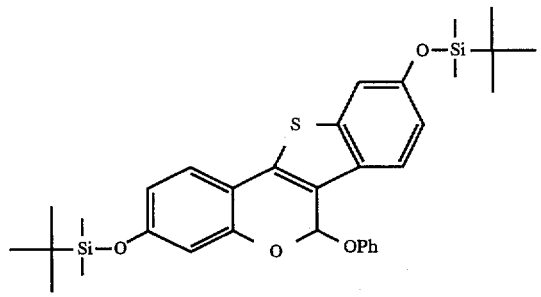

To a solution of the product of Preparation 4 (4.52 g, 8.78 mmol) and phenol (4.13 g, 43.9 mmol) in methylene chloride (100 mL) was added anhydrous magnesium sulfate (4.5 g) and the resultant slurry was stirred for 4 h at ambient temperature. The mixture was filtered and concentrated and the residue dissolved in chlorobenzene and reconcentrated in vacuo at approximately 70° C. The residue was then dissolved in methylene chloride (300 mL), washed with saturated sodium carbonate (3×300 mL) and water (2×300 mL), dried (sodium sulfate), and concentrated to yield 5.16 g (99%) of the title compound as an amorphous solid which was used without further purification: $^1$H NMR (300 MHz) d 7.67 (d, J=8.7 Hz, 1H), 7.50 (d, J=2.1 Hz, 1H), 7.4–7.5 (m, 4H), 7.23 (d, J=8.4 1H), 7.08 (t, J=7.2 Hz, 1H), 6.99 (dd, J=8.7, 2.1 Hz, 1H), 6.67 (dd, J=8.4, 2.3 Hz, 1H), 6.62 (d, J=2.3 Hz, 1H), 0.99 (s, 9H), 0.96 (s, 9H), 0.24 (s, 6H), 0.21 (s, 6H); $^{13}$C NMR (125 MHz) d 156.9, 153.3, 151.7, 139.9, 131.9, 124.5, 123.9, 121.7, 118.8, 113.7, 113.1, 112.7, 108.7, 90.7, 25.1, 25.1, 17.9, −5.2, −5.2; MS (FD+) m/e 590 (M+); Anal. calc'd. for C$_{33}$H$_{42}$O$_4$SSi$_2$: C, 67.06; H, 7.18. Found: C, 66.78; H, 6.96.

Preparation 6

3,9-Bis[(tert-butyldimethylsilyl)oxy]-6-[4-[2-(1-piperidinyl)ethoxy]phenyl]-6-H-[1]benzothieno[3,2-c][1]benzopyran

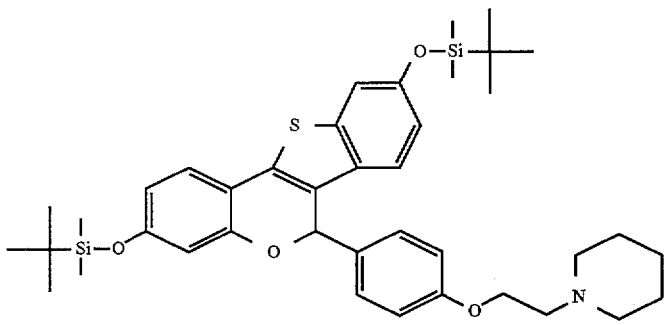

To a solution of the product of Preparation 5 (4.0 g, 6.7 mmol) in toluene (100 mL) at 0° C. was added a 0.5M THF solution of 4-[2-(1-piperidinyl)ethoxy]phenylmagnesium bromide (prepared from the corresponding bromobenzene and magnesium turnings, catalyzed by iodine in THF, 27 mL, 13.5 mmol). The mixture was allowed to warm to room temperature and stirred for 1.5 h. After quenching with water (300 mL), the mixture was extracted with ethyl acetate (2×300 mL), and the organic layer was dried (sodium sulfate) and concentrated. The residue was purified via chromatography (silica gel, 3:1 hexane:ethyl acetate, 0.1% ammonium hydroxide) to give 3.85 g (82%) of the title compound as a colorless, gummy solid: $^1$H NMR (300 MHz) d 7.45 (s, 1H), 7.2–7.3 (m, 4H), 6.8–6.9 (m, 3H), 6.68 (s, 1H), 6.51 (d, J=8.1 Hz, 1H), 6.36 (s, 1H), 4.01 (t, J=6.0 Hz, 2H), 2.62 (t, J=6.0 Hz, 2H), 2.41 (m, 4H), 1.4–1.6 (m, 4H), 1.3–1.4 (m, 2H), 0.99 (s, 9H), 0.96 (s, 9H), 0.22 (s, 6H), 0.20 (s, 6H); $^{13}$C NMR (125 MHz) d 160.3, 157.9, 154.0, 153.5, 141.0, 132.8, 132.6, 130.1, 129.8, 126.1, 124.8, 122.7, 119.4, 115.3, 114.5, 114.2, 114.0, 109.4, 78.2, 66.9, 58.5, 55.6, 26.8, 26.0, 26.0, 25.0, 18.7, −4.3, −4.3; MS (FD) m/e 702 (M+); Anal. calc'd. for $C_{40}H_{55}NO_4SSi_2$: C, 68.43; H, 7.90; N, 2.00. Found: C, 68.58; H, 8.00; N, 2.26.

EXAMPLE 1

3,9-Dihydroxy-6-[4-[2-(1-piperidinyl)ethoxy]phenyl]-6-H-[1]benzothieno[3,2-c][1]benzopyran

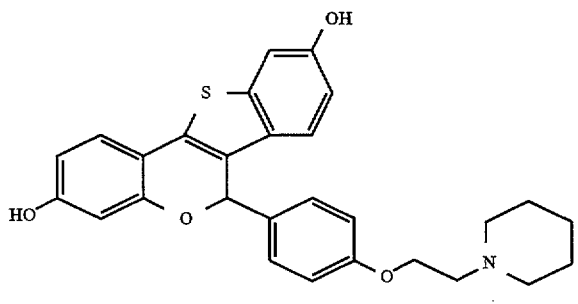

To a solution of the Preparation 6 product (3.85 g, 5.5 mmol) in THF (150 mL), was added a 1.0M THF solution of tetra-n-butylammonium fluoride (TBAF) (27.4 mL, 27.4 mmol). The solution was stirred at ambient temperature for 2 h, then diluted with ethyl acetate (300 mL) and washed with saturated ammonium chloride (300 mL). The aqueous layer was washed with ethyl acetate (150 mL), and the combined organic layers were washed with saturated sodium bicarbonate (300 mL), dried (sodium sulfate), and concentrated. The remnant was purified by chromatography (silica gel, 1:1 hexane:ethyl acetate, 10% methanol, 0.1% ammonium hydroxide) to give 2.35 g (90%) of the titled product as a red foam. Crystallization from methanol gave an off-white powder, mp 242–245 d°C.: $^1$H NMR (300 MHz) d 8.58 (br s, 2H), 7.35 (d, J=2.1 Hz, 1H), 7.26 (d, J=8.6 Hz, 2H), 7.17 (d, J=8.2 Hz, 1H), 7.16 (d, J=8.6 Hz, 1H), 6.84 (d, J=8.5 Hz, 2H), 6.80 (m, J=2.2 Hz, 1H), 6.63 (s, 1H), 6.46 (dd, J=8.2, 2.2 Hz, 1H), 6.35 (d, J=2.3 Hz, 1H), 4.02 (t, J=6.0 Hz, 2H), 2.63 (t, J=6.0 Hz, 2H), 2.42 (m, 4H), 1.4–1.6 (m, 4H), 1.3–1.4 (m, 2H); $^{13}$C NMR (125 MHz, dimethylformamide-$d_7$) d 160.2, 159.9, 156.4, 153.2, 140.8, 132.8, 130.9, 129.6, 125.3, 124.6, 122.5, 115.2, 115.1, 112.2, 109.6, 108.8, 108.7, 104.5, 77.6, 66.6, 58.3, 55.3, 26.5, 24.8; HRMS (FAB+) m/e calc'd. for $C_{28}H_{28}NO_4S$ 474.1739 (MH+), found 474.1726; Anal. calc'd. for $C_{28}H_{27}NO_4S \cdot 0.8H_2O$: C, 68.90; H, 5.92; N, 2.87. Found: C, 68.88; H, 5.76; N, 2.86.

EXAMPLE 2

3,9-Dimethoxy-6-[4-[2-(1-piperidinyl)ethoxy]phenyl]-6-H-[1]benzothieno[3,2-c][1]benzopyran

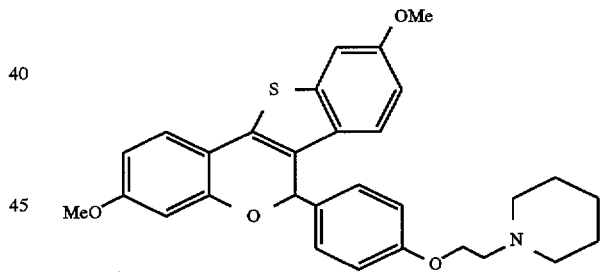

A solution of the product of Example 1 (300 mg, 0.633 mmol) in methanol (75 mL) was treated with a solution of diazomethane in ether/ethanol (approximately 16 mmol) at ambient temperature. The mixture was stirred until gas evolution ceased, nitrogen was bubbled through for 10 min to remove excess diazomethane, and the mixture was concentrated. Radial chromatography of the residue (1:1 hexane:ethyl acetate, 2% methanol, under an ammonia atmosphere) provided 118 mg (37%) of the title compound as white crystals, mp 134–36: $^1$H NMR (300 MHz) d 7.51 (d, J=2.2 Hz, 1H), 7.2–7.4 (m, J=8.6 Hz, 4H), 6.86 (m, 3H), 6.70 (s, 1H), 6.55 (dd, J=8.4, 2.3 Hz, 1H), 6.41 (d, J=2.4 Hz, 1H), 4.01 (t, J=6.0 Hz, 2H), 3.83 (s, 3H), 3.74 (s, 3H), 2.62 (t, J=6.0 Hz, 2H), 2.40 (m, 4H), 1.4–1.6 (m, 4H), 1.3–1.4 (m, 2H); $^{13}$C NMR (125 MHz, CDCl$_3$) d 160.8, 159.2, 157.1, 152.6, 140.3, 131.6, 131.3, 130.5, 129.1, 124.3, 124.0, 121.7, 114.6, 114.0, 112.8, 107.6, 105.7, 102.3, 77.9, 65.8, 57.8, 55.5, 55.2, 54.9, 25.9, 24.1; MS (FD+) m/e 501 (M+);

Anal. calc'd. for $C_{30}H_{31}NO_4S$: C, 71.83; H, 6.23; N, 2.79. Found: C, 71.53; H, 6.20; N, 2.84.

EXAMPLE 3

3,9-Bis(benzoyloxy)-6-[4-[2-(1-piperidinyl)ethoxy]phenyl]-6-H-[1]benzothieno[3,2-c][1]benzopyran

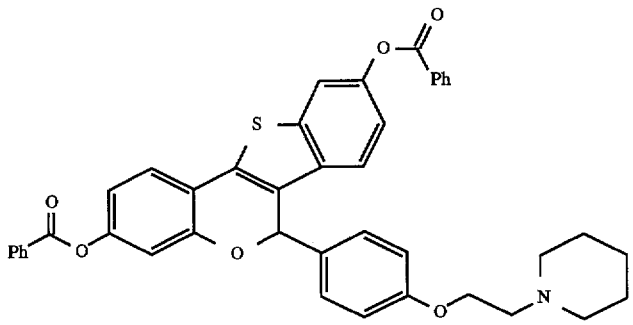

To a solution of the product of Example 1 (200 mg, 0.42 mmol) in methylene chloride (25 mL) at room temperature was added triethylamine (0.18 mL, 1.27 mmol) followed by benzoyl chloride (0.15 mL, 1.27 mmol) via syringe over 10 minutes. The reaction mixture was stirred for 16 hours and then washed with saturated sodium bicarbonate (25 ml) followed by water (25 ml). The organic layer was dried (sodium sulfate) and concentrated, and the residue was purified by radial chromatography (silica gel, 12:12:1 ethyl acetate:hexanes:methanol under an ammonia atmosphere) to afford 200 mg (69%) of the title compound as a tan solid: $^1$H NMR (300 MHz, DMSO-$d_6$) d 8.1–8.2 (m, 5H), 7.5–7.8 (m, 8H), 7.2–7.3 (m, 3H), 6.9–7.0 (m, 5H), 4.00 (t, J=5.5 Hz, 2H), 2.60 (t, J=4.8 Hz, 2H), 2.38 (m, 4H), 1.4–1.5 (m, 4H), 1.3–1.4 (m, 2H); HRMS (FAB+) m/e calc'd. for $C_{42}H_{36}NO_6S$ 682.2263 (MH+), found 682.2286.

EXAMPLE 4

3,9-Bis(pivaloyloxy)-6-[4-[2-(1-piperidinyl)ethoxy]phenyl]-6-H-[1]benzothieno[3,2-c][1]benzopyran

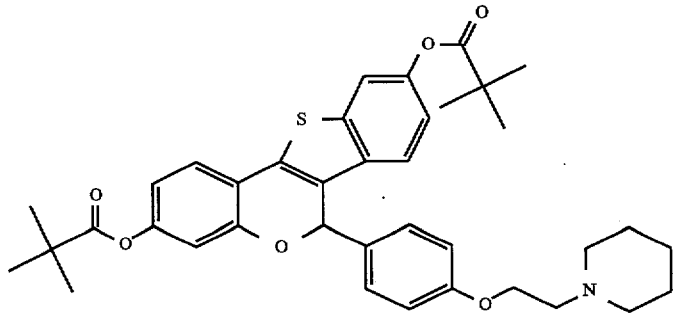

According to the procedure of Example 2, the product of Example 1 (200 mg, 0.42 mmol) was reacted with triethylamine (0.18 mL, 1.27 mmol) and pivaloyl chloride (0.16 mL, 1.27 mmol) in methylene chloride (25 mL) to afford 190 mg (70%) of the title compound as a white foam: $^1$H NMR (300 MHz, CDCl$_3$) d 7.58 (d, J=1.7 Hz, 1H), 7.35 (d, J=8.1 Hz, 1H), 7.26 (d, J=9.6 Hz, 2H), 7.14 (d, J=8.7 Hz, 1H), 6.93 (dd, J=8.8, 2.1 Hz, 1H), 6.83 (d, J=8.6 Hz, 2H), 6.70 (dd, J=4.3, 2.1 Hz, 1H), 6.63 (s, 2H), 4.13 (t, J=5.4 Hz, 2H), 2.83 (m, 2H), 2.58 (m, 4H), 1.66 (m, 4H), 1.46 (m, 2H), 1.37 (s, 9H), 1.33 (s, 9H); MS (FD+) m/e 641 (M+); HRMS (FAB+) m/e calc'd. for $C_{38}H_{44}NO_6S$ 642.2889 (MH+), found 642.2848; Anal. calc'd. for $C_{38}H_{43}NO_6S$: C, 71.11; H, 6.75; N, 2.18. Found: C, 71.86; H, 6.49; N, 2.09.

EXAMPLE 5

3,9-Bis(1-butylsulfonyloxy)-6-[4-[2-(1-piperidinyl)ethoxy]phenyl]-6-H-[1]benzothieno[3,2-c][1]benzopyran

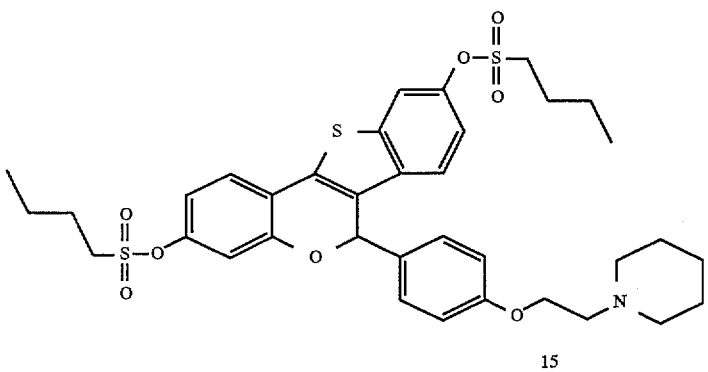

According to the procedure of Example 2, the product of Example 1 (200 mg, 0.42 mmol) was reacted with triethylamine (0.18 mL, 1.27 mmol) and n-butanesulfonyl chloride (0.17 mL, 1.27 mmol) in methylene chloride (25 mL) to afford 120 mg (40%) of the title compound as a clear brown gum: $^1$H NMR (300 MHz, CDCl$_3$) d 7.77 (s, 1H), 7.38 (d, J=8.5 Hz, 1H), 7.29 (d, J=9.5 Hz, 2H), 7.11 (s, 2H), 6.8–6.9 (m, 4H), 6.63 (s, 1H), 4.08 (t, J=5.4 Hz, 2H), 3.2–3.2 (m, 4H), 2.77 (t, J=5.4 Hz, 2H), 2.51 (m, 4H), 1.9–2.0 (m, 4H) 1.4–1.6 (m, 10H), 0.9–1.0 (m, 6H); HRMS (FAB+) m/e calc'd. for C$_{38}$H$_{44}$NO$_8$S$_3$ 714.2229 (MH+), found 714.2206.

EXAMPLE 6

3,9-Bis(trifluoromethanesulfonyloxy)-6-[4-[2-(1-piperidinyl)ethoxy]phenyl]-6-H-[1]benzothieno[3,2-c][1]benzopyran

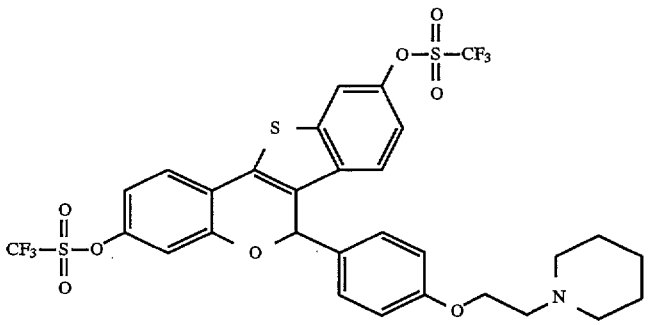

To a solution of the product of Example 1 (500 mg, 1.06 mmol) in THF (25 mL) containing dimethylformamide (2 mL) at room temperature was added triethylamine (0.64 g, 0.69 mL, 6.36 mmol) followed by N-phenyltrifluoromethanesulfonimide (0.83 g, 2.33 mmol). The reaction mixture was stirred for 12 hours, warmed to 60° C., and additional N-phenyltrifluoromethanesulfonimide (0.30 g, 0.85 mmol) was added. After 30 min, the reaction mixture was cooled to ambient temperature and concentrated, and the residue was purified by radial chromatography (silica gel, 1:1 hexane-:ethyl acetate, 1% methanol under an ammonia atmosphere) to afford 780 mg (100%) of the title compound as a white foam: $^1$H NMR (300 MHz, methanol-d$_4$) d 7.63 (d, J=8.8 Hz, 1H), 7.56 (d, J=2.5 Hz, 1H), 7.13 (dd, J=8.8, 2.7 Hz, 1H), 7.03 (d, J=8.8 Hz, 2H), 6.80 (d, J=8.9 Hz, 2H), 6.49 (d, J=2.5 Hz, 1H), 6.39 (d, J=8.7 Hz, 1H), 6.05 (dd, J=8.7, 2.6 Hz, 1H), 4.00 (t, J=5.5 Hz, 2H), 2.67 (m, 2H), 2.45 (m, 4H), 1.4–1.6 (m, 4H), 1.3–1.4 (m, 2H); $^{13}$C NMR (125 MHz) d 159.8, 152.8, 150.2, 146.9, 140.4, 136.6, 130.5, 129.2, 127.3, 125.3, 123.4, 119.2, 118.9, 116.3, 114.7, 114.6, 110.4, 77.7, 66.0, 57.6, 54.7, 25.8, 24.0; MS (FD) m/e 737 (M+); Anal. calc'd for C$_{30}$H$_{25}$F$_6$NO$_8$S$_3$: C, 48.84; H, 3.42; N, 1.90. Found: C, 49.05; H, 3.71; N, 1.72.

EXAMPLE 7

6-[4-[2-(1-piperidinyl)ethoxy]phenyl]-6-H-[1]benzothieno[3,2-c][1]benzopyran

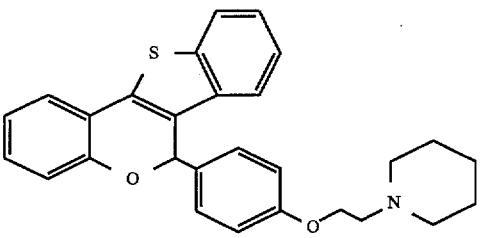

A solution of the product of Example 6 (780 mg, 1.06 mmol), palladium(II) acetate (42 mg, 0.19 mmol), 1,2-bis(diphenylphosphino)propane (149 mg, 0.36 mmol), formic acid (0.6 mL), and triethylamine (3.0 mL) in anhydrous dimethylformamide (40 mL) was stirred at ambient temperature for 4 d. After concentration, the residue was subjected chromatography (silica gel, 1:1 hexane:ethylacetate, 2–10% methanol, 0.1% ammonium hydroxide). Product containing fractions were concentrated, partitioned between methylene chloride (100 mL) and saturated sodium bicarbonate (100 mL), and the aqueous layer extracted with methylene chloride (50 mL). The combined organic extracts were dried (sodium sulfate), concentrated, and the residue purified by chromatography (silica gel, 1:1 hexane:ethylacetate, 2–10% methanol, 0.1% ammonium hydroxide) to give 267 mg (57%) of the title compound as an oil which gave a white, crystalline solid, mp 107° C., upon trituration with ether/hexane: $^1$H NMR (300 MHz, CDCl$_3$) d 7.86 (d, J=7.4 Hz, 1H), 7.40 (m, 1H), 7.1–7.3 (m, 6H), 6.97 (t, J=7.3 Hz, 1H), 6.89 (d, J=8.1 Hz, 1H), 6.84 (d, J=8.6 Hz, 2H), 6.66 (s, 1H), 4.07 (t, J=6.1 Hz, 2H), 2.75 (t, J=6.1 Hz, 2H), 2.49 (m, 4H), 1.5–1.7 (m, 4H), 1.4–1.5 (m, 2H); $^{13}$C NMR (125 MHz, CDCl$_3$) d 159.1, 151.6, 139.3, 137.1, 133.0, 131.5, 129.8, 129.1, 126.8, 124.6, 124.4, 123.7, 122.6, 121.5, 121.5, 119.3, 116.9, 114.6, 77.6, 65.7, 57.7, 54.9, 25.8, 24.0; MS (FD+) m/e 441 (M+); Anal. calc'd for C$_{28}$H$_{27}$NO$_2$S: C, 76.15; H, 6.17; N, 3.17. Found: C, 75.93; H, 6.44; N, 3.01.

solution of 4-(trimethylsilyloxy)phenylmagnesium bromide (prepared from the corresponding bromobenzene and magnesium turnings, catalyzed by iodine in THF, 25.4 mL, 10.16 mmol). The mixture was allowed to warm to room temperature and stirred for 1.5 h. After dilution with ether (250 mL), the mixture was quenched with saturated ammonium chloride (250 mL) and the organic layer was dried (sodium sulfate) and concentrated. The residue was slurried in methanol (100 mL) and ether was added until the mixture was homogeneous. The solution was cooled to 0° C. and treated with anhydrous potassium carbonate (3 g) for 15 min. After dilution with ether (250 mL), the mixture was filtered through Celite, washed with saturated ammonium chloride, and the aqueous layer was extracted with additional ether (100 mL). The combined organic layers were dried (sodium sulfate), concentrated, and the residue purified by chromatography (silica gel, 10:1 hexane:ethyl acetate). Recrystallization from hexane provided 2.6 g (87%) of the title compound as a light pink solid, mp 174°–175° C.: $^1$H NMR (300 MHz) d 8.49 (s, 1H), 7.44 (d, J=2.2 Hz, 1H), 7.3–7.4 (m, 4H), 6.83 (dd, J=8.7, 2.2 Hz, 1H), 6.76 (d, J=8.5 Hz, 2H), 6.65 (s, 1H), 6.50 (dd, J=8.2, 2.3 Hz, 1H), 6.36 (d, J=2.3 Hz, 1H), 0.98 (s, 9H), 0.95 (s, 9H), 0.21 (s, 6H), 0.20 (s, 6H); $^{13}$C NMR (125 MHz) d 158.7, 157.8, 153.9, 153.5, 140.9, 132.7, 131.6, 131.1, 129.9, 126.1, 124.7, 122.7, 119.3, 116.1, 114.4, 114.0, 113.9, 109.3, 78.3, 26.0, 25.9, 18.7, −4.3; IR (CHCl$_3$) 3590, 3310 cm$^{-1}$; MS (FD+) m/e 590 (M+); Anal. cald'd. for C$_{33}$H$_{42}$O$_4$SSi$_2$: C, 67.07; H, 7.16. Found: C, 66.79; H, 7.05.

Preparation 8
3,9-Bis[(tert-butyldimethylsilyl)oxy]-6-[4-[2-(1-pyrrolidinyl)ethoxy]phenyl]-6-H-[1]benzothieno[3,2-c][1]benzopyran

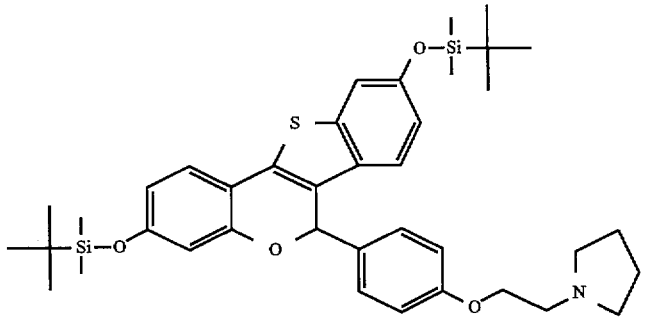

Preparation 7
3,9-Bis[(tert-butyldimethylsilyl)oxy]-6-[4-hydroxyphenyl]-6-H-[1]benzothieno[3,2-c][1]benzopyran

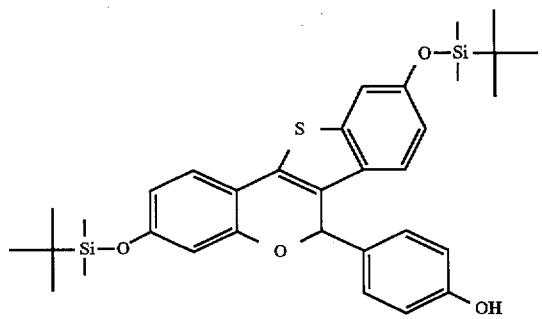

To a solution of the product of Preparation 5 (3.0 g, 5.08 mmol) in toluene (150 mL) at 0° C. was added a 0.4M THF A toluene solution of the product of Preparation 7 (400 mg, 0.68 mmol), triphenylphosphine (708 mg, 2.7 mmol), and 1-(2-hydroxyethyl)pyrrolidine (390 mg, 396 mL, 3.39 mmol) was treated with diethyl azodicarboxylate (DEAD) (470 mg, 425 mL, 2.7 mmol) at room temperature and stirred for 2 h. The mixture was then diluted with ether (100 mL), washed with saturated ammonium chloride (100 mL), and the aqueous layer washed with additional ether (50 mL). The combined organic layers were dried (sodium sulfate), concentrated, and the residual triphenylphosphine oxide precipitated from hexane. The hexane mother liquor was concentrated and the residue purified by chromatography (silica gel, 1:1 hexane:ethyl acetate, 3–5% methanol, 0.1% ammonium hydroxide) to give 359 mg (77%) of the title compound as a colorless oil: $^1$H NMR (300 MHz) d 7.45 (d, J=2.1 Hz, 1H), 7.28 (d, J=8.6 Hz, 2H), 7.22 (m, 2H), 6.85 (d, J=8.6 Hz, 2H), 6.83 (dd, J=8.6, 2.3 Hz, 1H), 6.68 (s, 1H), 6.50 (dd, J=8.3, 2.2 Hz, 1H), 6.36 (d, 2.2 Hz, 1H), 4.03 (t, J=6.0 Hz, 2H), 2.77 (t, J=6.0 Hz, 2H), 2.50 (m, 4H), 1.67 (m, 4H), 0.98 (s, 9H), 0.95 (s, 9H), 0.21 (s, 6H), 0.20 (s, 6H); $^{13}$C NMR (125 MHz) d 160.1, 157.8, 153.9, 153.4, 140.9, 132.7, 132.5, 131.1, 129.8, 125.9, 124.7, 122.6, 119.3, 115.1, 114.4, 114.1, 113.9, 109.4, 78.1, 67.7, 55.2, 54.9, 26.0, 25.9, 24.0, 18.6, −4.3; MS (FD+) m/e 687 (M+); Anal. calc'd. for $C_{39}H_{53}NO_4SSi_2$: C, 68.06; H, 7.78; N, 2.04. Found: C, 67.94; H, 7.61; N, 2.21.

EXAMPLE 8

3,9-Dihydroxy-6-[4-[2-(1-pyrrolidinyl)ethoxy]phenyl]-6-H-[1]benzothieno[3,2-c][1]benzopyran

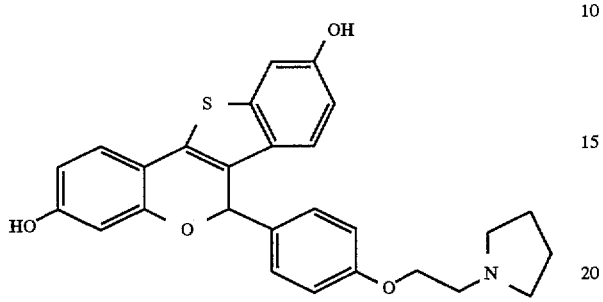

By the procedure described for Example 1, the product of preparation 8 (331 mg, 0.48 mmol) was reacted with 1.0M TBAF in THF (2.4 mmol) to give, after radial chromatography (silica gel, 1:1 hexane:ethyl acetate, 30% methanol, under an ammonia atmosphere) 200 mg (91%) of the title compound as a white solid, mp 237–240 d°C.: $^1$H NMR (300 MHz, dimethylformamide-$d_7$) d 10.05 (br, 2H), 7.45 (d, J=2.0 Hz, 1H), 7.30 (d, J=8.4 Hz, 2H), 7.23 (d, J=8.6 Hz, 1H), 7.19 (d, J=8.2 Hz, 1H), 6.91 (d, J=8.7 Hz, 2H), 6.86 (dd, J=8.9, 2.2 Hz, 1H), 6.74 (s, 1H), 6.51 (dd, J=8.2, 2.1 Hz, 1H), 6.40 (d, J=2.1 Hz, 1H), 4.14 (t, J=5.6 Hz, 2H), 2.96 (t, J=5.5 Hz, 2H), 2.6–2.8 (m, 4H), 1.6–1.8 (m, 4H); $^{13}$C NMR (125 MHz, dimethylformamide-$d_7$) d 160.2, 159.6, 156.4, 153.2, 140.8, 133.0, 130.8, 129.6, 125.2, 124.6, 122.4, 115.3, 115.1, 112.2, 109.7, 108.8, 104.5, 77.6, 66.8, 54.8, 54.7, 23.8; IR (KBr) 3286 cm$^{-1}$; HRMS (FAB+) m/e calc'd. for $C_{27}H_{26}NO_4S$ 460.1583 (MH+), found 460.1572; Anal. calc'd. for $C_{27}H_{25}NO_4S \cdot 0.5H_2O$: C, 69.20; H, 5.60; N, 2.99. Found: C, 69.13; H, 5.31; N, 2.58.

Preparation 9

3,9-Bis[(tert-butyldimethylsilyl)oxy]-6-[4-(2-dimethylaminoethoxy)phenyl]-6-H-[1]benzothieno[3,2-c][1]benzopyran

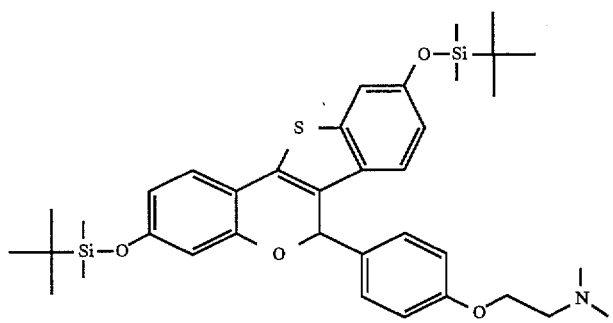

By the method described in Preparation 8, the product of Preparation 7 (450 mg, 0.76 mmol), triphenylphosphine (799 mg, 3.1 mmol), and N,N-dimethylethanolamine (340 mg, 383 mL, 3.81 mmol) were reacted with diethyl azodicarboxylate (DEAD) (531 mg, 480 mL, 3.1 mmol) in toluene (30 mL). Chromatography (silica gel, 1:1 hexane:ethyl acetate, 3% methanol, 0.1% ammonium hydroxide) provided 357 mg (71%) of the title compound as a white foam: $^1$H NMR (300 MHz) d 7.45 (d, J=2.1 Hz, 1H), 7.27 (d, J=8.6 Hz, 2H), 7.24 (m, 2H), 6.83 (m, 3H), 6.67 (s, 1H), 6.50 (dd, J=8.2, 2.2 Hz, 1H), 6.36 (d, 2.2 Hz, 1H), 4.00 (t, J=5.9 Hz, 2H), 2.60 (t, J=5.9 Hz, 2H), 2.20 (s, 6H), 0.98 (s, 9H), 0.95 (s, 9H), 0.21 (s, 6H), 0.20 (s, 6H); $^{13}$C NMR (125 MHz) d 160.1, 157.8, 153.9, 153.4, 141.0, 132.7, 132.6, 131.2, 129.8, 126.0, 124.7, 122.7, 119.4, 115.2, 114.4, 114.1, 113.9, 109.4, 78.1, 67.0, 58.7, 46.0, 26.0, 25.9, 18.6, −4.3; MS (FD+) m/e 661.5 (M+); Anal. calc'd. for $C_{37}H_{51}NO_4SSi_2$: C, 67.11; H, 7.78; N, 2.12. Found: C, 67.38; H, 7.52; N, 2.09.

EXAMPLE 9

3,9-Dihydroxy-6-[4-(2-dimethylaminoethoxy)phenyl]-6-H-[1]benzothieno[3,2-c][1]benzopyran

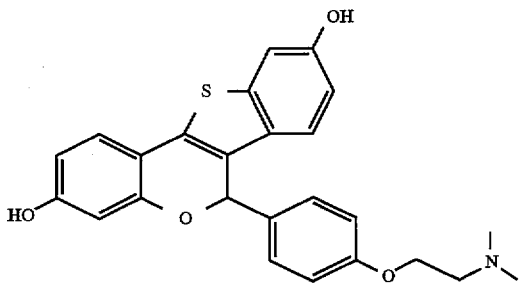

By the procedure described for Example 1, the product of Preparation 9 (328 mg, 0.50 mmol) was reacted with 1.0M TBAF in THF (2.5 mmol) to give, after radial chromatography (silica gel, 1:1 hexane:ethyl acetate, 30% methanol, under an ammonia atmosphere) 212 mg (99%) of the title compound, which crystallized from carbon tetrachloride/acetone as a pink solid, mp 130–140 d°C.: $^1$H NMR (300 MHz) d 7.34 (d, J=2.1 Hz, 1H), 7.25 (d, J=8.6 Hz, 2H), 7.15 (m, 2H), 6.9–7.0 (m, 3H), 6.62 (s, 1H), 6.45 (dd, J=8.3, 2.3 Hz, 1H), 6.34 (d, J=2.2 Hz, 1H), 4.01 (t, J=5.8 Hz; 2H), 2.64 (t, J=5.8 Hz, 2H), 2.30 (s, 6H); $^{13}$C NMR (125 MHz) d 160.0, 159.8, 156.0, 153.5, 141.1, 133.0, 131.0, 131.4, 130.2, 129.8, 125.3, 124.8, 122.6, 115.3, 115.2, 112.7, 109.7, 109.0, 104.8, 78.0, 66.6, 58.6, 45.8; IR (KBr) 3300 cm$^{-1}$; HRMS (FAB+) m/e calc'd. for $C_{25}H_{24}NO_4S$ 434.1426 (MH+), found 434.1440; Anal. calc'd. for $C_{25}H_{23}NO_4S \cdot 0.4CCl_4$: C, 61.62; H, 4.69; N, 2.83. Found: C, 60.93; H, 4.73; N, 2.95.

Preparation 10

3,9-Bis[(tert-butyldimethylsilyl)oxy]-6-[4-[2-(2-oxo-1-pyrrolidinyl)ethoxy]phenyl]-6-H-[1]benzothieno[3,2-c][1]benzopyran

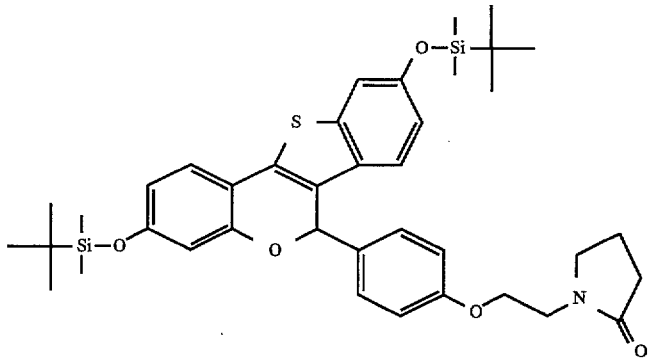

By the method described in Preparation 8, the product of Preparation 7 (450 mg, 0.76 mmol), triphenylphosphine (799 mg, 3.1 mmol), and 1-(2-hydroxyethyl)-2-pyrrolidinone (492 mg, 431 mL, 3.81 mmol) were reacted with diethyl azodicarboxylate (DEAD) (531 mg, 480 mL, 3.1 mmol) in toluene (30 mL). Chromatography (silica gel, 1:1 hexane:ethyl acetate) provided 368 mg (69%) of the title compound as a white foam: $^1$H NMR (300 MHz) d 7.45 (d, J=2.1 Hz, 1H), 7.28 (d, J=8.7 Hz, 2H), 7.23 (d, J=8.2 Hz, 1H), 7.22 (d, J=8.6 Hz, 1H), 6.88 (m, 3H), 6.69 (s, 1H), 6.51 (dd, J=8.5, 2.5 Hz, 1H), 6.36 (d, J=2.3 Hz, 1H), 4.05 (t, J=5.4 Hz, 2H), 3.54 (t, J=5.4 Hz, 2H), 3.46 (t, J=7.0 Hz, 2H), 2.15 (t, J=8.0 Hz, 2H), 1.91 (m, 2H), 0.98 (s, 9H), 0.95 (s, 9H), 0.21 (s, 6H), 0.20 (s, 6H); $^{13}$C NMR (125 MHz) d 175.0, 160.1, 158.1, 154.2, 153.6, 141.2, 133.2, 133.0, 131.4, 130.1, 126.2, 125.0, 122.9, 119.6, 115.5, 114.6, 114.4, 114.2, 109.6, 78.3, 67.0, 48.7, 42.7, 31.2, 26.2, 26.2, 18.9, −4.1; IR (CHCl$_3$) 1673 cm$^{-1}$; HRMS (FAB+) m/e calc'd. for C$_{39}$H$_{51}$NO$_5$SSi$_2$ 701.3027 (M+), found 701.3039.

EXAMPLE 10

3,9-Dihydroxy-6-[4-[2-(2-oxo-1-pyrrolidinyl)ethoxy]phenyl]-6-H-[1]benzothieno[3,2-c][1]benzopyran

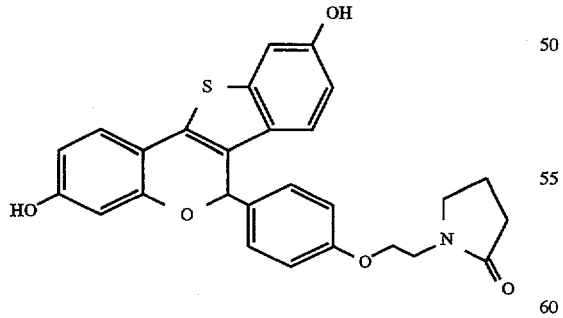

By the procedure described for Example 1, the product of preparation 10 (331 mg, 0.47 mmol) was reacted with 1.0M TBAF in THF (2.4 mmol) to give, after radial chromatography (silica gel, 1:1 hexane:ethyl acetate, 20% methanol, under an ammonia atmosphere) and recrystallization from acetone 161 mg (72%) of the title compound as a red solid, mp 150–160 d°C.: $^1$H NMR (300 MHz, methanol-d$_4$) d 7.21 (m, 3H), 7.11 (d, J=8.3 Hz, 1H), 7.02 (d, J=8.7 Hz, 1H), 6.80 (d, J=8.6 Hz, 2H), 6.71 (dd, J=8.6, 2.2 Hz, 1H), 6.51 (s, 1H), 6.37 (dd, J=8.2, 2.3 Hz, 1H), 6.25 (d, J=2.3 Hz, 1H), 4.04 (t, J=5.2 Hz, 2H), 3.57 (t, J=5.2 Hz, 2H), 3.48 (t, J=7.1 Hz, 2H), 2.28 (t, J=8.1 Hz, 2H), 1.91 (quintet, J=7.5 Hz, 2H); $^{13}$C NMR (125 MHz, methanol-d$_4$) d 178.0, 160.2, 160.0, 156.2, 153.9, 141.7, 133.7, 131.9, 130.9, 130.3, 125.6, 125.0, 122.7, 115.6, 115.4, 113.4, 109.8, 109.0, 104.9, 78.6, 66.6, 43.4, 31.8, 30.7, 18.9; IR (CHCl$_3$) 1680 cm$^{-1}$; MS (FD+) m/e 474 (MH+); Anal. calc'd. for C$_{27}$H$_{23}$NO$_5$S.(CH$_3$)$_2$CO: C, 67.77; H, 5.51; N, 2.64. Found: C, 67.92; H, 5.56; N, 2.59.

Preparation 11

3,9-Bis[(tert-butyldimethylsilyl)oxy]-6-[4-(2-diethylaminoethoxy)phenyl]-6-H-[1]benzothieno[3,2-c][1]benzopyran

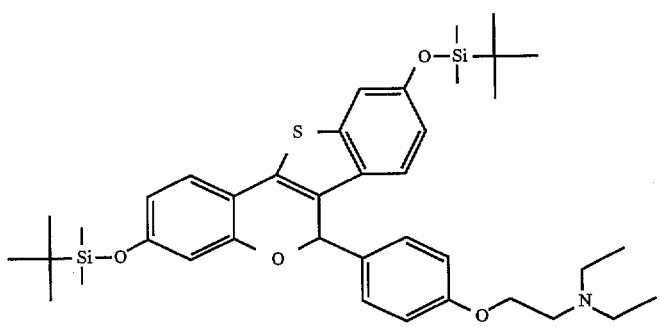

By the method described in Preparation 8, the product of Preparation 7 (500 mg, 0.85 mmol), triphenylphosphine (892 mg, 3.4 mmol), and N,N-diethylethanolamine (496 mg, 438 mL, 4.23 mmol) were reacted with diethyl azodicarboxylate (DEAD) (592 mg, 535 mL, 3.4 mmol) in toluene (35 mL). Chromatography (silica gel, 3:1 hexane:ethyl acetate, 0.1% ammonium hydroxide) provided 540 mg (92%) of the title compound as a colorless oil: $^1$H NMR (300 MHz) d 7.46 (d, J=2.5 Hz, 1H), 7.3–7.4 (m, 4H), 6.86 (m, 3H), 6.69 (s, 1H), 6.51 (dd, J=8.3, 2.3 Hz, 1H), 6.37 (d, 2.2 Hz, 1H), 3.98 (t, J=6.3 Hz, 2H), 2.77 (t, J=6.3 Hz, 2H), 2.54 (q, J=7.1 Hz, 4H), 0.99 (s, 9H), 0.97 (t, J=7.0 Hz, 6H), 0.96 (s, 9H), 0.22 (s, 6H), 0.21 (s, 6H); $^{13}$C NMR (125 MHz) d 160.0, 157.5, 153.7, 153.3, 140.8, 132.6, 132.3, 131.1, 129.7, 125.7, 124.6, 122.5, 119.2, 115.0, 114.2, 113.9, 113.7, 109.3, 78.1, 67.2, 52.3, 48.1, 26.0, 26.0, 18.6, 12.5, –4.3; MS (FD+) m/e 689 (M+);

Preparation 12

3,9-Bis[(tert-butyldimethylsilyl)oxy]-6-[4-[2-(1-morpholinyl)ethoxy]phenyl]-6-H-[1]benzothieno[3,2-c][1]benzopyran

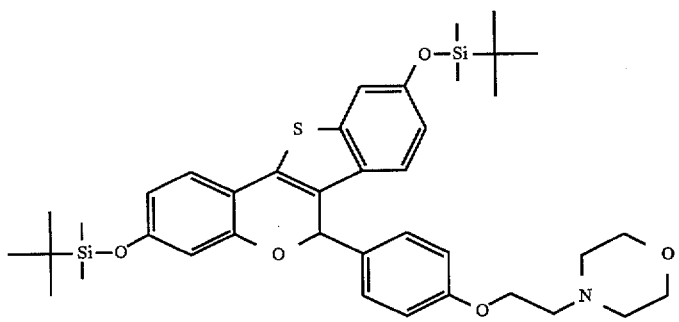

By the method described in Preparation 8, the product of Preparation 7 (500 mg, 0.85 mmol), triphenylphosphine (892 mg, 3.4 mmol), and 1-(2-hydroxyethyl)morpholine (555 mg, 512 mL, 4.23 mmol) were reacted with diethyl azodicarboxylate (DEAD) (592 mg, 535 mL, 3.4 mmol) in toluene (35 mL). Chromatography (silica gel, 3:1 hexane:ethyl acetate, 0.1% ammonium hydroxide) provided 569 mg (95%) of the title compound as a pink foam: $^1$H NMR (300 MHz) d 7.46 (d, J=2.1 Hz, 1H), 7.2–7.3 (m, 4H), 6.86 (m, 3H), 6.70 (s, 1H), 6.51 (dd, J=8.2, 2.3 Hz, 1H), 6.37 (d, 2.7 Hz, 1H), 4.04 (t, J=5.8 Hz, 2H), 3.57 (t, J=4.5 Hz, 2H), 2.69 (t, J=5.7 Hz, 2H), 2.47 (m, 4H), 0.99 (s, 9H), 0.96 (s, 9H), 0.22 (s, 6H), 0.21 (s, 6H); $^{13}$C NMR (125 MHz) d 159.8, 157.6, 153.7, 153.2, 140.8, 132.5, 132.5, 131.1, 129.7, 125.8, 124.6, 122.5, 119.2, 115.1, 114.2, 114.0, 113.8, 109.3, 78.2, 67.0, 66.2, 57.9, 54.6, 26.0, 25.9, 18.6, –4.3; MS (FD+) m/e 703 (M+);

Preparation 13

3,9-Bis[(tert-butyldimethylsilyl)oxy]-6-H-benzofuro[3,2-c][1]benzopyran-6-one

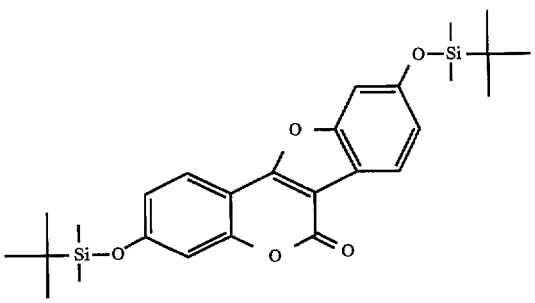

Coumestrol (10 g, 37.3 mmol) was slurried in methylene chloride (600 mL), cooled to 0° C., and treated with triethylamine (24.9 g, 34.3 mL, 246 mmol) and tert-butyldimethylsilyl chloride (24.7 g, 164 mmol). The mixture was warmed to ambient temperature and stirred overnight, during which it slowly became homogeneous. After dilution with ether (800 mL), the mixture was washed with brine (800 mL) and the aqueous layer was extracted with ether (500 mL). The combined organic layers were dried (sodium sulfate), concentrated, and the residue recrystallized from hexane to provide 14.2 g (77%) of the title compound as a white powder, mp 118°–119° C.: $^1$H-NMR (300 MHz, CDCl$_3$) d 7.90 (d, J=8.5 Hz, 1H), 7.82 (d, J=8.5 Hz, 1H), 7.10 (d, J=2.0 Hz, 1H), 6.97 (m, 2H), 6.90 (dd, J=8.5, 2.0 Hz, 1H), 1.03 (s, 9H), 1.02 (s, 9H), 0.28 (s, 6H), 0.25 (s, 6H); IR (CHCl₃) 1733 cm⁻¹; MS (FD+) m/e 496 (M+); Anal. calc'd. for $C_{27}H_{36}O_5Si_2$: C, 65.27; H, 7.32. Found: C, 65.57; H, 7.26.

Preparation 14

3,9-Bis[(tert-butyldimethylsilyl)oxy]-6-H-benzofuro[3,2-c][1]benzopyran-6-ol

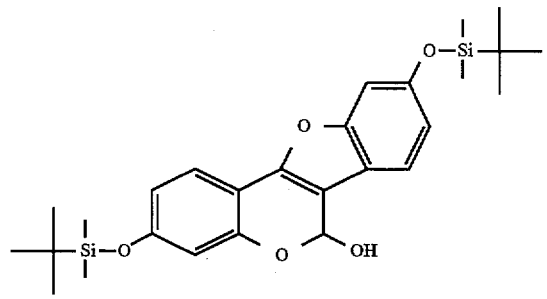

By the method described in Preparation 4, the product of Preparation 13 (5.0 g, 10.0 mmol) was reacted with a 1.0M toluene solution of diisobutylaluminum hydride (12.0 mL, 12.0 mmol) in toluene (450 mL). Recrystallization from hexane gave 1.26 g of the title compound as mixture with its aldehyde tautomer. Chromatography (silica gel, 2–15% ethyl acetate/hexane) of the mother liquor provided 1.37 g of starting material (approximately 67% pure) and, after recrystallization, 580 mg of title compound for a total output of 1.85 g (37%) of the tautomeric mixture: ¹H NMR (300 MHz) d 10.15 (s, 0.5H), 9.2 (br s, 0.5H), 7.99 (d, J=8.4 Hz, 1H), 7.56 (d, J=8.4 Hz, 1H), 7.50 (m, 0.5H), 7.09 (d, J=2.0 Hz, 1H), 6.96 (m, 1H), 6.6–6.7 (m, 2H), 6.55 (m, 0.5H), 1.01 (s, 9H), 1.00 (s, 9H), 0.27 (s, 6H), 0.25 (s, 6H); IR (CHCl₃) 3550, 1663 cm⁻¹; MS (FD) m/e 499 (MH+); Anal. calc'd. for $C_{27}H_{38}O_5Si_2$: C, 65.02; H, 7.69. Found: C, 65.32; H, 7.76.

Preparation 15

3,9-Bis[(tert-butyldimethylsilyl)oxy]-6-phenoxy-6-H-benzofuro[3,2-c][1]benzopyran

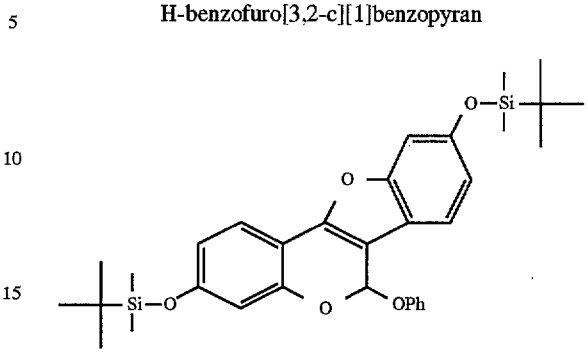

By the method described in Preparation 5, the product of Preparation 14 (464 mg, 0.93 mmol) was reacted with phenol (1.05 g, 11.2 mmol) in chlorobenzene (25 mL) containing anhydrous magnesium sulfate (1.0 g) to yield 467 mg (87%) the crude title compound as an unstable pink foam which was used without purification: ¹H NMR (300 MHz) d 7.1–7.7 (m, 8H) 6.6–6.9 (m, 3H), 1.01 (s, 9H), 1.00 (s, 9H), 0.28 (s, 6H), 0.25 (s, 6H).

Preparation 16

3,9-Bis[(tert-butyldimethylsilyl)oxy]-6-[4-[2-(1-piperidinyl)ethoxy]phenyl]-6-H-benzofuro[3,2-c][1]benzopyran

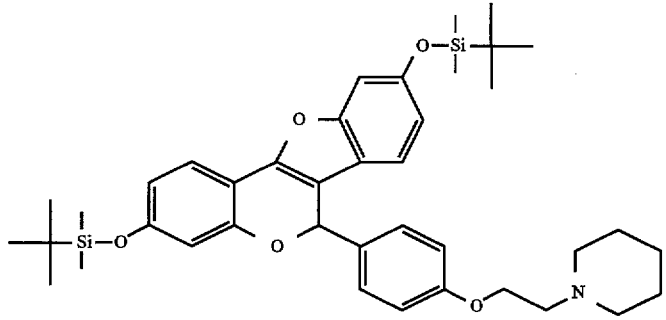

By the method described in Preparation 6, the product of Preparation 15 (467 mg, 0.81 mmol) was reacted with a 0.5M THF solution of 4-[2-(1-piperidinyl)ethoxy]phenylmagnesium bromide (2.6 mL, 1.62 mmol) in toluene (15 mL). Radial chromatography (silica gel, 2:1 hexane-:ethyl acetate, 1% methanol under an ammonia atmosphere) provided 500 mg (90%) of the title compound as a colorless, gummy solid: $^1$H NMR (300 MHz) d 7.39 (m, 3H), 7.04 (d, J=2.0 Hz, 1H), 6.92 (d, J=8.6 Hz, 2H), 6.78 (d, J=8.4 Hz, 1H), 6.68 (d, J=8.1 Hz, 1H), 6.68 (s, 1H), 6.53 (dd, J=8.2, 2.2 Hz, 1H), 6.38 (d, J=2.6 Hz, 1H), 4.05 (t, J=5.9 Hz, 2H), 2.64 (t, J=6.1 Hz, 2H), 2.42 (m, 4H), 1.4–1.6 (m, 4H), 1.3–1.4 (m, 2H), 0.96 (s, 9H), 0.95 (s, 9H), 0.20 (s, 6H), 0.19 (s, 6H); $^{13}$C NMR (125 MHz) d 150.3, 158.0, 156.8, 155.5, 154.0, 148.2, 132.7, 129.8, 121.6, 121.1, 119.8, 117.3, 115.3, 113.8, 110.6, 109.8, 109.1, 103.8, 79.0, 66.9, 58.5, 55.6, 26.8, 26.0, 26.0, 25.0, 18.7, −4.3, −4.3; MS (FD) m/e 686 (M+); Anal. calc'd. for $C_{40}H_{55}NO_5Si_2$: C, 70.03; H, 8.08; N, 2.04. Found: C, 70.28; H, 8.14; N, 2.08.

EXAMPLE 11

3,9-Dihydroxy-6-[4-[2-(1-piperidinyl)ethoxy]phenyl]-6-H-benzofuro[3,2-c][1]benzopyran

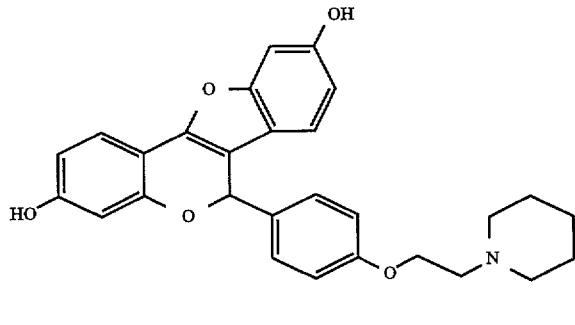

By the procedure described for Example 1, the product of Preparation 16 (520 mg, 0.76 mmol) was reacted with 1.0M TBAF in THF (4.5 mmol) to give, after radial chromatography (silica gel, 1:1 hexane:ethyl acetate, 10% methanol, under an ammonia atmosphere) 292 mg (72%) of the title compound as a bright red foam, which crystallized from carbon tetrachloride: $^1$H NMR (300 MHz, dimethylformamide-d$_7$) d 10.00 (br s, 1H), 9.83 (br s, 1H), 7.3–7.5 (m, 3H), 7.10 (s, 1H), 6.98 (d, J=8.5 Hz, 2H), 6.7–6.9 (m, 3H), 6.54 (dd, J=8.1, 1.8 Hz, 1H), 6.42 (s, 1H), 4.10 (t, J=5.8 Hz, 2H), 2.67 (m, 2H), 2.44 (m, 4H), 1.4–1.6 (m, 4H), 1.3–1.4 (m, 2H); $^{13}$C NMR (125 MHz, dimethylformamide-d$_7$) d 160.2, 159.9, 156.8, 156.4, 155.1, 147.2, 133.0, 129.5, 121.4, 119.5, 118.9, 115.1, 112.9, 109.2, 108.9, 108.3, 104.3, 98.7, 78.5, 66.5, 58.2, 55.3, 26.4, 24.6; IR (KBr) 3220 cm$^{-1}$; HRMS (FAB+) m/e calc'd. for $C_{28}H_{28}NO_5$ 458.1967 (MH+), found 458.1974; Anal. calc'd. for $C_{28}H_{27}NO_4S \cdot 0.25CCl_4$: C, 68.40; H, 5.49; N, 2.82. Found: C, 68.58; H, 5.81; N, 2.94.

Preparation 17

2-Methoxy-8-hydroxy-11,12-dihydro-5H-benzo[b]naphtho[2,1-d]pyran-5-one

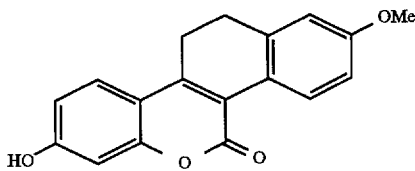

To a solution of 1-carbomethoxy-6-methoxy-2-tetralone (see, Colvin, Martin, and Shroot, *Chemistry and Industry*, 2130 (1966)) (18.0 g, 76.8 mmol) and resorcinol (8.9 g, 80.7 mmol) stirring at ambient temperature in toluene (450 mL) was added phosphorus oxychloride (12.0 g, 7.3 mL, 18.3 mmol) dropwise, and the mixture warmed to 80° C. for 12 h. After cooling to room temperature, the mixture was poured into water (500 mL) and filtered, rinsing the precipitate with ether. The filtrate layers were separated, the aqueous layer was extracted with ethyl acetate (3×500 mL), and the combined organic layers were dried (sodium sulfate) and concentrated. Recrystallization of the residue from methanol provided 16.0 g of the title compound as a yellow solid, mp 244–249 d°C.: $^1$H NMR (300 MHz, DMSO-d$_6$) d 10.55 (br s, 1H), 8.24 (d, J=8.6 Hz, 1H), 7.75 (d, J=8.7 Hz, 1H), 6.6–7.0 (m, 4H), 3.76 (s, 3H), 2.8–3.0 (m, 4H); $^{13}$C NMR (125 MHz, DMSO-d$_6$) d 170.3, 160.3, 158.3, 158.1, 153.3, 147.7, 137.5, 127.4, 125.8, 122.5, 114.5, 112.6, 112.4, 110.9, 101.4, 54.6, 26.3, 22.7; IR (KBr) 3250, 1676, 1618 cm$^{-1}$; MS (FD+) m/e 294 (M+); Anal. calc'd. for $C_{18}H_{14}O_4$: C, 73.45; H, 4.80. Found: C, 73.15; H, 4.86.

Preparation 18

2,8-Bis[(tert-butyldimethylsilyl)oxy]-11,12-dihydro-5H-benzo[b]naphtho[2,1-d]pyran-5-one

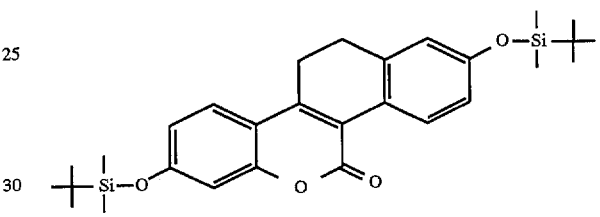

By the procedure described in Preparation 3, the product of Preparation 17 (4.17 g, 14.2 mmol) was reacted with ethanethiol (3.53 g, 3.95 mL, 56.8 mmol) and aluminum chloride (9.0 g, 67.5 mmol) in methylene chloride (100 mL). The crude product was further reacted with triethylamine (8.6 g, 11.9 mL, 85.2 mmol) and tert-butyldimethylsilyl chloride (8.6 g, 56.8 mmol) in methylene chloride (100 mL) to provide, after recrystallization from hexane, the title product as a yellow solid, mp 145°–147° C.: $^1$H NMR (300 MHz, CDCl$_3$) d 8.37 (d, J=8.6 Hz, 1H), 7.58 (d, J=9.3 Hz, 1H), 6.83 (s, 1H), 6.81 (m, 2H), 6.72 (d, J=2.4 Hz, 1H), 2.8–3.0 (m, 4H), 1.00 (s, 18H), 0.27 (s, 6H), 0.24 (s, 6H); $^{13}$C NMR (125 MHz, CDCl$_3$) d 159.8, 158.6, 155.4, 153.9, 147.1, 137.7, 128.6, 125.0, 123.9, 119.0, 118.1, 117.5, 117.3, 113.8, 107.5, 27.4, 25.7, 25.6, 23.9, 18.3, 18.2, −4.3, −4.4; IR (CHCl$_3$) 1708, 1612 cm$^{-1}$; MS (FD) m/e 508 (M+).

Preparation 19

6-Methoxy-1-[(4-hydroxy)phenyl]imino-1,2,3,4-tetrahydronaphthalene

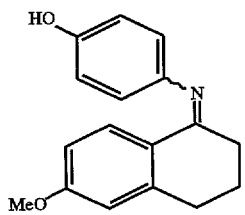

A mixture of 6-methoxytetralone (25 g, 142 mmol) and 4-hydroxyaniline (16.3 g, 149 mmol) was heated to 180° C.

under a nitrogen stream for 2 h. After cooling to ambient temperature, the solid mass was recrystallized from toluene/methanol: $^1$H NMR (300 MHz) d 8.15 (d, J=9.7 Hz, 1H), 6.5–7.9 (m, 6H), 3.80 (s, 3H), 2.84 (t, J=7.3 Hz, 2H), 2.51 (t, J=6.8 Hz, 2H), 1.85 (m, 2H).

Preparation 20

6-Methoxy-1-[(4-hydroxy)phenyl]imino-1,2,3,4-tetrahydronaphthalene

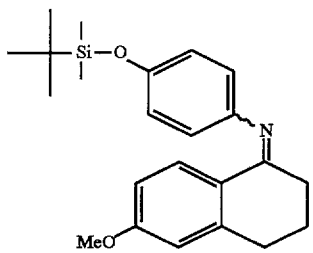

The product of Preparation 19 (36 g, 134.7 mmol) was dissolved in 1:1 methylene chloride:THF (300 mL) and treated with triethylamine (28.6 g, 39.4 mL, 283 mmol) and tert-butyldimethylsilyl chloride (30.5 g, 202 mmol). The mixture was stirred overnight and additional portions of triethylamine (6.8 g, 9.4 mL, 67 mmol) and tert-butyldimethylsilyl chloride (10.2 g, 67 mmol) were added to drive the reaction to completion. After 5 h, the mixture was diluted with ether (500 mL), filtered, concentrated, and the residue washed with hexane/ether. The extracts were filtered, concentrated, and the residue purified by rapid chromatography (silica gel, 18:1–10:1 hexane:ethylacetate) to give 21.0 g (41%) of the title compound as light yellow foam: $^1$H NMR (300 MHz, CDCl$_3$) d 8.32 (d, J=9.7 Hz, 1H), 6.86 (m, 3H), 6.73 (m, 3H), 3.92 (t, J=5.8 Hz, 2H), 2.57 (t, J=6.8 Hz, 2H), 1.96 (m, 2H), 1.05 (s, 9H), 0.26 (s, 6H).

Preparation 21

6-Methoxy-1-[N-[[4-(tert-butyldimethylsilyl)oxy]phenyl]-N-(2,5-dimethoxybenzoyl)]amino-3,4-dihydronaphthalene

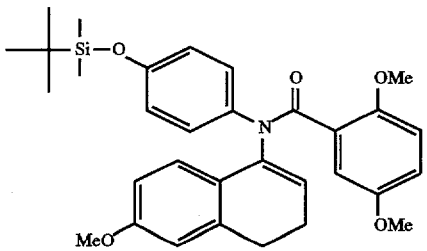

The product of Preparation 20 (10.2 g, 26.8 mmol) was dissolved in methylene chloride (100 mL), cooled to 0° C., and treated with triethylamine (3.8 g, 5.2 mL, 37.5 mmol) followed by a solution of 2,5-dimethoxybenzoylchloride (6.72 g, 33.5 mmol) in dichloromethane (25 mL). The mixture was warmed to reflux overnight, then treated with additional triethylamine (1.4 g, 1.9 mL, 13.4 mmol) and acid chloride (2.7 g, 13.4 mmol) and heating continued for an additional 12 h. After concentration in vacuo, the residue was dissolved in ether (250 mL), washed with brine (250 mL), dried (sodium sulfate), and concentrated. Purification of the residue by chromatography (silica gel, 9:1–4:1 hexane:ethyl acetate) provided 10.3 g of the title compound as a white foam: $^1$H NMR (300 MHz, CDCl$_3$) d 6.4–7.6 (br m, 11H), 5.83 (br s, 1H), 3.4–3.8 (br m, 9H), 1.9–3.0 (br m, 4H), 0.95 (2 br s, 9H), 0.14 (2 br s, 6H); IR (CHCl$_3$) 1651, 1607, 1507 cm$^{-1}$; MS (FD) m/e 545 (M+); Anal. calc'd for C$_{32}$H$_{39}$NO$_5$Si: C, 70.43; H, 7.20; N, 2.57. Found: C, 70.53; H, 7.26; N, 2.76.

Preparation 22

2,8-Dimethoxy-5-[4-[(tert-butyldimethylsilyl)oxy]phenyl]-11,12-dihydro-6H-benzo[c]phenanthrid-6-one

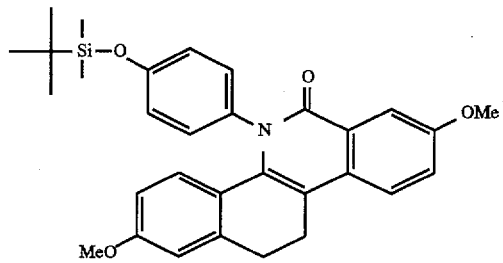

A solution of the product of Preparation 21 (2.73 g, 5 mmol) in benzene (250 mL) was degassed via 3 freeze/pump/thaw cycles and irradiated with a 450 Watt internal mercury lamp in a quartz immersion well under nitrogen. After 22 h, the mixture was concentrated and the residue purified by chromatography (silica gel, 20:1 toluene:ether) to provide 675 mg (26%) of the title compound as a yellow foam. An analytical sample was obtained by crystallization from hexane/ether as light yellow crystals, mp 194°–95° C.: $^1$H NMR (300 MHz, CDCl$_3$) 7.94 (d, 2.8 Hz, 1H), 7.73 (d, 8.9 Hz, 1H), 7.32 (dd, J=8.9, 2.8 Hz, 1H), 7.17 (d, J=8.7 Hz, 2H), 6.84 (d, J=8.7 Hz, 2H), 6.76 (d, J=2.6 Hz, 1H), 6.67, (d, J=8.8 Hz, 1H), 6.35 (dd, J=8.8, 2.7 Hz, 1H), 3.94 (s, 3H), 3.75 (s, 3H), 2.90 (s, 4H), 0.99 (s, 9H), 0.21 (s, 6H); $^{13}$C NMR (125 MHz, CDCl$_3$) d 162.6, 158.3, 157.7, 154.4, 139.7, 134.3, 133.6, 129.9, 129.8, 128.1, 126.2, 123.7, 123.2, 122.6, 119.8, 114.9, 112.7, 110.4, 108.6, 55.3, 54.8, 29.3, 25.5, 23.5, 18.1, −4.4; IR (CHCl$_3$) 1640, 1615, 1507 cm$^{-1}$; MS (FD+) m/e 513 (M+); Anal. calc'd for C$_{31}$H$_{35}$NO$_4$Si: C, 72.48; H, 6.87; N, 2.73. Found: C, 72.66; H, 6.95; N, 2.86.

Preparation 23

2,8-Dimethoxy-5-(4-hydroxyphenyl)-11,12-dihydro-6H-benzo[c]phenanthrid-6-one

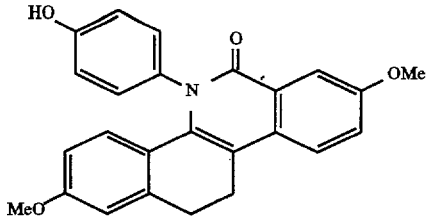

The product of Preparation 22 (790 mg, 1.5 mmol) was dissolved in 3:2 acetonitrile:methylene chloride (50 mL) and treated with hydrogen fluoride-pyridine (10 mL) in 2 portions at 1 h intervals. After further stirring for 1 h, the mixture was diluted with THF (100 ml) and filtered, washing with methanol and ether. The filtrates were diluted with THF (200 mL) and washed with brine (200 mL) and saturated sodium bicarbonate (200 mL). The combined aqueous layers were extracted with THF (100 mL) and the combined organic layers were dried sodium sulfate) and concentrated to provide 340 mg (57%) of a yellow powder, mp 250–275 d°C., which was used without purification: $^1$H NMR (300 MHz, dimethylformamide-$d_7$) d 9.80 (br s, 1H), 7.91 (d, J=9.7 Hz, 1H), 7.81 (d, J=1.9 Hz, 1H), 7.44 (dd, J=9.7, 1.9 Hz, 1H), 7.20 (d, J=8.7 Hz, 2H), 6.8–7.0 (m, 4H), 6.47 (dd, J=8.7, 1.9 Hz, 1H), 3.94 (s, 3H), 3.74 (s, 3H), 2.89 (m, 4H); MS (FD+) m/e 399 (M+).

EXAMPLE 12

2,8-Dimethoxy-5-[4-[2-(1-piperidinyl)ethoxy]phenyl]-11,12-dihydro-6H-benzo[c]phenanthrid-6-one

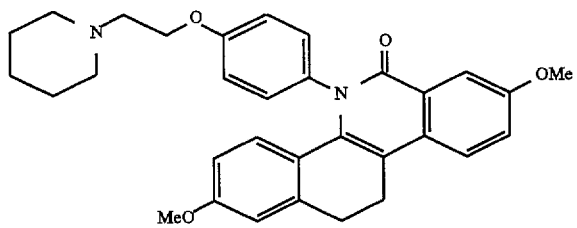

To a solution of the product of Preparation 23 (340 mg, 0.85 mmol), triphenylphosphine (446 mg, 1.7 mmol), and 1-(2-hydroxyethyl)piperidine (275 mg, 282 mL, 2.1 mmol) in THF (20 mL) was added diethyl azodicarboxylate (DEAD) (296 mg, 268 mL, 1.7 mmol) and the mixture was stirred at ambient temperature overnight. After concentration in vacuo, chromatography (silica gel, 1:1 hexane:ethyl acetate, 5–20% methanol, 0.1% ammonium hydroxide) provided 338 mg (66%) of the title compound as a yellow foam: $^1$H NMR (300 MHz) d 7.82 (m, 2H), 7.35 (dd, J=9.7, 2.9 Hz, 1H), 7.23 (d, J=9.7 Hz, 2H), 6.91 (d, J=9.7 Hz, 2H), 6.82 (m, 1H), 6.70 (d, J=9.7 Hz, 1H), 6.38 (dd, J=9.7, 1.9 Hz, 1H), 4.12 (t, J=5.8 Hz, 2H), 3.90 (s, 3H), 3.70 (s, 3H), 2.86 (m, 6H), 2.65 (m, 4H), 1.5–1.7 (m, 4H), 1.4–1.5 (m, 2H).

EXAMPLE 13

2,8-Dimethoxy-5-[4-[2-(1-piperidinyl)ethoxy]phenyl]-6H-benzo[c]phenanthridine

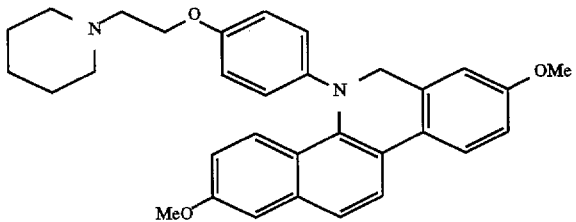

A solution of the product of Example 12 (753 mg, 1.47 mmol) was dissolved in dichloroethane (20 mL), treated with DDQ (352 mg, 1.55 mmol), and warmed to 80° C. After several hours, the mixture was cooled to ambient temperature, diluted with methylene chloride (100 mL), washed with saturated sodium carbonate, and the organic layer dried (sodium sulfate) and concentrated. The residue was purified via chromatography (silica gel, 1:1 hexane::ethyl acetate, 15% methanol) to give 330 mg (44%) of a yellow solid.

The solid obtained above (309 mg, 0.61 mmol) was dissolved in THF (25 mL) and treated with lithium aluminum hydride (LAH) (115 mg, 3.05 mmol) at ambient temperature. After 10 min, excess LAH was quenched with ethyl acetate (50 mL) and the mixture was washed with saturated ammonium chloride (25 mL). The aqueous layer was washed with ethyl acetate (25 mL) and the combined organic layers were washed with brine (25 mL), dried (sodium sulfate), concentrated, and subjected to radial chromatography (silica gel, 1:1 hexane:ethyl acetate, 5% methanol, under an ammonia atmosphere). The product was then dissolved in glacial acetic acid (10 mL) and treated with sodium borohydride (69 mg, 1.82 mmol). After 1 h, the mixture was quenched with saturated sodium bicarbonate and partitioned between methylene chloride and saturated sodium bicarbonate. The organic layer was dried (sodium sulfate), concentrated, and the residue used without further purification: $^1$H NMR (300 MHz) d 7.99 (d, J=8.6 Hz, 1H), 7.82 (d, J=8.6 Hz, 1H), 7.74 (d, J=9.4 Hz, 1H), 7.71 (d, J=8.4 Hz, 1H), 7.28 (d, J=2.3 Hz, 1H), 6.92 (m, 2H), 6.81 (d, J=2.3 Hz, 1H), 6.69 (d, J=9.2 Hz, 2H), 6.63 (d, J=9.1, 2H), 3.89 (t, J=6.2 Hz, 2H), 3.87 (s, 3H), 3.75 (s, 3H), 2.57 (t, J=6.1 Hz, 2H), 2.39 (m, 4H), 1.4–1.5 (m, 4H), 1.3–1.4 (m, 2H).

EXAMPLE 14

2,8-Dihydroxy-5-[4-[2-(1-piperidinyl)ethoxy]phenyl]-6H-benzo[c]phenanthridine

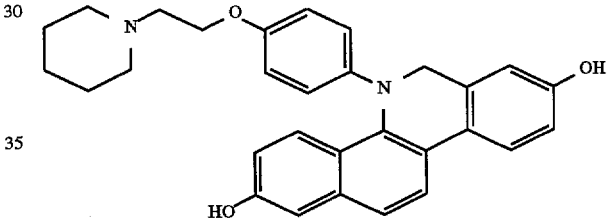

A solution of the product of Example 13 (195 mg, 0.39 mmol) in methylene chloride (25 mL) was treated with ethanethiol (200 mg, 220 mL, 3.2 mmol) and aluminum chloride (320 mg, 2.4 mmol). After stirring for 4 h at ambient temperature, the mixture was quenched carefully with THF (25 mL) and saturated sodium bicarbonate (25 mL). The layers were separated, the aqueous layer was extracted with THF (25 mL), and the combined organic layers were dried (sodium sulfate) and concentrated. The residue was purified by radial chromatography (silica gel, 1:1 hexane:ethyl acetate, 10–20% methanol, under an ammonia atmosphere) to provide 110 mg (60%) of the title compound as a tan foam. An analytical sample was crystallized from methanol as a light red solid: $^1$H NMR (300 MHz, dimethylformamide-$d_7$) d 9.92 (br s, 1H), 9.74 (br s, 1H), 7.99 (d, J=8.8 Hz, 1H), 7.78 (d, J=8.5 Hz, 1H), 7.69 (d, J=9.0 Hz, 1H), 7.63 (d, J=8.7 Hz, 1H), 7.23 (d, J=2.0 Hz, 1H), 6.98 (dd, J=9.0, 2.1 Hz, 1H), 6.84 (dd, J=8.4, 2.1 Hz, 1H), 6.73 (m, 5H), 3.92 (t, J=5.9 Hz, 2H), 2.57 (t, J=5.9 Hz, 2H), 2.38 (m, 4H), 1.4–1.5 (m, 4H), 1.3–1.4 (m, 2H); IR (KBr) 3560, 3490 cm$^{-1}$; MS (FD+) m/e 466 (M+); Anal. calc'd. for $C_{30}H_{30}N_2O_3 \cdot 0.5H_2O$: C, 75.75; H, 6.58; N, 5.89. Found: C, 75.82; H, 6.76; N, 5.95.

EXAMPLE 15

8-dihydroxy-5-[4-[2-(1-piperidinyl)-ethoxy]phenyl]-5H-benzo[b]naphtho[2,1-d]pyran This compound is prepared in accordance with the foregoing teaching and examples.

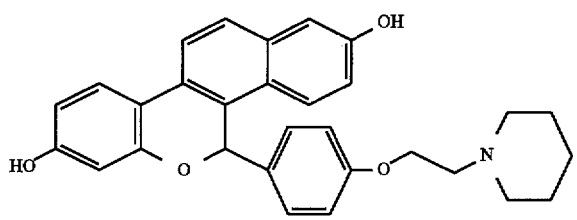

EXAMPLE 10a 3,9-Dihydroxy-6-[4-(2-diethylaminoethoxy)phenyl]-6-H-[1]benzothieno[3,2-c][1]benzopyran

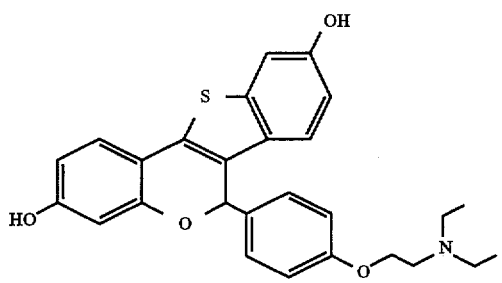

By the procedure described for Example 1, the product of preparation 11 (458 mg, 0.66 mmol) was reacted with 1.0M TBAF in THF (3.3 mmol) to give, after radial chromatography (silica gel, 1:1 hexane:ethyl acetate, 10–20% methanol, under an ammonia atmosphere) and crystallization from acetone/ether 296 mg (72%) of the title compound as a red solid, mp 118–123 d°C.: $^1$H NMR (300 MHz) δ7.35 (d, J=2.1 Hz, 1H), 7.26 (d, J=8.6 Hz, 2H), 7.16 (d, J=8.1 Hz, 1H), 7.13 (d, J=8.5 Hz, 1H), 6.81 (m, 3H), 6.62 (s, 1H), 6.45 (dd, J=8.3, 2.3 Hz, 1H), 6.35 (d, J=2.2 Hz, 1H), 3.98 (t, J=6.2 Hz, 2H), 2.78 (t, J=6.2 Hz, 2H), 2.56 (q, J=7.1 Hz, 4H), 0.97 (t, J=7.1 Hz, 6H); $^{13}$C NMR (75 MHz) δ160.2, 159.7, 155.9, 153.5, 141.1, 132.9, 131.5, 130.2, 129.9, 125.4, 124.8, 122.7, 115.2, 112.8, 109.6, 108.9, 104.8, 78.1, 67.5, 52.6, 48.3, 12.4; IR (KBr) 3311 cm$^{-1}$; MS (FD+) m/e 462 (MH+); Anal. calc'd. for $C_{27}H_{27}NO_4S$: C, 70.04; H, 6.13; N, 3.04. Found: C, 70.26; H, 5.90; N, 3.03.

EXAMPLE 10b 3,9-Dihydroxy-6-[4-[2-(1-morpholinyl)ethoxy]phenyl]-6-H-[1]benzothieno[3,2-c][1]benzopyran

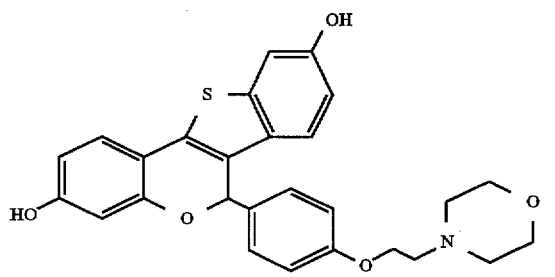

By the procedure described for Example 1, the product of Preparation 12 (521 mg, 0.74 mmol) was reacted with 1.0M TBAF in THF (3.7 mmol) to give, after radial chromatography (silica gel, 1:1 hexane:ethyl acetate, 15% methanol, under an ammonia atmosphere) and crystallization from acetone/ether 286 mg (81%) of the title compound as a red solid, mp 147–153 d°C.: $^1$H NMR (300 MHz) δ7.35 (d, J=2.1 Hz, 1H); 7.25 (d, J=8.6 Hz, 2H), 7.16 (d, J=8.3 Hz, 1H), 7.14 (d, J=8.6 Hz, 1H), 6.81 (m, 3H), 6.62 (s, 1H), 6.46 (dd, J=8.2, 2.2 Hz, 1H), 6.35 (d, J=2.2 Hz, 1H), 4.04 (t, J=5.7 Hz, 2H), 3.56 (t, J=4.7 Hz, 4H), 2.68 (t, J=5.7 Hz, 2H), 2.47 (t, J=4.3 Hz, 4H); $^{13}$C NMR (75 MHz) δ160.0, 159.7, 155.9, 153.5, 141.1, 132.9, 131.4, 129.8, 129.7, 125.4, 124.8, 122.6, 115.2, 112.8, 109.6, 108.9, 104.7, 78.0, 67.2, 66.5, 58.1, 54.7; IR (KBr) 3471 cm$^{-1}$; MS (FD+) m/e 475 (MH+); Anal. calc'd. for $C_{27}H_{25}NO_5S \cdot 0.25H_2O$: C, 67.54; H, 5.36; N, 2.92. Found: C, 67.58; H, 5.51; N, 2.57.

Preparation 12a 6a,11a-Dihydro-9-methoxy-6-H-[1]benzothieno[3,2-c][1]benzopyran-6-one

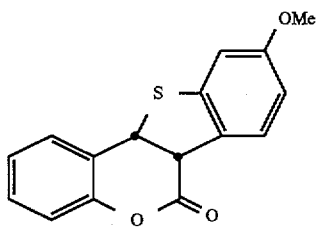

To a stirred solution of 6-methoxythianaphthen-2-one (52.6 g, 290 mmol) in a mixture of ethanol (260 mL) and methylene chloride (130 mL) was added triethylamine (2.0 mL, 14.8 mmol) followed by salicylaldehyde (32 mL, 300 mmol) at room temperature. After 1 h, a solid began to precipitate and stirring was continued for 3.5 h. The mixture was then diluted with cold hexane and filtered to yield 68.3 g (83%) of the title product as a powdery white solid, pure by $^1$H-NMR analysis: $^1$H NMR (300 MHz, CDCl$_3$) δ7.45 (d, J=7.5 Hz, 1H), 7.33 (m, 2H), 7.17 (m, 1H), 7.07 (d, J=8.1 Hz, 1H), 6.77 (d, J=2.4 Hz, 1H), 6.69 (dd, J=2.4, 8.5 Hz, 1H), 5.25 (d, J=7.4 Hz, 1H), 4.37 (d, J=7.3 Hz, 1H), 3.77 (s, 3H); $^{13}$C NMR (75 MHz, CDCl$_3$) δ166.4, 160.7, 150.8, 141.4, 130.1, 129.0, 127.7, 127.0, 124.9, 119.5, 117.2, 111.2, 108.3, 55.5, 50.6, 49.6; IR (CHCl$_3$) 1766 cm$^{-1}$; MS (FD) m/e 284 (M$^+$); Anal. calc'd. for $C_{16}H_{12}O_3S$: C, 67.59; H, 4.26. Found: C, 67.77; H, 4.24.

Preparation 12b

9-Methoxy-6-H-[1]benzothieno[3,2-c][1]benzopyran-6-one

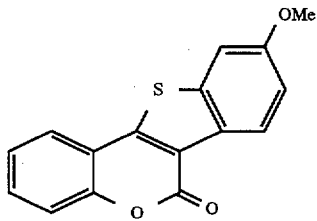

A mixture of the product of Preparation 12a (14.0 g, 49 mmol) and 2,3-dichloro-5,6-dicyano-1,4-benzoquinone (DDQ) (11.6 g, 51 mmol) in dichloroethane (350 mL) was heated briefly to reflux, inducing the formation of a precipitate. The mixture was filtered hot, rinsing the precipitate with methylene chloride, and the mother liquor concentrated in vacuo. The crude product was then rinsed several times with acetone and dried in vacuo to provide 12.6 g (91%) of the title product as a white fluffy solid: $^1$H NMR (300 MHz, CDCl$_3$) δ8.55 (d, J=8.9 Hz, 1H), 7.70 (dd, J=1.2, 8.0 Hz, 1H), 7.4–7.6 (m, 2H), 7.33 (m, 2H), 7.13 (dd, J=2.3, 8.9 Hz, 1H), 3.91 (s, 3H); IR (CHCl$_3$) 1722 cm$^{-1}$; MS (FD) m/e 282 (M$^+$); Anal. calc'd for C$_{16}$H$_{10}$O$_3$S: C, 68.07; H, 3.57. Found: C, 67.80; H, 3.53.

Preparation 12c 9-(t-Butyldimethylsilyl)oxy-6-H-[1]benzothieno[3,2-c][1]benzopyran-6-one

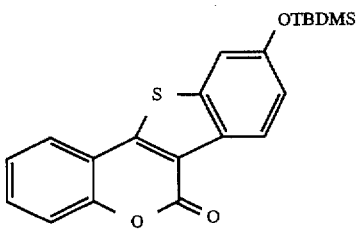

To a mechanically stirred slurry of the product of Preparation 12b (9.0 g, 32 mmol) in methylene chloride (235 mL) was added ethanethiol (5.9 mL, 80 mmol) followed by aluminum chloride (15.8 g, 120 mmol), portionwise. The reaction mixture was stirred at ambient temperature for 1 h, then cooled to 0° C. and quenched cautiously with tetrahydrofuran (THF) followed by saturated sodium bicarbonate. The mixture was diluted with THF, the layers separated, and the aqueous layer was washed several times with THF. The combined organic layers were dried (sodium sulfate) and concentrated to yield 7.4 g (86%) of crude phenol as an off-white, slightly pink solid, which was used without further purification.

The crude product was slurried in methylene chloride (200 mL) and treated with triethylamine (19.1 mL, 140 mmol) and tert-butyldimethylsilyl chloride (10.4 g, 69 mmol). The mixture was stirred at ambient temperature overnight, during which it became homogeneous. After dilution with hexane, the mixture was washed two times with brine. The organic layer was dried (sodium sulfate), concentrated, and the residue recrystallized from hexane to provide 9.8 g (80%) of the title compound as a fluffy white solid: $^1$H NMR (300 MHz, CDCl$_3$) δ8.55 (d, J=8.5 Hz, 1H), 7.72 (d, J=8.7 Hz, 1H), 7.4–7.6 (m, 2H), 7.34 (m, 2H), 7.08 (dd, J=2.2, 8.8 Hz, 1H), 1.02 (s, 9H), 0.26 (s, 6H); IR (CHCl$_3$) 1717 cm$^{-1}$; MS (FD) m/e 382 (M$^+$); Anal. calc'd for C$_{21}$H$_{22}$O$_3$SSi: C, 65.93; H, 5.80. Found: C, 66.23; H, 5.84.

Preparation 12d 9-(t-Butyldimethylsilyl)oxy-6-H-[1]benzothieno[3,2-c][1]benzopyran-6-ol

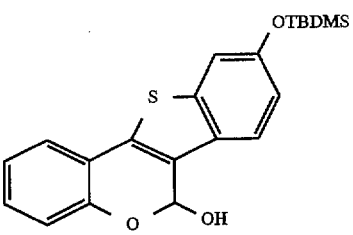

A solution of the product from Preparation 12c (3.5 g, 9.1 mmol) in toluene (490 mL) was cooled to –78° C. and treated dropwise with a 1.0M toluene solution of diisobutylaluminum hydride (11.0 mL, 11 mmol) at a rate maintaining the internal temperature below –70° C. The mixture was stirred for approximately 4 h, then quenched with methanol (14 mL), 10% aqueous citric acid (140 mL), and water (315 mL). The aqueous layer was extracted three times with methylene chloride (560 mL). The organic layers were dried (sodium sulfate), concentrated, and the remnant chromatographed (silica gel, gradient of 2% ethyl acetate in hexane to 20% ethyl acetate in hexane) to yield 1.7 g (49%) of the title compound as a white crystalline solid: $^1$H NMR (300 MHz) δ7.77 (d, J=8.6 Hz, 1H), 7.50 (d, J=2.1 Hz, 1H), 7.42 (m, 1H), 7.28 (m, 1H), 7.05 (m, 2H), 6.89 (m, 1H), 6.46 (m, 1H), 1.02 (s, 9H), 0.26 (s, 6H); IR (CHCl$_3$) 2959, 2932, 2861, 1612, 1598 cm$^{-1}$; MS (FD) m/e 384 (M$^+$); Anal. calc'd for C$_{21}$H$_{24}$O$_3$SSi: C, 65.59; H, 6.29. Found: C, 65.51; H, 6.32.

Preparation 12e 9-(t-Butyldimethylsilyl)oxy-6-phenoxy-6-H-[1]benzothieno[3,2-c][1]benzopyran

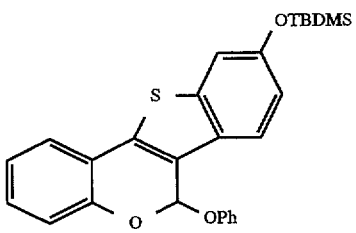

The product of Preparation 12d (1.5 g, 3.9 mmol) and phenol (2.7 g, 29 mmol) were dissolved in chlorobenzene (50 mL) and the mixture was stirred for 3.5 h at reflux. The mixture was concentrated and residue redissolved in chlorobenzene and reconcentrated in vacuo at approximately 70° C. The residue was then dissolved in diethyl ether, washed three times with saturated sodium carbonate, water and brine. The organic layer was dried (sodium sulfate) and concentrated to yield 1.7 g (93%) of the title compound as a fluffy white solid which was used without further purification: the $^1$H NMR spectrum (300 MHz) was consistent with the structure.

EXAMPLE 10c

9-Hydroxy-6-[4-[2-(1-piperidinyl)ethoxy]phenyl]-6-H-[1]benzothieno[3,2-c][1]benzopyran

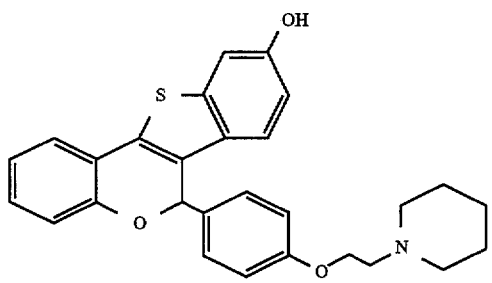

To a solution of the product of Preparation 12e (1.7 g, 3.6 mmol) in toluene (50 mL) at 0° C. was added a 0.2M THF solution of 4-[2-(1-piperidinyl)ethoxy]phenylmagnesium bromide (prepared from the corresponding bromobenzene and magnesium turnings, catalyzed by iodine in THF, 45.3 mL, 9.1 mmol). The mixture was allowed to warm to room temperature and stirred for 14 h. After quenching with water, the mixture was extracted three times with methylene chloride, and the organic layer was dried (sodium sulfate) and concentrated. The remnant was purified via chromatography (silica gel, hexane-4:1 hexane:ethyl acetate) to give 2.6 g (126%) of the partially purified silylated product.

To a solution of the partially purified product (2.6 g, 3.6 mmol) in THF (40 mL), was added a 1.0M THF solution of tetra-n-butylammonium fluoride (TBAF) (5.0 mL, 5.0 mmol). The solution was stirred at ambient temperature for 10 min, then diluted with ethyl acetate and washed five times with saturated sodium bicarbonate and brine. The organic layers were dried (sodium sulfate) and concentrated. The remnant was purified via chromatography (silica gel, 1:1 hexane:ethyl acetate, 0–10% methanol, 0.1% ammonium hydroxide) to give 0.93 g (56%) of the title compound as white fluffy solid: $^1$H NMR (300 MHz) $\delta$6.7–7.4 (m, 12H), 4.02 (t, J=6.0 Hz, 2H), 2.63 (t, J=6.0 Hz, 2H), 2.41 (m, 4H), 1.49 (m, 4H), 1.37 (m, 2H); IR (KBr) 2934, 1609 cm$^{-1}$; MS (FD) m/e 457 (M$^+$); HRMS (FAB) m/e calc'd for $C_{28}H_{28}NO_3S$ (MH+): 458.1790. Found: 458.1798; Anal. calc'd for $C_{28}H_{27}NO_3S \cdot 0.5H_2O$: C, 72.08; H, 6.05; N, 3.00. Found: C, 71.97; H, 6.04; N, 3.06.

Preparation 12f 3-(t-Butyldimethylsilyl)oxy-6-H-[1]benzothieno[3,2-c][1]benzopyran-6-one

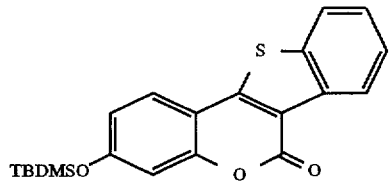

To a mechanically stirred slurry of 3-Methoxy-6-H-[1]benzothieno[3,2-c][1]benzopyran-6-one (*Journal of Organic Chemistry*, 40: 3169 (1975)) (1.0 g, 3.6 mmol) in methylene chloride (30 mL) was added ethanethiol (1.4 mL, 18.0 mmol) followed by aluminum chloride (1.6 g, 12 mmol), portionwise. The reaction mixture was stirred at ambient temperature for 1.5 h, then cooled to 0° C. and quenched cautiously with tetrahydrofuran (THF) followed by saturated sodium bicarbonate. The mixture was diluted with THF, the layers separated, and the aqueous layer was washed several times with THF. The combined organic layers were dried (sodium sulfate) and concentrated to yield the crude phenol, which was used without further purification.

The crude product was slurried in methylene chloride (30 mL) and treated with triethylamine (2.5 mL, 18 mmol) and tert-butyldimethylsilyl chloride (1.3 g, 9.0 mmol). The mixture was stirred at ambient temperature overnight, during which it became homogeneous. After dilution with hexane, the mixture was washed two times with brine. The organic layer was dried (sodium sulfate), concentrated, and the residue purified by chromatography (silica gel, hexane-4:1 hexane:ethyl acetate) to provide 0.95 g (69%) of the title compound as a fluffy white solid: $^1$H NMR (300 MHz, acetone-d$_6$) $\delta$8.57 (d, J=7.8 Hz, 1H), 8.10 (d, J=8.0 Hz, 1H), 7.81 (d, J=8.2 Hz, 1H), 7.5–7.7 (m, 2H), 6.99 (m, 2H), 1.03 (s, 9H), 0.33 (s, 6H); IR (CHCl$_3$) 1716 cm$^{-1}$; MS (FD) m/e 382 (M$^+$); Anal. calc'd for $C_{21}H_{22}O_3SSi$: C, 65.93; H, 5.80. Found: C, 66.11; H, 5.83.

Preparation 12g 3-(t-Butyldimethylsilyl)oxy-6-H-[1]benzothieno[3,2-c][1]benzopyran-6-ol

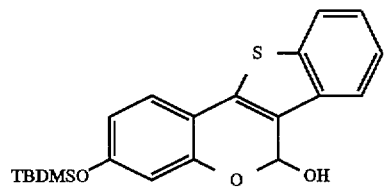

A solution of the product from Preparation 12f (5.0 g, 13 mmol) in toluene (700 mL) was cooled to −78° C. and treated dropwise with a 1.0M toluene solution of diisobutylaluminum hydride (15.7 mL, 15.7 mmol) at a rate maintaining the internal temperature below −70° C. The mixture was stirred for approximately 4 h, then quenched with methanol (20 mL), 10% aqueous citric acid (200 mL), and water (450 mL). The aqueous layer was extracted three times with methylene chloride (800 mL). The organic layers were dried (sodium sulfate), concentrated, and the remnant chromatographed (silica gel, gradient of 2% ethyl acetate in hexane to 20% ethyl acetate in hexane) to yield 1.7 g (45%) of the title compound as a white fluffy solid: $^1$H NMR (300 MHz) $\delta$7.96 (d, J=7.7 Hz, 1H), 7.83 (d, J=6.7 Hz, 1H), 7.3–7.8 (m, 3H), 6.91 (m, 1H), 6.62 (m, 2H), 1.00 (s, 9H), 0.26 (s, 6H); IR (CHCl$_3$) 2958, 2932, 2861, 1616, 1594 cm$^{-1}$; MS (FD) m/e 384 (M$^+$); Anal. calc'd for $C_{21}H_{24}O_3SSi$: C, 65.59; H, 6.29. Found: C, 65.31; H, 6.18.

Preparation 12h 3-(t-Butyldimethylsilyl)oxy-6-phenoxy-6-H-[1]benzothieno[3,2-c][1]benzopyran

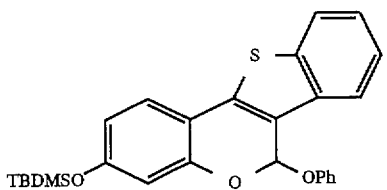

The product of Preparation 12g (0.09 g, 0.24 mmol) and phenol (0.25 g, 2.6 mmol) were dissolved in chlorobenzene (10 mL) and the mixture was stirred for 3 h at 100° C. The mixture was concentrated and residue redissolved in chlorobenzene and reconcentrated in vacuo at approximately 70° C. The residue was then dissolved in diethyl ether, washed five times with saturated sodium carbonate, water and brine. The organic layer was dried (sodium sulfate) and concentrated to yield 0.11 g (100%) of the title compound as a fluffy white solid which was used without further purification: the $^1$H NMR spectrum (300 MHz) was consistent with the structure.

EXAMPLE 10d

3-Hydroxy-6-[4-[2-(1-piperidinyl)ethoxy]phenyl]-6-H-[1]benzothieno[3,2-c][1]benzopyran

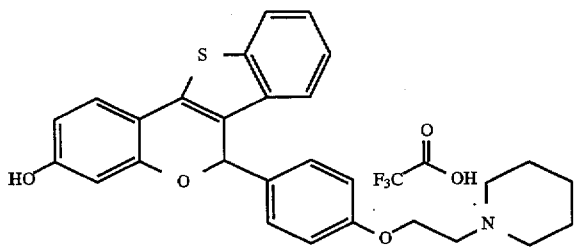

To a solution of the product of Preparation 12h (0.28 g, 0.61 mmol) in toluene (20 mL) at 0° C. was added a 0.2M THF solution of 4-[2-(1-piperidinyl)ethoxy]phenylmagnesium bromide (prepared from the corresponding bromobenzene and magnesium turnings, catalyzed by iodine in THF, 7.6 mL, 1.5 mmol). The mixture was allowed to warm to room temperature and stirred for 1 h. After quenching with water, the mixture was extracted six times with methylene chloride, and the organic layer was dried (sodium sulfate) and concentrated. The remnant was purified via chromatography (silica gel, 4:1–1:1 hexane:ethyl acetate) to give 0.41 g (119%) of the partially purified silylated product.

To a solution of the partially purified product (0.41 g, 0.72 mmol) in THF (10 mL), was added a 1.0M THF solution of tetra-n-butylammonium fluoride (TBAF) (0.67 mL, 0.67 mmol). The solution was stirred at ambient temperature for 10 min, then diluted with ethyl acetate and washed three times with saturated sodium bicarbonate and brine. The organic layers were dried (sodium sulfate) and concentrated. The remnant was triturated from methylene chloride, and the precipitate filtered and rinsed methylene chloride to give 0.23 g (82%) of the title compound as white powdery solid. The solid was slurried in methanol and trifluoroacetic acid was added dropwise until all the material went into solution, the insoluble material was filtered away, and the mother liquor was concentrated in vacuo to yield 0.28 g (80%) of the TFA salt as a fluffy orange solid: $^1$H NMR (300 MHz) δ7.95 (m, 1H), 7.38 (m, 1H), 7.2–7.3 (m, 5H), 6.90 (d, J=8.6 Hz, 2H), 6.76 (s, 1H), 6.51 (dd, J=2.2, 8.2 Hz, 1H), 6.38 (d, J=2.3 Hz, 1H), 4.44 (t, J=4.9 Hz, 2H), 3.5–3.7 (m, 4H), 3.0–3.2 (m, 2H), 1.7–2.0 (m, 5H), 1.4–1.7 (m, 1H); IR (CHCl$_3$) 3271, 3022, 3009, 1670, 1610 cm$^{-1}$; MS (FD) m/e 457 (M$^+$); HRMS (FAB) m/e calc'd for C$_{28}$H$_{28}$NO$_3$S (MH+): 458.1790. Found: 458.1781; Anal. calc'd for C$_{28}$H$_2$NO$_3$S.CF$_3$COOH.1.2H$_2$O: C, 60.69; H, 5.12; N, 2.36. Found: C, 60.62; H, 4.82; N, 2.40.

Preparation 18a 2,8-Bis[(tert-butyldimethylsilyl)oxy]-5H-benzo[b]naphtho[2,1-d]pyran-5-one

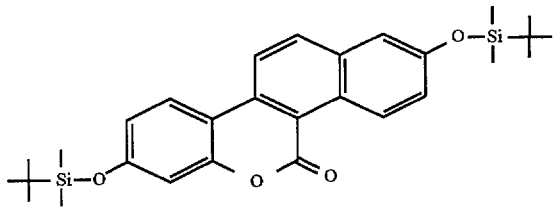

A mixture of the product of Preparation 10 (7.0 g, 13.8 mmol) and 2,3-dichloro-5,6-dicyano-1,4-benzoquinone (DDQ) (3.3 g, 14.5 mmol) in dichloroethane (100 mL) was heated at reflux overnight, inducing the formation of a precipitate. The mixture was filtered hot, rinsing the precipitate with methylene chloride, and the mother liquor concentrated in vacuo. The remnant was partitioned between hexane:ether and water, and the organic layer was dried (magnesium sulfate), concentrated, and recrystallized from hexane to provide 5.5 g (79%) of the title product as a tan solid, mp 154°–156° C.: $^1$H-NMR (300 MHz, CDCl$_3$) δ9.69 (d, J=9.4 Hz), 8.80 (s, 2H), 8.01 (d, J=9.5 Hz), 7.34 (dd, J=9.3,2.5 Hz, 1H), 7.28 (d, J=5.4 Hz, 1H), 6.90 (m, 2H), 1.05 (s, 9H), 1.03 (s, 9H), 0.29 (s, 12H); IR (CHCL$_3$) 1711, 1622, 1604 cm$^{-1}$; MS (FD) m/e 506 (M+); Anal. calc'd. for C$_{29}$H$_{38}$O$_4$Si$_2$: C, 68.72; H, 7.57. Found: C, 68.93; H, 7.36.

Preparation 18b 2,8-Bis[(tert-butyldimethylsilyl)oxy]-5H-benzo[b]naphtho[2,1-d]pyran-5-ol

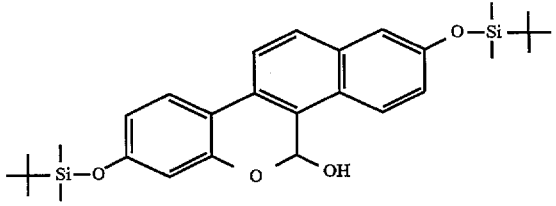

By the procedure described for Preparation 4, the product of Preparation 18a (5.0 g, 9.9 mmol) was reacted with 1.0M diisobutylaluminum hydride in toluene (11.9 mL, 11.9 mmol) to give, after recrystallization from hexane:ether, 4.14 g (82%) of the title compound as a white solid, mp 188°–190° C.: $^1$H NMR (300 MHz, CDCl$_3$) δ7.98 (d, J=9.1

Hz, 1H), 7.86 (d, J=8.8 Hz, 1H), 7.79 (d, J=8.6 Hz, 1H), 7.75 (d, J=8.2 Hz, 1H), 7.23 (d, J=2.3 Hz, 1H), 7.18 (dd, J=9.0, 2.4 Hz, 1H), 7.06 (d, J=7.4 Hz, 1H), 6.67 (m 2H), 3.24 (d, J=7.7 Hz, 1H), 1.04 (s, 9H), 1.02 (s, 9H), 0.27 (s, 6H), 0.27 (s, 6H); IR (CHCl$_3$) 3574 cm$^{-1}$; MS (FD) m/e 508 (M+); Anal. calc'd. for C$_{29}$H$_{40}$O$_4$Si$_2$: C, 68.44; H, 7.94. Found: C, 68.63; H, 8.11.

Preparation 18c 2,8-Bis[(tert-butyldimethylsilyl)oxy]-5-phenoxy-5H-benzo[b]naphtho[2,1-d]pyran

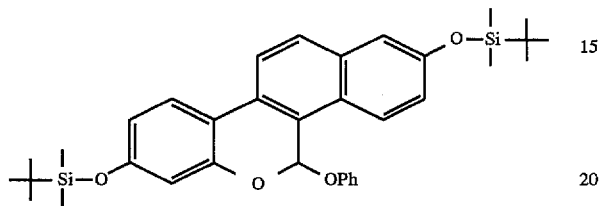

By the procedure described for preparation 5, the product of preparation 18b (3.5 g, 6.88 mmol) was reacted with phenol (3.2 g, 34.3 mmol) to give 3.82 g (95%) of the title compound as an amorphous white solid which was used without further purification: $^1$H NMR (300 MHz) δ7.9–8.1 (m, 4H), 7.61 (s, 1H), 7.3–7.5 (m, 3H), 7.2–7.3 (m, 3H), 7.11 (t, J=7.3 Hz, 1H), 6.74 (dd, J=8.5, 2.3 Hz, 1H), 6.62 (d, J=2.4 Hz, 1H), 1.03 (s, 9H), 0.99 (s, 9H), 0.29 (s, 6H), 0.24 (s, 6H); $^{13}$C NMR (75 MHz) δ157.9, 157.6, 154.3, 151.8, 135.1, 130.4, 130.1, 126.4, 125.8, 125.1, 124.9, 123.9, 123.6, 123.1, 121.1, 118.5, 116.7, 116.2, 115.7, 110.0, 94.8, 26.0, 25.9, 18.8, 18.7, 4.3, −4.4; MS (FD) m/e 584 (M+).

Preparation 18d 2,8-Bis[(tert-butyldimethylsilyl)oxy]-5-[4-[2-(1-piperidinyl)ethoxy]phenyl]-5H-benzo[b]naphtho[2,1-d]pyran

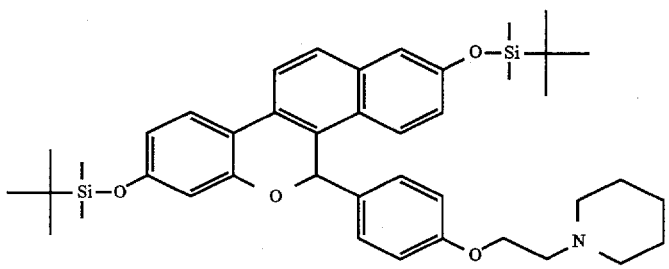

By the procedure described for Preparation 6, the product of Preparation 18c (3.5 g, 6.0 mmol) was reacted with a 0.2M THF solution of 4-[2-(1-piperidinyl)ethoxy] phenylmagnesium bromide to provide, after chromatography (silica gel, 3:2 hexane:ethyl acetate, 0.1% ammonium hydroxide), 3.5 g (84%) of the title compound as a colorless gummy solid: $^1$H NMR (300 MHz) δ7.97 (d, J=8.8 Hz, 1H), 7.89 (d, J=8.7 Hz, 1H), 7.76 (d, J=8.3 Hz, 2H), 7.35 (d, J=2.4 Hz, 1H), 7.10 (m, 3H), 7.02 (s, 1H), 6.73 (d, J=8.7 Hz, 2H), 6.53 (dd, J=8.3, 2.4 Hz, 1H); 6.37 (d, J=2.2 Hz, 1H), 3.95 (t, J=6.0 Hz, 2H), 2.58 (t, J=6.0 Hz, 2H), 2.38 (m, 4H), 1.4–1.5 (m, 4H), 1.3–1.4 (m, 2H), 1.00 (s, 9H), 0.94 (s, 9H), 0.25 (s, 6H), 0.19 (s, 6H); $^{13}$C NMR (75 MHz) δ159.8, 157.6, 154.1, 154.0, 135.0, 132.2, 130.1, 128.6, 127.3, 126.3, 126.2, 125.6, 124.7, 123.4, 121.6, 118.0, 116.5, 115.0, 114.5, 110.3, 76.0, 66.8, 58.5, 55.6, 26.8, 26.0, 26.0, 25.0, 18.7, 18.7, −4.2, −4.3; MS (FD) m/e 696 (M+); Anal. calc'd. for C$_{42}$H$_{57}$NO$_4$Si$_2$: C, 72.46; H, 8.27; N, 2.01. Found: C, 72.53; H, 8.49; N, 2.08.

EXAMPLE 11b 2,8-Dihydroxy-5-[4-[2-(1-piperidinyl)ethoxy]phenyl]-5H-benzo[b]naphtho[2,1-d]pyran

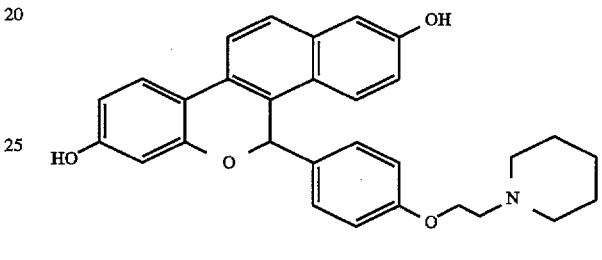

By the procedure described for Example 1, the product of preparation 18d (3.4 g, 4.9 mmol) was reacted with a 1.0M TBAF in THF (24.4 mmol) to provide, after chromatography (silica gel, 1:1 hexane:ethyl acetate, 10% methanol, 0.1% ammonium hydroxide) and trituration with ether, 2.2 g (96%) of the title compound as a white solid, mp 158°–161° C.: $^1$H NMR (300 MHz) δ7.89 (d, J=8.7 Hz, 1H), 7.77 (d, J=8.7 Hz, 1H), 7.68 (m, 2H), 7.23 (d, J=2.4 Hz, 1H), 7.09 (m, 3H), 6.97 (s, 1H), 6.71 (d, J=8.7 Hz, 2H), 6.49 (dd, J=8.3, 2.4 Hz, 1H), 6.36 (d, J=2.3 Hz, 1H), 3.95 (t, J=6.0 Hz, 2H), 2.60 (t, J=6.0 Hz, 2H), 2.40 (m, 4H), 1.4–1.5 (m, 4H), 1.3–1.4 (m, 2H); $^{13}$C NMR (75 MHz) δ159.5, 159.5, 155.8, 153.9, 135.0, 132.4, 130.1, 128.0, 126.7, 125.6, 125.4, 125.3, 124.7, 121.4, 119.9, 116.1, 114.8, 111.0, 110.1, 105.5, 75.8, 66.1, 58.3, 55.3, 26.3, 24.7; IR (KBr) 2934 cm$^{-1}$; MS (FD) m/e 468 (MH+); Anal. calc'd. for C$_{30}$H$_{29}$NO$_4$.H$_2$O: C, 74.19; H, 6.45; N, 2.88. Found: C, 74.13; H, 6.45; N, 2.88.

Preparation 22a 2,8-Dimethoxy-5-[4-[(tert-butyldimethylsilyl)oxy]phenyl]-6H-benzo[c]phenanthrid-6-one

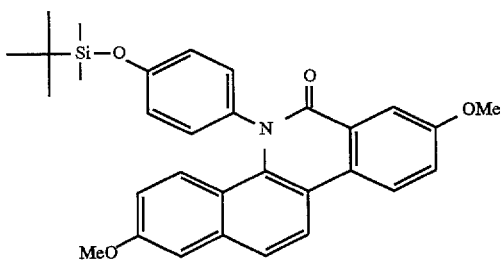

A mixture of the product of preparation 22 (100 mg, 0.19 mmol) and 2,3-dichloro-5,6-dicyano-1,4-benzoquinone (DDQ) (47 mg, 0.21 mmol) in dichloroethane (10 mL) was heated at reflux for 2 h, inducing the formation of a precipitate. The mixture was cooled to room temperature, filtered, and the filtrate diluted with $CH_2Cl_2$ (70 mL), washed with 1N sodium hydroxide (2×70 mL), dried ($Na_2SO_4$) and concentrated to provide 98 mg (98%) of the title compound as a white, crystalline solid, mp 211°–213° C.: $^1$H NMR (300 MHz, $CDCl_3$) δ8.21 (d, J=9.0 Hz, 1H), 8.16 (d, J=8.9 Hz, 1H), 7.95 (d, J=2.8 Hz, 1H), 7.60 (d, J=8.8 Hz, 1H), 7.37 (dd, J=9.0, 2.8 Hz, 1H), 7.25 (d, J=9.7 Hz, 1H), 7.21 (d, J=8.7 Hz, 2H), 7.08 (d, J=2.7 Hz, 1H), 6.93 (d, J=8.7 Hz, 2H), 6.66 (dd, J=9.7, 2.8 Hz, 1H), 3.94 (s, 3H), 3.87 (s, 3H), 1.02 (s, 9H), 0.25 (s, 6H); $^{13}$C NMR (75 MHz, $CDCl_3$) δ163.1, 159.2, 156.9, 154.9, 137.3, 136.3, 133.8, 129.8, 128.3, 127.4, 126.4, 123.9, 123.7, 122.9, 120.7, 120.5, 119.5, 116.5, 115.7, 109.1, 106.9, 55.5, 55.1, 25.7, 18.3, −4.2; IR ($CHCl_3$) 1646, 1619 cm$^{-1}$; MS (FD) m/e 511 (M+); Anal. calc'd. for $C_{31}H_{33}NO_4Si$: C, 72.75; H, 6.51; N, 2.74. Found: C, 72.57; H, 6.50; N, 2.83.

Preparation 23a 2,8-Dimethoxy-5-(4-hydroxyphenyl)-6H-benzo[c]phenanthrid-6-one

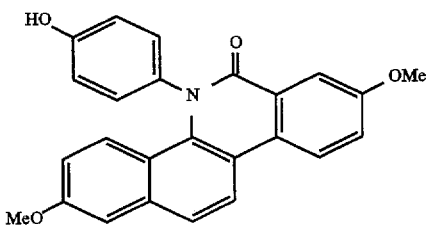

The product of Preparation 22a (6.8 g, 13.3 mmol) was dissolved in 1:1 acetonitrile:methylene chloride (200 mL) and treated with hydrogen fluoride-pyridine (80 mL) for 1 h. The mixture was diluted with brine (500 mL) and extracted with THF (3×300 mL). The combined organic layers were neutralized with saturated sodium bicarbonate and the resulting aqueous layer was washed with THF (2×500 mL). All aqueous layers were then combined and washed with THF (500 mL), and the combined organic layers were dried (sodium sulfate), and concentrated, and the solid residue was washed with acetone to provide 5.27 g (100%) of the title compound as an off-white powder, mp 310 d°C.: $^1$H NMR (300 MHz, DMSO-$d_6$) δ9.79 (bs, 1H), 8.52 (d, J=9.0 Hz, 1H), 8.42 (d, J=9.0 Hz, 1H), 7.72 (m, 2H), 7.47 (dd, J=8.7, 2.3 Hz, 1H), 7.31 (d, 2.1 Hz, 1H), 7.21 (d, J=9.6 Hz, 1H), 7.07 (d, J=8.4 Hz, 2H), 6.82 (d, J=8.3 Hz, 2H), 6.68 (dd, J=9.3, 2.6 Hz, 1H), 3.87 (s, 3H), 3.79 (s, 3H); MS (FD) m/e 397 (M+).

EXAMPLE 12a 2,8-Hydroxy-5-[4-[2-(1-piperidinyl)ethoxy]phenyl]-11,12-dihydro-6H-benzo[c]phenanthrid-6-one

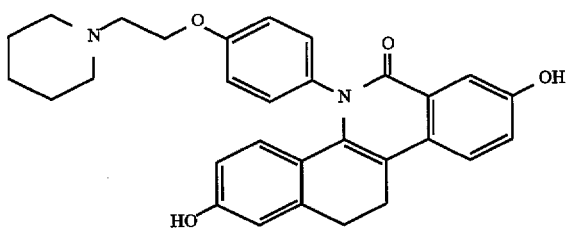

By the procedure described for Example 14, the product of Example 12 (310 mg, 0.61 mmol) was reacted with ethanethiol (189 mg, 3.1 mmol) and aluminum chloride (611 mg, 4.6 mmol) to provide after radial chromatography (silica gel, 1:1 hexane:ethyl acetate, 10–20% methanol, under an ammonia atmosphere) 237 mg (81%) of the title compound as a yellow foam which crystallized upon trituration with ether, mp 166–174 d°C.: $^1$H NMR (300 MHz, methanol-$d_4$) δ7.80 (d, J=8.9 Hz, 1H), 7.73 (d, J=2.6 Hz, 1H), 7.30 (dd, J=8.9, 2.7 Hz, 1H), 7.19 (d, J=8.8 Hz, 2H), 6.97 (d, J=8.9 Hz, 2H), 6.66 (d, J=2.5 Hz, 1H), 6.56 (d, J=8.7 Hz, 1H), 6.21 (dd, J=8.7, 2.6 Hz, 1H), 4.16 (t, J=5.6 Hz, 2H), 2.86 (s, 4H), 2.81 (t, J=5.6 Hz, 2H), 2.59 (m, 4H), 1.6–1.7 (m, 4H), 1.4–1.6 (m, 2H); IR ($CHCl_3$) 3673, 1637, 1602 cm$^{-1}$; MS (FD) m/e 482 (M+); Anal. calc'd. for $C_{30}H_{30}N_2O_4 \cdot H_2O$: C, 71.96; H, 6.46; N, 5.60. Found: C, 71.68; H, 6.63; N, 5.46.

EXAMPLE 12b 2,8-Dimethoxy-5-[4-[2-(1-piperidinyl)ethoxy]phenyl]-11,12-dihydro-6H-benzo[c]phenanthridine

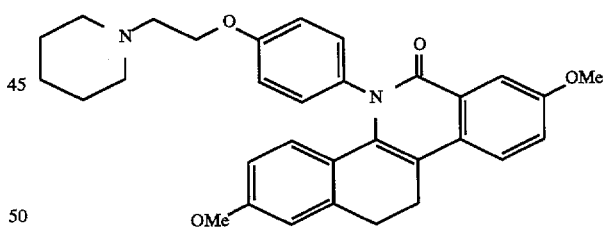

A solution of the product of Example 12 (350 mg, 0.69 mmol) in THF (25 mL) was treated with lithium aluminum hydride (129 mg, 3.4 mmol) inducing a moderate exotherm. The mixture was allowed to return to room temperature and stirred for 2 h, then briefly warmed to reflux, cooled, and quenched with ethyl acetate (50 mL) followed by saturated ammonium chloride (50 mL). The aqueous layer was extracted with ethyl acetate (2×50 mL), and the combined organic layers were dried (sodium sulfate), concentrated; and purified via radial chromatography (silica gel, 1:1 hexane:ethyl acetate, 5% methanol, under an ammonia atmosphere) to provide 248 mg (64%) of the title compound as a yellow foam: $^1$H NMR (300 MHz, $CDCl_3$) δ7.28 (d, J=8.5 Hz, 1H), 7.05 (d, J=8.5 Hz, 1H), 6.79 (m, 3H), 6.72 (d, J=2.6 Hz, 1H), 6.65 (d, 9.0 Hz, 2H), 6.58 (d, J=2.6 Hz, 1H), 6.52 (dd, J=8.6, 2.6 Hz, 1H), 4.65 (s, 2H), 3.94 (t, J=6.1 Hz, 2H), 3.74 (s, 3H), 3.74 (s, 3H), 2.96 (dd, J=8.3, 5.6, 2H), 2.81 (dd, J=8.3, 5.9 Hz, 2H), 2.66 (t, J=6.1 Hz, 2H), 2.43 (m, 4H), 1.5–1.6 (m, 4H), 1.3–1.5 (m, 2H); $^{13}$C NMR (75 MHz, CDCl$_3$) δ158.5, 158.3, 153.3, 141.7, 138.4, 134.6, 132.3, 126.6, 126.2, 125.3, 122.9, 121.7, 120.5, 114.9, 113.4, 112.3, 111.2, 111.0, 65.8, 57.8, 55.6, 55.2, 55.1, 54.8, 29.0, 25.7, 24.0, 22.2; IR (CHCl$_3$) 1610, 1506 cm$^{-1}$; MS (FD) m/e 496 (M+); Anal. calc'd. for $C_{32}H_{36}N_2O_3$: C, 77.37; H, 7.32; N, 5.64. Found: C, 77.25; H, 7.12; N, 5.75.

EXAMPLE 12c 2,8-Dimethoxy-5-[4-[2-(1-piperidinyl)ethoxy]phenyl]-6H-benzo[c]phenanthrid-6-one

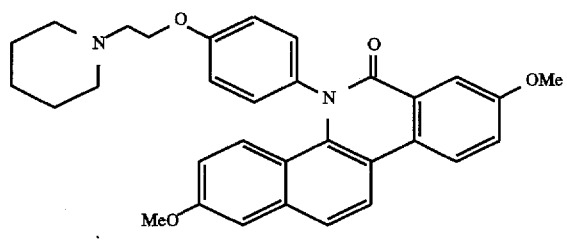

By the method described for Example 12, the product of Preparation 23a (4.8 g, 12.1 mmol), triphenylphosphine (6.3 g, 24.2 mmol), and 1-(2-hydroxyethyl)piperidine (3.9 g, 30.3 mmol) were reacted with diethyl diazodicarboxylate (DEAD) (4.2 g, 24.2 mmol) to provide, after chromatography (silica gel, 1:1 hexane:ethyl acetate, 5–20% methanol, 0.1% ammonium hydroxide) and recrystallization from ethyl acetate, 5.14 g (84%) of the title compound as a fluffy white solid, mp 176° C.: $^1$H NMR (300 MHz, CDCl$_3$) δ8.25 (d, J=9.1 Hz, 1H), 8.21 (d, J=8.8 Hz, 1H), 7.96 (d, J=2.8 Hz, 1H), 7.64 (d, J=8.8 Hz, 1H), 7.40 (dd, J=9.0, 2.8 Hz, 1H), 7.31 (d, J=9.7 Hz, 1H), 7.26 (d, J=8.8 Hz, 2H), 7.10 (d, J=2.7 Hz, 1H), 6.99 (d, J=8.9 Hz, 2H), 6.70 (dd, J=9.6, 2.7 Hz, 1H), 4.16 (t, J=6.0 Hz, 2H), 3.95 (s, 3H), 3.88 (s, 3H), 2.81 (t, J=6.0 hz, 2H), 2.53 (m, 4H), 1.5–1.7 (m, 4H), 1.4–1.5 (m, 2H); $^{13}$C NMR (75 MHz; CDCl$_3$) δ163.2, 159.2, 157.9, 156.9, 136.3, 135.7, 133.7, 129.7, 128.3, 127.3, 126.4, 123.9, 123.7, 122.8, 120.5, 119.4, 116.6, 115.7, 115.1, 109.1, 106.9, 66.2, 57.8, 55.5, 55.1, 55.0, 25.9, 24.1; IR (CHCl$_3$) 1647, 1619 cm$^{-1}$; MS (FD) m/e 508 (M+) ; Anal. calc'd. for $C_{32}H_{32}N_2)O_4$: C, 75.56; H, 6.35; N, 5.51. Found: C, 75.58; H, 6.28; N, 5.77.

EXAMPLE 12d 2,8-Hydroxy-5-[4-[2-(1-piperidinyl)ethoxy]phenyl]-6H-benzo[c]phenanthrid-6-one

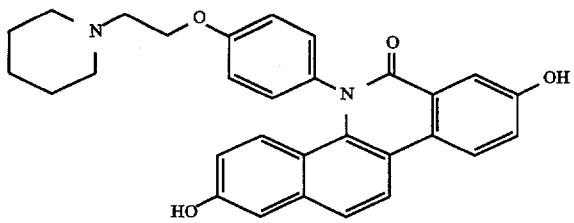

By the procedure described for Example 14, the product of Example 12a (500 mg, 0.98 mmol) was reacted with ethanethiol (304 mg, 4.9 mmol) and aluminum chloride (987 mg, 7.4 mmol) to provide after chromatography (silica gel, 1:1 hexane:ethyl acetate, 10–30% methanol, 0.1% ammonium hydroxide) and crystallization from methanol 397 mg (84%) of the title compound as a white powder. An analytical sample was recrystallized from methanol/CHCl$_3$, mp 227–232 d°C.: $^1$H NMR (300 MHz, DMSO-d$_6$) δ10.15 (bs, 1H), 9.82 (bs, 1H), 8.43 (d, J=8.9 Hz, 1H), 8.34 (d, J=9.2 Hz, 1H), 7.69 (s, 1H), 7.63 (d, J=9.0 Hz, 1H), 7.34 (d, J=8.9 Hz, 1H), 7.0–7.3 (m, 6H), 6.58 (d, J=9.6 Hz, 1H), 4.13 (t, J=5.6 Hz, 2H), 2.69 (t, J=5.5 Hz, 2H), 2.46 (m, 4H), 1.3–1.6 (m, 6H); $^{13}$C NMR (75 MHz, DMF-d$_7$/acetone-d$_6$/CDCl$_3$) δ162.2, 158.4, 157.3, 155.9, 137.4, 137.2, 133.9, 130.8, 127.6, 127.5, 126.9, 125.0, 124.0, 123.1, 121.1, 119.0, 117.3, 115.7, 115.5, 112.8, 110.6, 63.4, 55.8, 53.6, 23.2, 22.1; IR (KBr) 3303, 1643, 1602 cm$^{-1}$; MS (FD) m/e 480 (M+); Anal. calc'd. for $C_{30}H_{28}N_2O_4$·0.5H$_2$O: C, 73.59; H, 5.98; N, 5.72. Found: C, 73.72; H, 5.88; N, 5.71.

EXAMPLE 13

2,8-Dimethoxy-5-[4-[2-(1-piperidinyl)ethoxy]phenyl]-6H-benzo[c]phenanthridine

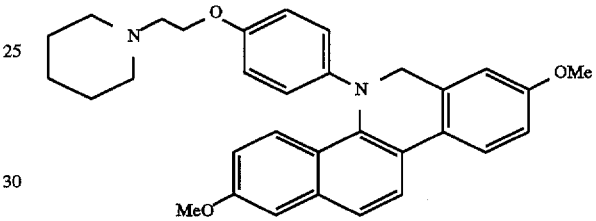

A solution of the product of Example 12a (3.82 g, 7.51 mmol) in THF (250 mL) was treated with lithium aluminum hydride (1.43 g, 37.5 mmol) resulting in a moderate exotherm. After the exotherm ceased, the mixture was warmed to reflux overnight, cooled to room temperature, and quenched cautiously with ethyl acetate (200 mL) followed by 1N sodium hydroxide (200 mL). The layers were separated and the aqueous layer extracted with ethyl acetate (2×200 mL) and the combined organic layers were washed with brine (200 mL), dried (sodium sulfate), and concentrated. The residue was recrystallized from hexane:ethyl acetate to provide 3.24 g (87%) of the title compound as an off-white solid, mp 136–137: $^1$H NMR (300 MHz, CDCl$_3$) δ7.91 (d, J=8.6 Hz, 1H), 7.74 (d, J=8.8 Hz, 2H), 7.61 (d, J=8.6 Hz, 1H), 7.12 (d, J=2.5 Hz, 1H), 6.95 (dd, J=9.2, 2.6, 1H), 6.91 (dd, J=8.5, 2.6 Hz, 1H), 6.6–6.8 (m, 5H), 4.75 (s, 2H), 3.95 (t, J=6.1 Hz, 2H), 3.90 (s, 3H), 3.79 (s, 3H), 2.68 (t, J=6.1 Hz, 2H), 2.44 (m, 4H), 1.5–1.7 (m, 4H), 1.4–1.5 (m, 2H); $^{13}$C NMR (75 MHz, CDCl$_3$) δ159.1, 157.3, 153.4, 143.5, 137.9, 135.0, 134.1, 126.5, 125.6, 124.9, 124.2, 123.8, 123.7, 122.4, 121.7, 118.1, 114.9, 113.8, 111.2, 106.4, 65.8, 57.8, 55.8, 55.2, 54.8, 25.7, 24.0; IR (CHCl$_3$) 1506 cm$^{-1}$; MS (FD) m/e 494 (M+); Anal. calc'd. for $C_{32}H_{34}N_2O_3$: C, 77.70; H; 6.94; N, 5.66. Found: C, 77.54; H, 6.99; N, 5.63.

Test Procedure

General Preparation Procedure

In the examples illustrating the methods, a postmenopausal model was used in which effects of different treatments upon circulating lipids were determined.

Seventy-five day old female Sprague Dawley rats (weight range of 200 to 225 g) were obtained from Charles River Laboratories (Portage, Mich.). The animals were either bilaterally ovariectomized (OVX) or exposed to a Sham surgical procedure at Charles River Laboratories, and then shipped after one week. Upon arrival, they were housed in metal hanging cages in groups of 3 or 4 per cage and had ad libitum access to food (calcium content approximately 0.5%) and water for one week. Room temperature was maintained at 22.2°±1.7° C. with a minimum relative humidity of 40%. The photoperiod in the room was 12 hours light and 12 hours dark.

Dosing Regimen Tissue Collection. After a one week acclimation period (therefore, two weeks post-OVX) daily dosing with test compound was initiated. 17a-ethynyl estradiol or the test compound were given orally, unless otherwise stated, as a suspension in 1% carboxymethylcellulose or dissolved in 20% cyclodextrin. Animals were dosed daily for 4 days. Following the dosing regimen, animals were weighed and anesthetized with a ketamine: Xylazine (2:1, V:V) mixture and a blood sample was collected by cardiac puncture. The animals were then sacrificed by asphyxiation with $CO_2$, the uterus was removed through a midline incision, and a wet uterine weight was determined.

Cholesterol Analysis. Blood samples were allowed to clot at room temperature for 2 hours, and serum was obtained following centrifugation for 10 minutes at 3000 rpm. Serum cholesterol was determined using a Boehringer Mannheim Diagnostics high performance cholesterol assay. Briefly the cholesterol was oxidized to cholest-4-en-3-one and hydrogen peroxide. The hydrogen peroxide was then reacted with phenol and 4-aminophenazone in the presence of peroxidase to produce a p-quinone imine dye, which was read spectrophotometrically at 500 nm. Cholesterol concentration was then calculated against a standard curve. The entire assay was automated using a Biomek Automated Workstation.

Uterine Eosinophil Peroxidase (EPO) Assay. Uteri were kept at 4° C. until time of enzymatic analysis. The uteri were then homogenized in 50 volumes of 50 mM Tris buffer (pH-8.0) containing 0.005% Triton X-100. Upon addition of 0.01% hydrogen peroxide and 10 mM O-phenylenediamine (final concentrations) in Tris buffer, increase in absorbance was monitored for one minute at 450 nm. The presence of eosonophils in the uterus is an indication of estrogenic activity of a compound. The maximal velocity of a 15 second interval was determined over the initial, linear portion of the reaction curve.

Source of Compound: 17α-ethynyl estradiol was obtained from Sigma Chemical Co., St. Louis, Mo.

Influence of Formula I and II Compounds on Serum Cholesterol and Determination of Agonist/Non-Agonist Activity Data presented in Table 1 below show comparative results among ovariectomized rats, rats treated with 17α-ethynyl estradiol ($EE_2$; an orally available form of estrogen), and rats treated with certain compounds of the present invention. Although $EE_2$ caused a decrease in serum cholesterol when orally administered at 0.1 mg/kg/day, it also exerted a stimulatory action on the uterus so that $EE_2$ uterine weight was substantially greater than the uterine weight of ovariectomized test animals. This uterine response to estrogen is well recognized in the art.

Not only did the compounds of the present invention generally reduce serum cholesterol compared to the ovariectomized control animals, but uterine weight was only minimally increased to slightly decreased with the majority of the formula compounds tested. Compared to estrogenic compounds known in the art, the benefit of serum cholesterol reduction without adversely affecting uterine weight is quite rare and desirable.

As is expressed in the below data, estrogenicity also was assessed by evaluating the adverse response of eosinophil infiltration into the uterus. The compounds of the present invention did not cause any increase in the number of eosinophils observed in the stromal layer of ovariectomized rats, while estradiol cause a substantial, expected increase in eosinophil infiltration.

The data presented in the Tables 1 below reflects the response of 5 to 6 rats per treatment.

TABLE 1

| Compound | Dose mg/kg | Uterine Weight (% increase vs. OVX) | Uterine EPO (V. max) | Serum Cholesterol (% decrease vs. OVX) |
| --- | --- | --- | --- | --- |
| $EE_2$ | 0.1 | 86.3 | 116.4 | 81.4 |
| Example 1 | 0.1 | 25.3 | 7.8 | 72.8 |
|  | 1.0 | 9.2 | 3.0 | 51.0 |
|  | 10.0 | 5.9 | 2.1 | 54.6 |
| Example 3 | 0.1 | 32.5 | 4.2 | 51.5 |
|  | 1.0 | 7.4 | 3.0 | 50.8 |
| Example 4 | 0.1 | 10 | 3.3 | 62.6 |
|  | 1.0 | 15.3 | 3.3 | 48.2 |
| Example 5 | 0.1 | −5.1 | 4.5 | −9 |
|  | 1.0 | 18.6 | 4.8 | 61.3 |
| Example 6 | 0.1 | 23 | 4.2 | −2.5 |
|  | 1.0 | 6.4 | 1.8 | 9.9 |
|  | 10.0 | 50.0 | 3.6 | −11.4 |
| Example 7 | 0.1 | 28.9 | 4.8 | 39.8 |
|  | 1.0 | 31.2 | 6.6 | 65.5 |
|  | 10.0 | 14.7 | 3.6 | 54.0 |
| Example 8 | 0.01 | 10.2 | 2.1 | 50.5 |
|  | 0.1 | 27.4 | 4.8 | 38.5 |
|  | 1.0 | 27.2 | 4.8 | 68.0 |
| Example 9 | 0.1 | 77.8 | 52.2 | 40.1 |
|  |  | 109.1 | 83.1 | 54.7 |
|  |  | 94.6 | 75.0 | 65.2 |
| Example 11 | 0.1 | −8.8 | 2.7 | 17.4 |
|  | 1.0 | 3 | 4.2 | 30.9 |
|  | 10.0 | −12.6 | 4.2 | 36.3 |
| Example 14 | 0.01 | −0.6 | 2.7 | 24.8 |
|  | 0.1 | 60.0 | 5.4 | 59.5 |
|  | 1.0 | 49.1 | 36.0 | 60.7 |
| Example 11b | 0.1 | 13.6 | 9.3 | 66.4 |
|  | 1.0 | 7.6 | 12.0 | 73.9 |
|  | 10.0 | −4.1 | 7.8 | 61.4 |

In addition to the demonstrated benefits of the compounds of the present invention, especially when compared to estradiol, the above data clearly demonstrate that compounds of Formula I and II are not estrogen mimetics. Furthermore, no deleterious toxicological effects (survival) were observed with any treatment.

Osteoporosis Test Procedure

Following the General Preparation Procedure, infra, the rats were treated daily for 35 days (6 rats per treatment group) and sacrificed by carbon dioxide asphyxiation on the 36th day. The 35 day time period was sufficient to allow maximal reduction in bone density, measured as described herein. At the time of sacrifice, the uteri were removed, dissected free of extraneous tissue, and the fluid contents were expelled before determination of wet weight in order to confirm estrogen deficiency associated with complete ovariectomy. Uterine weight was routinely reduced about 75% in response to ovariectomy. The uteri were then placed in 10% neutral buffered formalin to allow for subsequent histological analysis.

The right femurs were excised and digitilized x-rays generated and analyzed by an image analysis program (NIH image) at the distal metaphysis. The proximal aspect of the tibiae from these animals were also scanned by quantitative computed tomography.

In accordance with the above procedures, compounds of the present invention and ethynyl estradiol ($EE_2$) in 20% hydroxypropyl b-cyclodextrin were orally administered to test animals. Distal femur metaphysis data presented in Tables 2 and 3 below are the results of formula I compound treatments compared to intact and ovariectomized test animals. Results are reported as percent protection relative to ovariectomy.

TABLE 2

| Compound/Treatment | Dose /kg | Distal Femur Metaphysis (X-ray Image Analysis-Gray Score) |
|---|---|---|
| EE2 | 0.1 mg | 62.4* |
| Example 1 | 0.01 mg | 14.2 |
|  | 0.1 mg | 49.8* |
|  | 1.0 mg | 51.7* |
|  | 10.0 mg | 48.2* |
| Example 11b | 0.01 mg | 45.6* |
|  | 0.1 mg | 38.5* |
|  | 1.0 mg | 58.5* |
|  | 10.0 mg | 37.3* |

*P <= 0.5 two tailed Student's T Test on raw data.

In summary, ovariectomy of the test animals caused a significant reduction in femur density compared to intact, vehicle treated controls. Orally administered ethynyl estradiol ($EE_2$) prevented this loss, but the risk of uterine stimulation with this treatment is ever-present.

The compounds of the present invention also prevented bone loss in a general, dose-dependent manner. Accordingly, the compounds of the present invention are useful for the treatment of post-menopausal syndrome, particularly osteoporosis.

MCF-7 Proliferation Assay

MCF-7 breast adenocarcinoma cells (ATCC HTB 22) were maintained in MEM (minimal essential medium, phenol red-free, Sigma, St. Louis, Mo.) supplimented with 10% fetal bovine serum (PBS) (V/V), L-glutamine (2 mM), sodium pyruvate (1 mM), HEPES {(N-[2-hydroxyethyl] piperazine-N'-[2-ethanesulfonic acid]10 mM)}, nonessential amino acids and bovine insulin (1 ug/mL) (maintenance medium). Ten days prior to assay, MCF-7 cells were switched to maintenance medium supplemented with 10% dextran coated charcoal stripped fetal bovine serum (DCC-FBS) assay medium) in place of 10% FBS to deplete internal stores of steroids. MCF-7 cells were removed from maintenance flasks using cell dissociation medium (Ca++/ Mg++ free HBSS (phenol red-free) supplemented with 10 mM HEPES and 2 mM EDTA). Cells were washed twice with assay medium and adjusted to 80,000 cells/mL. Approximately 100 mL (8,000 cells) were added to flat-bottom microculture wells (Costar 3596) and incubated at 37° C. in a 5% $CO_2$ humidified incubator for 48 hours to allow for cell adherence and equilibration after transfer. Serial dilutions of drugs or DMSO as a diluent control were prepared in assay medium and 50 mL transferred to triplicate microcultures followed by 50 mL assay medium for a final volume of 200 mL. After an additional 48 hours at 37° C. in a 5% $CO_2$ humidified incubator, microcultures were pulsed with tritiated thymidine (1 uCi/well) for 4 hours. Cultures were terminated by freezing at −70° C. for 24 hours followed by thawing and harvesting of microcultures using a Skatron Semiautomatic Cell Harvester. Samples were counted by liquid scintillation using a Wallac BetaPlace b counter. Results in Table 3 below show the $IC_{50}$ for certain compounds of the present invention.

TABLE 3

| Compound (Example Reference) | $IC_{50}$ nM |
|---|---|
| 1 | 0.2 |
| 2 | 100 |
| 3 | 3.0 |
| 4 | 5.0 |
| 5 | 1000 |
| 6 | 500 |
| 11 | 0.7 |
| 14 | 1 |

DMBA-Induced Mammary Tumor Inhibition

Estrogen-dependent mammary tumors are produced in female Sprague-Dawley rats which are purchased from Harlan Industries, Indianapolis, Ind. At about 55 days of age, the rats receive a single oral feeding of 20 mg of 7,12-dimethylbenz[a]anthracene (DMBA). About 6 weeks after DMBA administration, the mammary glands are palpated at weekly intervals for the appearance of tumors. Whenever one or more tumors appear, the longest and shortest diameters of each tumor are measured with a metric caliper, the measurements are recorded, and that animal is selected for experimentation. An attempt is made to uniformly distribute the various sizes of tumors in the treated and control groups such that average-sized tumors are equivalently distributed between test groups. Control groups and test groups for each experiment contain 5 to 9 animals.

Compounds of Formula I are administered either through intraperitoneal injections in 2% acacia, or orally. Orally administered compounds are either dissolved or suspended in 0.2 mL corn oil. Each treatment, including acacia and corn oil control treatments, is administered once daily to each test animal. Following the initial tumor measurement and selection of test animals, tumors are measured each week by the above-mentioned method. The treatment and measurements of animals continue for 3 to 5 weeks at which time the final areas of the tumors are determined. For each compound and control treatment, the change in the mean tumor area is determined.

Uterine Fibrosis Test Procedures

Test 1

Between 3 and 20 women having uterine fibrosis are administered a compound of the present invention. The amount of compound administered is from 0.1 to 1000 mg/day, and the period of administration is 3 months.

The women are observed during the period of administration, and up to 3 months after discontinuance of administration, for effects on uterine fibrosis.

Test 2

The same procedure is used as in Test 1, except the period of administration is 6 months.

Test 3

The same procedure is used as in Test 1, except the period of administration is 1 year.

Test 4

A. Induction of fibroid tumors in guinea pig

Prolonged estrogen stimulation is used to induce leiomyomata in sexually mature female guinea pigs. Animals are dosed with estradiol 3–5 times per week by injection for 2–4 months or until tumors arise. Treatments consisting of a compound of the invention or vehicle is administered daily for 3–16 weeks and then animals are sacrificed and the uteri harvested and analyzed for tumor regression.

B. Implantation of human uterine fibroid tissue in nude mice

Tissue from human leiomyomas are implanted into the peritoneal cavity and or uterine myometrium of sexually mature, castrated, female, nude mice. Exogenous estrogen are supplied to induce growth of the explanted tissue. In some cases, the harvested tumor cells are cultured in vitro prior to implantation. Treatment consisting of a compound of the present invention or vehicle is supplied by gastric gavage on a daily basis for 3–16 weeks and implants are removed and measured for growth or regression. At the time of sacrifice, the uteri are harvested to assess the status of the organ.

Test 5

A. Tissue from human uterine fibroid tumors is harvested and maintained, in vitro, as primary nontransformed cultures Surgical specimens are pushed through a sterile mesh or sieve, or alternately teased apart from surrounding tissue to produce a single cell suspension. Cells are maintained in media containing 10% serum and antibiotic. Rates of growth in the presence and absence of estrogen are determined. Cells are assayed for their ability to produce complement component C3 and their response to growth factors and growth hormone. In vitro cultures are assessed for their proliferative response following treatment with progestins, GnRH, a compound of the present invention and vehicle. Levels of steroid hormone receptors are assessed weekly to determine whether important cell characteristics are maintained in vitro. Tissue from 5–25 patients are utilized.

Activity in at least one of the above tests indicates the compounds of the present invention are of potential in the treatment of uterine fibrosis.

Endometriosis Test Procedure

In Tests 1 and 2, effects of 14-day and 21-day administration of compounds of the present invention on the growth of explanted endometrial tissue can be examined.

Test 1

Twelve to thirty adult CD strain female rats are used as test animals. They are divided into three groups of equal numbers. The estrous cycle of all animals is monitored. On the day of proestrus, surgery is performed on each female. Females in each group have the left uterine horn removed, sectioned into small squares, and the squares are loosely sutured at various sites adjacent to the mesenteric blood flow. In addition, females in Group 2 have the ovaries removed.

On the day following surgery, animals in Groups 1 and 2 receive intraperitoneal injections of water for 14 days whereas animals in Group 3 receive intraperitoneal injections of 1.0 mg of a compound of the present invention per kilogram of body weight for the same duration. Following 14 days of treatment, each female is sacrificed and the endometrial explants, adrenals, remaining uterus, and ovaries, where applicable, are removed and prepared for histological examination. The ovaries and adrenals are weighed.

Test 2

Twelve to thirty adult CD strain female rats are used as test animals. They are divided into two equal groups. The estrous cycle of all animals is monitored. On the day of proestrus, surgery is performed on each female. Females in each group have the left uterine horn removed, sectioned into small squares, and the squares are loosely sutured at various sites adjacent to the mesenteric blood flow.

Approximately 50 days following surgery, animals assigned to Group 1 receive intraperitoneal injections of water for 21 days whereas animals in Group 2 receive intraperitoneal injections of 1.0 mg of a compound of the present invention per kilogram of body weight for the same duration. Following 21 days of treatment, each female is sacrificed and the endometrial explants and adrenals are removed and weighed. The explants are measured as an indication of growth. Estrous cycles are monitored.

Test 3

A. Surgical induction of endometriosis

Autographs of endometrial tissue are used to induce endometriosis in rats and/or rabbits. Female animals at reproductive maturity undergo bilateral oophorectomy, and estrogen is supplied exogenously thus providing a specific and constant level of hormone. Autologous endometrial tissue is implanted in the peritoneum of 5–150 animals and estrogen supplied to induce growth of the explanted tissue. Treatment consisting of a compound of the present invention is supplied by gastric lavage on a daily basis for 3–16 weeks, and implants are removed and measured for growth or regression. At the time of sacrifice, the intact horn of the uterus is harvested to assess status of endometrium.

B. Implantation of human endometrial tissue in nude mice

Tissue from human endometrial lesions is implanted into the peritoneum of sexually mature, castrated, female, nude mice. Exogenous estrogen is supplied to induce growth of the explanted tissue. In some cases, the harvested endometrial cells are cultured in vitro prior to implantation. Treatment consisting of a compound of the present invention supplied by gastric gavage on a daily basis for 3–16 weeks, and implants are removed and measured for growth or regression. At the time of sacrifice, the uteri are harvested to assess the status of the intact endometrium.

Test 4

A. Tissue from human endometrial lesions is harvested and maintained in vitro as primary nontransformed cultures Surgical specimens are pushed through a sterile mesh or sieve, or alternately teased apart from surrounding tissue to produce a single cell suspension. Cells are maintained in media containing 10% serum and antibiotic. Rates of growth in the presence and absence of estrogen are determined. Cells are assayed for their ability to produce complement component C3 and their response to growth factors and growth hormone. In vitro cultures are assessed for their proliferative response following treatment with progestins, GnRH, a compound of the invention, and vehicle. Levels of steroid hormone receptors are assessed weekly to determine whether important cell characteristics are maintained in vitro. Tissue from 5–25 patients is utilized.

Activity in any of the above assays indicates that the compounds of the present invention are useful in the treatment of endometriosis.

Inhibition of Aortal Smooth Cell Proliferation/Restenosis Test Procedure

Compounds of the present invention have capacity to inhibit aortal smooth cell proliferation. This can be demonstrated by using cultured smooth cells derived from rabbit aorta, proliferation being determined by the measurement of DNA synthesis. Cells are obtained by explant method as described in Ross, *J. of Cell Bio.* 50: 172 (1971). Cells are plated in 96 well microtiter plates for five days. The cultures become confluent and growth arrested. The cells are then transferred to Dulbecco's Modified Eagle's Medium (DMEM) containing 0.5–2% platelet poor plasma, 2 mM L-glutamine, 100 U/ml penicillin, 100 mg ml streptomycin, 1 mC/ml $^3$H-thymidine, 20 ng/ml platelet-derived growth factor, and varying concentrations of the present compounds. Stock solution of the compounds is prepared in dimethyl sulphoxide and then diluted to appropriate concentration (0.01–30 mM) in the above assay medium. Cells are then incubated at 37° C. for 24 hours under 5% $CO_2$/95% air. At the end of 24 hours, the cells are fixed in methanol. $^3$H thymidine incorporation in DNA is then determined by scintillation counting as described in Bonin, et al., *Exp. Cell Res.* 181: 475–482 (1989).

Inhibition of aortal smooth muscle cell proliferation by the compounds of the present invention are further demonstrated by determining their effects on exponentially growing cells. Smooth muscle cells from rabbit aortae are seeded in 12 well tissue culture plates in DMEM containing 10% fetal bovine serum, 2 mM L-glutamine, 100 U/ml penicillin, and 100 mg/ml streptomycin. After 24 hours, the cells are attached and the medium is replaced with DMEM containing 10% serum, 2 mM L-glutamine, 100 U/ml penicillin, 100 mg/ml streptomycin, and desired concentrations of the compounds. Cells are allowed to grow for four days. Cells are treated with trypsin and the number of cells in each culture is determined by counting using a ZM-Coulter counter.

Activity in the above tests indicates that the compounds of the present invention are of potential in the treatment of restenosis.

The present invention also provides a method of alleviating post-menopausal syndrome in women which comprises the aforementioned method using compounds of Formula I and further comprises administering to a woman an effective amount of estrogen or progestin. These treatments are particularly useful for treating osteoporosis and lowering serum cholesterol because the patient will receive the benefits of each pharmaceutical agent while the compounds of the present invention would inhibit undesirable side-effects of estrogen and progestin. Activity of these combination treatments in any of the post-menopausal tests, infra, indicates that the combination treatments are useful for alleviating the symptoms of post-menopausal symptoms in women.

Various forms of estrogen and progestin are commercially available. Estrogen-based agents include, for example, ethynyl estrogen (0.01–0.03 mg/day), mestranol (0.05–0.15 mg/day), and conjugated estrogenic hormones such as Premarin® (Wyeth-Ayerst; 0.3–2.5 mg/day). Progestin-based agents include, for example, medroxyprogesterone such as Provera® (Upjohn; 2.5–10 mg/day), norethylnodrel (1.0–10.0 mg/day), and nonethindrone (0.5–2.0 mg/day). A preferred estrogen-based compound is Premarin, and norethylnodrel and norethindrone are preferred progestin-based agents.

The method of administration of each estrogen- and progestin-based agent is consistent with that which is known in the art. For the majority of the methods of the present invention, compounds of Formula I and II are administered continuously, from 1 to 3 times daily. However, cyclical therapy may especially be useful in the treatment of endometriosis or may be used acutely during painful attacks of the disease. In the case of restenosis, therapy may be limited to short (1–6 months) intervals following medical procedures such as angioplasty.

As used herein, the term "effective amount" means an amount of compound of the present invention which is capable of alleviating the symptoms of the various pathological conditions herein described. The specific dose of a compound administered according to this invention will, of course, be determined by the particular circumstances surrounding the case including, for example, the compound administered, the route of administration, the state of being of the patient, and the pathological condition being treated. A typical daily dose will contain a nontoxic dosage level of from about 5 mg to about 600 mg/day of a compound of the present invention. Preferred daily doses generally will be from about 15 mg to about 80 mg/day.

The compounds of this invention can be administered by a variety of routes including oral, rectal, transdermal, subucutaneus, intravenous, intramuscular, and intranasal. These compounds preferably are formulated prior to administration, the selection of which will be decided by the attending physician. Thus, another aspect of the present invention is a pharmaceutical composition comprising an effective amount of a compound of Formula I or II, or a pharmaceutically acceptable salt thereof, optionally containing an effective amount of estrogen or progestin, and a pharmaceutically acceptable carrier, diluent, or excipient.

The total active ingredients in such formulations comprises from 0.1% to 99.9% by weight of the formulation. By "pharmaceutically acceptable" it is meant the carrier, diluent, excipients and salt must be compatible with the other ingredients of the formulation, and not deleterious to the recipient thereof.

Pharmaceutical formulations of the present invention can be prepared by procedures known in the art using well known and readily available ingredients. For example, the compounds of formula I and II, with or without an estrogen or progestin compound, can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinylpyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds also can be formulated as elixirs or solutions for convenient oral administration or as solutions appropriate for parenteral administration, for example, by intramuscular, subcutaneous or intravenous routes. Additionally, the compounds are well suited to formulation as sustained release dosage forms and the like. The formulations can be so constituted that they release the active ingredient only or preferably in a particular physiological location, possibly over a period of time. The coatings, envelopes, and protective matrices may be made, for example, from polymeric substances or waxes.

Compounds of formula I and II, alone or in combination with a pharmaceutical agent of the present invention, generally will be administered in a convenient formulation. The following formulation examples only are illustrative and are not intended to limit the scope of the present invention.

Formulations

In the formulations which follow, "active ingredient" means a compound of formula I or II, or a salt or solvate thereof.

Formulation 1: Gelatin Capsules

Hard gelatin capsules are prepared using the following:

| Ingredient | Quantity (mg/capsule) |
| --- | --- |
| Active ingredient | 0.1–1000 |
| Starch, NF | 0–650 |
| Starch flowable powder | 0–650 |
| Silicone fluid 350 centistokes | 0–15 |

The formulation above may be changed in compliance with the reasonable variations provided.

A tablet formulation is prepared using the ingredients below:

Formulation 2: Tablets

| Ingredient | Quantity (mg/tablet) |
| --- | --- |
| Active ingredient | 2.5–1000 |
| Cellulose, microcrystalline | 200–650 |
| Silicon dioxide, fumed | 10–650 |
| Stearate acid | 5–15 |

The components are blended and compressed to form tablets.

Alternatively, tablets each containing 2.5–1000 mg of active ingredient are made up as follows:

Formulation 3: Tablets

| Ingredient | Quantity (mg/tablet) |
| --- | --- |
| Active ingredient | 25–1000 |
| Starch | 45 |
| Cellulose, microcrystalline | 35 |
| Polyvinylpyrrolidone (as 10% solution in water) | 4 |
| Sodium carbomethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of medicament per 5 ml dose are made as follows:

Formulation 4: Suspensions

| Ingredient | Quantity (mg/5 ml) |
| --- | --- |
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

An aerosol solution is prepared containing the following ingredients:

Formulation 5: Aerosol

| Ingredient | Quantity (% by weight) |
| --- | --- |
| Active ingredient | 0.25 |
| Ethanol | 25.75 |
| Propellant 22 (Chlorodifluoromethane) | 70.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container.

Suppositories are prepared as follows: Formulation 6: Suppositories

| Ingredient | Quantity (mg/suppository) |
| --- | --- |
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool. An intravenous formulation is prepared as follows:

Formulation 7: Intravenous Solution

| Ingredient | Quantity |
| --- | --- |
| Active ingredient | 50 mg |
| Isotonic saline | 1,000 mL |

The solution of the above ingredients is intravenously administered to a patient at a rate of about 1 mL per minute.

Formulation 8: Combination Capsule I

| Ingredient | Quantity (mg/capsule) |
| --- | --- |
| Active ingredient | 50 |
| Premarin | 1 |
| Avicel pH 101 | 50 |
| Starch 1500 | 117.50 |
| Silicon Oil | 2 |
| Tween 80 | 0.50 |
| Cab-O-Sil | 0.25 |

Formulation 9: Combination Capsule II

| Ingredient | Quantity (mg/capsule) |
| --- | --- |
| Active ingredient | 50 |
| Norethylnodrel | 5 |
| Avicel pH 101 | 82.50 |
| Starch 1500 | 90 |
| Silicon Oil | 2 |
| Tween 80 | 0.50 |

73

Formulation 10: Combination Tablet

| Ingredient | Quantity (mg/capsule) |
| --- | --- |
| Active ingredient | 50 |
| Premarin | 1 |
| Corn Starch NF | 50 |
| Povidone, K29-32 | 6 |
| Avicel pH 101 | 41.50 |
| Avicel pH 102 | 136.50 |
| Crospovidone XL10 | 2.50 |
| Magnesium Stearate | 0.50 |
| Cab-O-Sil | 0.50 |

The compounds of the present invention may contain one or more assymetric centers, and therefore can exist as a mixture of isomers, or as individual isomers. Either a mixture or individual isomers will be useful for the purposes of the present invention, and can be so employed.

I claim:

1. A compound of formula I:

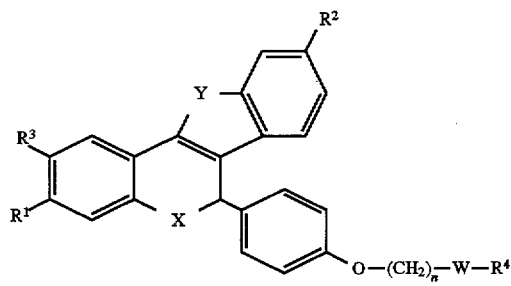

wherein

X is —O—, or —S—;

Y is —O—, —S—, —CH$_2$—, —CH$_2$CH$_2$—, —CH=CH—, or —NR$^5$—;

R$^1$, R$^2$, and R$^3$ are each independently —H, —OH, —O(C$_1$–C$_4$ alkyl), —OCOC$_6$H$_5$, —OCO(C$_1$–C$_6$ alkyl), —OSO$_2$(C$_4$–C$_6$ alkyl), —OSO$_2$CF$_3$, Cl, or F;

n is 1 or 2;

W is CH$_2$ or C=O;

R$^4$ is 1-piperidinyl, 2-oxo-1-piperidinyl, 1-pyrrolidinyl, methyl-1-pyrrolidinyl, dimethyl-1-pyrrolidinyl, 2-oxo-1-pyrrolidinyl, 4-morpholino, dimethylamino, diethylamino, or 1-hexamethyleneimino;

R$^5$ is C$_1$–C$_3$ alkyl, —COC$_6$H$_5$, —CO(C$_1$–C$_6$ alkyl), —C(O)OC$_6$H$_5$, —C(O)O(C$_1$–C$_6$ alkyl), —SO$_2$(C$_1$–C$_6$ alkyl), —SO$_2$C$_6$H$_5$, or —SO$_2$CF$_3$; or a pharmaceutically acceptable salt or solvate thereof.

2. A compound according to claim 1 which is of Formula I and wherein X is —O— and Y is —S—.

3. A compound according to claim 1 wherein —O—(CH$_2$)$_n$—W—R$^4$ is 2-(1-piperidinyl)ethoxy.

4. A compound according to claim 1 which is selected from the group consisting of:

3,9-dihydroxy-6-[4-[2-(1-piperidinyl)ethoxy]phenyl]-6-H-[1]benzothieno[3,2-c][1]benzopyran;

3,9-dimethoxy-6-[4-[2-(1-piperidinyl)ethoxy]phenyl]-6-H-[1]benzothieno[3,2-c][1]benzopyran;

3,9-bis(benzoyloxy)-6-[4-[2-(1-piperidinyl)ethoxy]phenyl]-6-H-[1]benzothieno[3,2-c][1]benzopyran;

3,9-bis(pivaloyloxy)-6-[4-[2-(1-piperidinyl)ethoxy]phenyl]-6-H-[1]benzothieno[3,2-c][1]benzopyran;

3,9-bis(1-butylsulfonyloxy)-6-[4-[2-(1-piperidinyl)ethoxy]phenyl]-6-H-[1]benzothieno[3,2-c][1]benzopyran;

74

3,9-bis(trifluoromethanesulfonyloxy)-6-[4-[2-(1-piperidinyl)ethoxy]phenyl]-6-H-[1]benzothieno[3,2-c][1]benzopyran;

6-[4-[2-(1-piperidinyl)ethoxy]phenyl]-6-H-[1]benzothieno[3,2-c][1]benzopyran;

3,9-dihydroxy-6-[4-[2-(1-pyrrolidinyl)ethoxy]phenyl]-6H-[1]benzothieno[3,2-c][1]benzopyran;

3,9-dihydroxy-6-[4-(2-dimethylaminoethoxy)phenyl]-6-H-[1]benzothieno[3,2-c][1]benzopyran;

3,9-dihydroxy-6-[4-[2-(2-oxo-1-pyrrolidinyl)ethoxy]phenyl]-6-H-[1]benzothieno[3,2-c][1]benzopyran;

3,9-dihydroxy-6-[4-[2-(1-piperidinyl)ethoxy]phenyl]-6-H-benzofuro[3,2-c][1]benzopyran;

2,8-dihydroxy-5-[4-[2-(1-piperidinyl)-ethoxy]phenyl]-5H-benzo[b]naphtho[2,1-d]pyran.

5. A process for preparing a compound of formula I

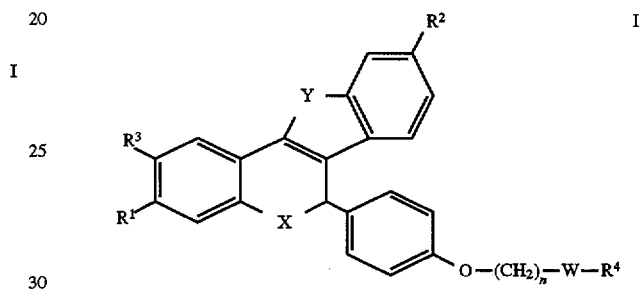

wherein

X is —O— or —S—;

Y is —O—, —S—, —CH$_2$—, —CH$_2$CH$_2$—, —CH=CH—, or —NR$^5$—;

R$^1$, R$^2$, and R$^3$ are each independently —H, —OH, —O(C$_1$–C$_4$ alkyl), —OCOC$_6$H$_5$, —OCO(C$_1$–C$_6$ alkyl), —OSO$_2$(C$_4$–C$_6$ alkyl), —OSO$_2$CF$_3$, Cl, or F;

n is 1 or 2;

W is CH$_2$ or C=O;

R$^4$ is 1-piperidinyl, 2-oxo-1-piperidinyl, 1-pyrrolidinyl, methyl-1-pyrrolidinyl, dimethyl-1-pyrrolidinyl, 2-oxo-1-pyrrolidinyl, 4-morpholino, dimethylamino, diethylamino, or 1-hexamethyleneimino;

R$^5$ is C$_1$–C$_3$ alkyl, —COC$_6$H$_5$, —CO(C$_1$–C$_6$ alkyl), —C(O)OC$_6$H$_5$, —C(O)O(C$_1$–C$_6$ alkyl), —SO$_2$(C$_1$–C$_6$ alkyl), —SO$_2$C$_6$H$_5$, or —SO$_2$CF$_3$; or a pharmaceutically acceptable salt thereof, which comprises:

(1) reacting a compound of formula III

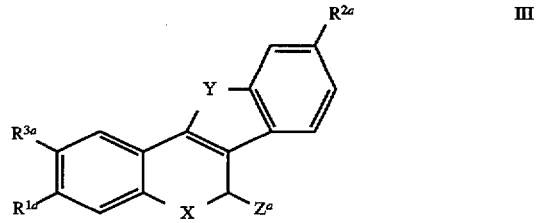

wherein

R$^{1a}$, R$^{2a}$ and R$^{3a}$ are each independently H, —O(C$_1$–C$_4$ alkyl), —Cl, —F, or a protected —OH;

X and Y are as defined above; and Z$^a$ is —OH, —OC$_6$H$_5$, or —O(C$_1$–C$_4$ alkyl), with a Grignard reagent of the formula

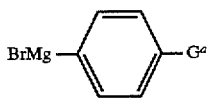

wherein $G^a$ is —OSi(CH$_3$)$_3$, a protected OH capable of being selectively deprotected in the presence of $R^{1a}$, $R^{2a}$ and $R^{3a}$, or —(CH$_2$)$_n$WR$^4$; to obtain a compound of the formula

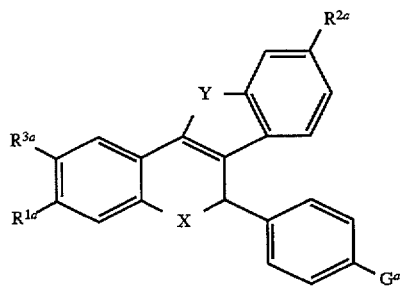

(2) in the instance when $G^a$ is —OSi(CH$_3$)$_3$ or a protected OH as defined, (a) treating the product of step (1) to selectively deprotect to a compound of the formula

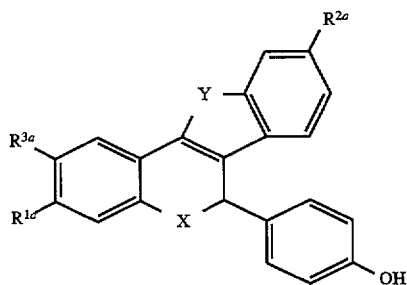

and thereafter (b) alkylating this compound to a compound of the formula

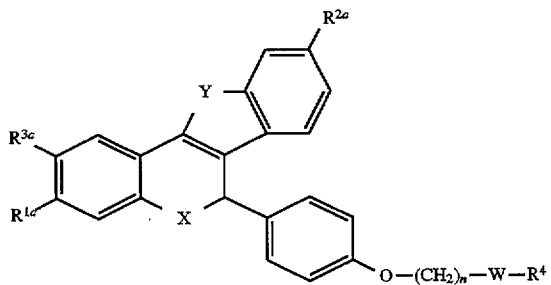

(3) deprotecting any protected OH groups in $R^{1a}$, $R^{2a}$, or $R^{3a}$ in the compound from step 1 or step 2, to obtain the compound of the formula:

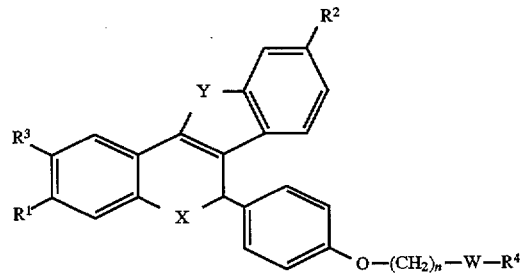

and (4) optionally salifying the product of the preceding step.

6. A compound of formula III

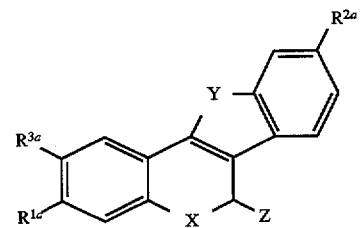

wherein

X is —O— or —S—;

Y is —O—, —S—, —CH$_2$—, —CH$_2$CH$_2$—, —CH=CH— or —NR$^5$—;

each of $R^{1a}$, $R^{2a}$ and $R^{3a}$ is independently —H, —O(C$_1$-C$_4$ alkyl), —Cl, —F, or a protected —OH; and Z is —OH, —OC$_6$H$_5$, —O(C$_1$-C$_4$ alkyl), or 4-hydroxyphenyl.

7. A pharmaceutical composition comprising a compound according to claim 1 together with a pharmaceutically acceptable carrier, diluent or excipient.

8. A method for inhibiting bone loss or bone resorption comprising administering to a patient in need thereof an effective amount of a compound of claim 1.

9. A method according to claim 8 wherein said bone loss or bone resorption is due to menopause or ovariectomy.

10. A method of lowering serum cholesterol levels comprising administering to a patient in need thereof an effective amount of a compound of claim 1.

* * * * *